United States Patent
Ke et al.

(10) Patent No.: US 12,188,015 B2
(45) Date of Patent: Jan. 7, 2025

(54) TYPE I CRISPR SYSTEM AS A TOOL FOR GENOME EDITING

(71) Applicants: Cornell University, Ithaca, NY (US); The Regents of the University of Michigan, Ann Arbor, MI (US)

(72) Inventors: Ailong Ke, Ithaca, NY (US); Adam Dolan, Ithaca, NY (US); Yan Zhang, Ann Arbor, MI (US); Zhonggang Hou, Ann Arbor, MI (US)

(73) Assignees: Cornell University, Ithaca, NY (US); The Regents of the University of Michigan, Ann Arbor, MI (US)

( * ) Notice: Subject to any disclaimer, the term of this patent is extended or adjusted under 35 U.S.C. 154(b) by 909 days.

(21) Appl. No.: 17/254,169

(22) PCT Filed: Jun. 21, 2019

(86) PCT No.: PCT/US2019/038529
§ 371 (c)(1),
(2) Date: Dec. 18, 2020

(87) PCT Pub. No.: WO2019/246555
PCT Pub. Date: Dec. 26, 2019

(65) Prior Publication Data
US 2022/0315920 A1    Oct. 6, 2022

Related U.S. Application Data

(60) Provisional application No. 62/829,091, filed on Apr. 4, 2019, provisional application No. 62/688,202, filed on Jun. 21, 2018.

(51) Int. Cl.
| | | |
|---|---|---|
| C12N 15/11 | (2006.01) | |
| C12N 9/22 | (2006.01) | |
| C12N 15/90 | (2006.01) | |

(52) U.S. Cl.
CPC ............ *C12N 15/11* (2013.01); *C12N 9/22* (2013.01); *C12N 15/907* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 2015/0315576 A1 | 11/2015 | Caliando et al. |
| 2016/0186214 A1 | 6/2016 | Brouns et al. |
| 2017/0028083 A1 | 2/2017 | Beisel et al. |
| 2017/0260546 A1 | 9/2017 | Qimron et al. |
| 2018/0282763 A1 | 10/2018 | Cigan et al. |
| 2018/0334688 A1 | 11/2018 | Gersbach et al. |
| 2019/0024098 A1 | 1/2019 | Nishida et al. |
| 2020/0102580 A1 | 4/2020 | Mashimo et al. |

FOREIGN PATENT DOCUMENTS

| | | | | |
|---|---|---|---|---|
| WO | 2015/155686 A2 | 10/2015 | | |
| WO | WO-2017066497 A2 * | 4/2017 | ........... | C12N 15/102 |
| WO | 2017/219033 A1 | 12/2017 | | |

OTHER PUBLICATIONS

Brown et al. Oct. 23, 2017. Assembly and translocation of a CRISPR-Cas primed acquisition complex. bioRxiv 208058. https://doi.org/10.1101/208058 (Year: 2017).*

WP_011292019, type I-E CRISPR-associated protein Cse2/CasB [Thermobifida fusca], 2015 (Year: 2015).*

GenBank: AAZ55629.1, CRISPR-associated helicase, Cas3 family [Thermobifida fusca YX], 2014 (Year: 2014).*

Brown, M.W., et al., Assembly and translocation of a CRISPR-Cas primed acquisition complex, BioRxiv, Oct. 23, 2017, pp. 1-10.

Brouns, S.J.J., et al., Small CRISPR RNAs Guide Antiviral Defense in Prokaryotes, Science, Aug. 15, 2008, vol. 321, No. 5891,j pp. 960-964.

Huo, Y., et al., Structures of CRISPR Cas3 offer mechanistic insights into Cascade-activated DNA unwinding and degradation, Nature Structural & Molecular Biology, Sep. 2014, vol. 21, No. 9, pp. 771-777.

Hochstrasser, M.L., CasA mediates Cas3-catalyzed target degradation during CRISPR RNA-guided interference, PNAS, May 6, 2014, vol. 11, No. 18, pp. 6618-6623.

Mansouri, M., et al., Baculovirus-based genome editing in primary cells, Plasmid, Jan. 22, 2017, vol. 90, pp. 5-9.

* cited by examiner

*Primary Examiner* — Celine X Qian
*Assistant Examiner* — Tiffany Nicole Grooms
(74) *Attorney, Agent, or Firm* — Hodgson Russ LLP

(57) ABSTRACT

Provided are compositions, methods, and kits for CRISPR-based editing of DNA targets by Type I CRISPR-associated (Cas) enzymes.

19 Claims, 26 Drawing Sheets

Specification includes a Sequence Listing.

E.

| Group no. | Nucleotides deleted |
|---|---|
| Group I | -18800 – -368 (Δ18431 nt) |
| Group I | -4928 – +86 (Δ5012 nt) |
| Group II | -8435 – +86 (Δ8519 nt) |
| Group III | -3909 – +116 (Δ4025 nt) |
| Group IV | -20002 – -16498 (Δ3503 nt) |
| Group IV | -16459 – -126 (Δ16332 nt) |

FIG. 4 (continued)

| Clone no. | Deletion junctions |
|---|---|
| Clone #1 | -2378 – 135 (Δ2511 nt) |
| Clone #2 | -4201 – 156 (Δ4355 nt) |
| Clone #3 | -2049 – 12 (Δ2060 nt) |
| Clone #4 | -3703 – 209 (Δ3911 nt) |
| Clone #5 | -2594 – 99 (Δ2692 nt) |
| Clone #6 | -2973 – 104 (Δ3075 nt) |
| Clone #7 | -3006 – 89 (Δ3093 nt) |
| Clone #8 | -2622 – 3 (Δ2623 nt) |
| Clone #9 | -7801 – -179 (Δ7979 nt) |
| Clone #10 | -7962 – 271 (Δ7961 nt) |
| Clone #11 | -7237 – 55 (Δ7290 nt) |
| Clone #12 | -7632 – 94 (Δ7723 nt) |
| Clone #13 | -7924 – 157 (Δ8079 nt) |
| Clone #14 | -7070 – 87 (Δ7155 nt) |
| Clone #15 | -4273 – 8 (Δ4280 nt) |
| Clone #16 | -3256 – 18 nt insertion – 201 (Δ3456 nt) |
| Clone #18 | -4295 – 82 (Δ4375 nt) |
| Clone #19 | -2995 – 34 (Δ3027 nt) |
| Clone #47 | -20002 – 16498 (Δ3503 nt) |
| Clone #47 | -16459 – -126 (Δ16332 nt) |

FIG. 10

TYPE I CRISPR SYSTEM AS A TOOL FOR GENOME EDITING

CROSS-REFERENCE TO RELATED APPLICATIONS

This application claims priority to U.S. provisional patent application No. 62/688,202, filed Jun. 21, 2018, and to U.S. provisional patent application No. 62/829,091, filed Apr. 4, 2019, the entire disclosures of each of which are incorporated herein by reference.

SEQUENCE LISTING

The instant application contains a Sequence Listing, which is submitted in xml format and is hereby incorporated by reference in its entirety. Said.xml file is named "018617_01053_Seq_listing.xml", was created on Nov. 16, 2019, and is 67,000 bytes in size.

STATEMENT REGARDING FEDERALLY SPONSORED RESEARCH OR DEVELOPMENT

This invention was made with government support under Grant No. 5R35GM118174 and 5R00GM117268 awarded by the National Institutes of Health. The government has certain rights in the invention.

FIELD OF THE DISCLOSURE

The present disclosure is related to compositions and methods use in modifying DNA in eukaryotic cells using CRISPR Type I systems.

BACKGROUND OF THE DISCLOSURE

There is an ongoing and unmet need for improvements in CRISPR-Cas targeting and editing. The present disclosure is pertinent to this need.

SUMMARY

The present disclosure demonstrates use of Type I CRISPR-Cas systems to effectively introduce a spectrum of long-range chromosomal deletions with a single RNA guide in human embryonic stem cells and HAP1 cells. Type I CRISPR systems rely on the multi-subunit ribonucleoprotein (RNP) complex Cascade to identify DNA targets, and the helicase-nuclease enzyme Cas3 to degrade DNA processively. With various types of delivery approaches for *T. fusca* Cascade and Cas3, we obtained 5%-95% editing efficiency. Long-range PCR- and high-throughput sequencing-based lesion analyses reveal that a variety of deletions, ranging from a few hundred base-pairs to 100 kilobases, are created upstream of the target site. These results highlight the utility of Type I CRISPR-Cas for long-range genome manipulations and deletion screens in eukaryotes.

In embodiments, the disclosure provides for use of *T. fusca* proteins, or homologues thereof, for use in modifying DNA, such as chromosomal DNA, or extrachromosomal dsDNA. In embodiments, the disclosure provides a method of modifying DNA in eukaryotic cells by introducing into the eukaryotic cells: (i) a combination of proteins comprising Cas3, Cse1/CasA, Cse2/CasB, Cas7/CasC, Cas5e/CasD and Cas6e/CasE, each comprising an amino acid sequence that is at least 85% homologous across its entire length to a *Thermobifida Fusca* (*T. fusca*) protein; (ii) a guide RNA (a targeting RNA) comprising a sequence that is complementary to a targeted site in a segment of the DNA, the targeted site comprising a spacer sequence; and (iii) allowing the combination of the proteins and the guide RNA to modify the DNA by nicking, causing a double stranded break (DSB), and/or unidirectional deleting of a single strand of the DNA. The method, among other features, leaves the targeted site intact. In embodiments, long deletions, such as up to 100 kb, are introduced.

The disclosure includes data demonstrating that the presently provided systems are more efficient than others in a variety of ways, one non-limiting example of which is being able to function efficiently at physiological temperature, such as a temperature of about 37° C.

While various homologous, and mutations of the proteins described herein are encompassed by the disclosure, in certain implementations, the Cas3 protein comprises the sequence of SEQ ID NO:1 or a sequence that is at least 85% homologous across its entire length to the sequence of SEQ ID NO:1. In certain embodiments, the sequence of the Cse2/CasB protein comprises the sequence of SEQ ID NO:2 or a sequence that is at least 85% homologous across the entire length sequence of SEQ ID NO:2. In certain embodiments, the Cse2/CasB protein comprises a mutation of N23, which is optionally N23A, which has enhanced function at a temperature of 37° C., and at higher temperatures.

The methods provide for modifying DNA in a population of cells, such as a population of eukaryotic cells an in vitro cell culture. This facilitates greater DNA modification efficiency than previously available approaches. For example, in certain embodiments, a DNA segment is modified in at 10%-100% of the cells in an in vitro cell culture, or in 10%-100% of the cells that receive the system.

In certain embodiments, use of the described system produces a deletion upstream of a targeted site that comprises a deletion of from about 500 base pairs to about 100,000 base pairs. The disclosure further comprises modifying DNA in eukaryotic cells by introducing a DNA repair template, such that the sequence of the DNA repair template is incorporated into a chromosome. For example, single-stranded DNA may be exposed during Cascade-Cas3 mediated DNA degradation, which can allow gene conversion by introducing a DNA repair template, such that the sequence of the DNA repair template is incorporated into a chromosome. This approach can be used for a variety of purposes, such as introducing mutations, indels, and gene conversion approaches. The described systems can be introduced into the cells using a variety of approaches, such as by using mRNA, or a ribonucleoprotein (RNP) complex, or plasmids or other expression vectors, or combinations thereof. The disclosure includes modified eukaryotic cells made by the described methods, and non-human animals comprising or produced from the cells.

The disclosure also provides kits which may comprise combination of recombinant proteins, and/or or one or more polynucleotides that can express a combination of proteins.

BRIEF DESCRIPTION OF THE FIGURES

FIG. 10. Examples of four different categories of deletion/repair junctions identified by Sanger sequencing. Related to FIG. 4. Representative lesion junction events described in FIG. 4 are shown by position. The dashed black line denotes deletion/repair junctions. Genomic positions flanking the long-range deletion, relative to the EGFP translation start site (+1), are indicated on the top. Sizes of the deletions are shown in parentheses. Insertions at the junction are shaded in orange; point mutations at the junction are shaded in pink, with the wild-type sequence indicated.

DETAILED DESCRIPTION OF THE DISCLOSURE

Figure 1:
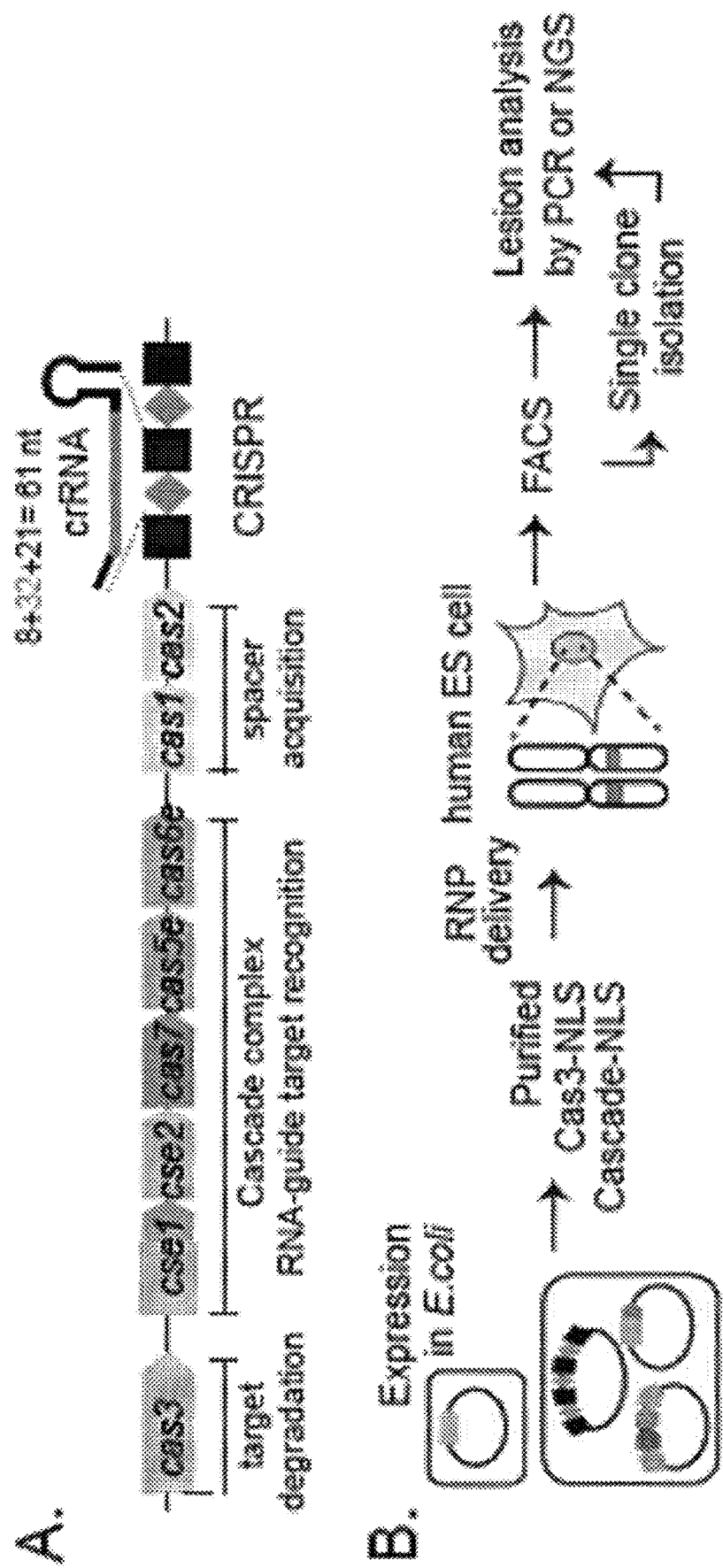
FIG. 1. Type I CRISPR-Cas can enable RNA-guided genome editing in human ES cells. (A) Schematic diagram of the *T. fusca* Type I-E CRISPR-cas locus. Rectangles and diamonds represent CRISPR repeats and spacers; shaded boxes, cas genes. (B) Procedure of the genome editing experiments in hESCs. (C) Schematic of the hESC dual-reporter line bearing EGFP and tdTomato at the DNMT3B locus. Top strand sequence for dTomato: caccaagctggacatcacctcccacaacgaggactacaccatc (SEQ ID NO:137); bottom strand sequence for dTomato: gatggtgtagtcctcgttgtgggaggt-gatgtccagcttggtg (SEQ ID NO:138). Top strand sequence for GFP (first double stranded GFP DNA sequence): cccgaaggc-tacgtccaggagcgcaccatcttcttcaaggacg (SEQ ID NO:139); bottom strand sequence for GFP (first double stranded GFP DNA sequence): cgtccttgaagaa-gatggtgcgctcctggacgtagccttcggg (SEQ ID NO:140). Top strand sequence for GFP (second double stranded GFP DNA sequence): acacacctggtgaaccgcatcgagctgasagggcatcgacttcaa (SEQ ID NO:141); bottom strand sequence for GFP (second double stranded GFP DNA sequence): ttgaagtc-gatgcccttcagctcgatgcggttcaccagggtgt (SEQ ID NO:142). Protospacers for the three reporter-targeting crRNAs are indicated, as well as corresponding PAMs. (D-F) Flow cytometry analysis of the dual-reporter hESC line 4-5 days after RNP delivery. Percentages of EGFP-negative/tdTomato-positive cells (boxed) are indicated in (D) (E), and percentages of EGPF-positive/tdTomato-negative cells (boxed) are indicated in (F).
Figure 1:
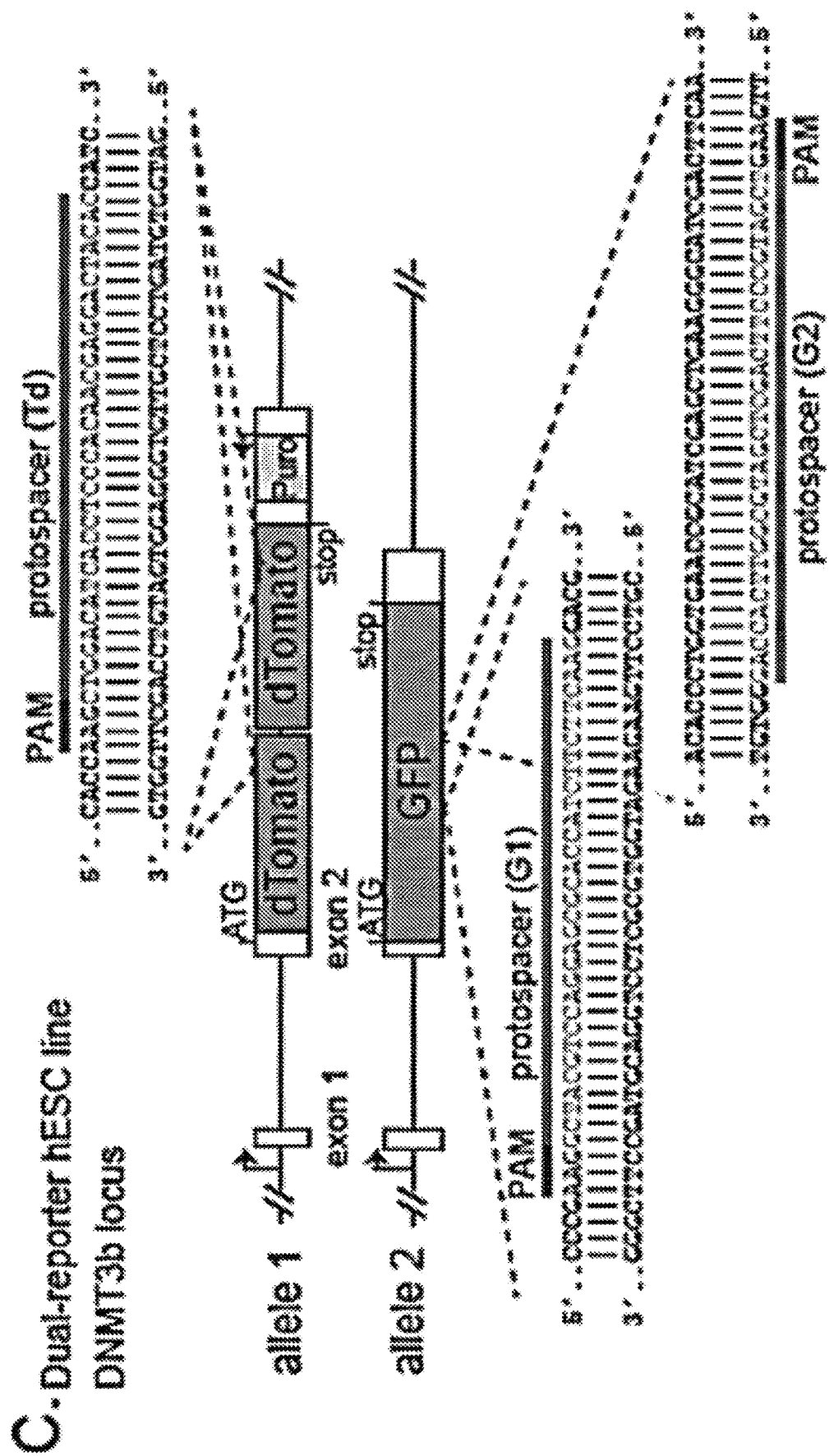
Figure 1:
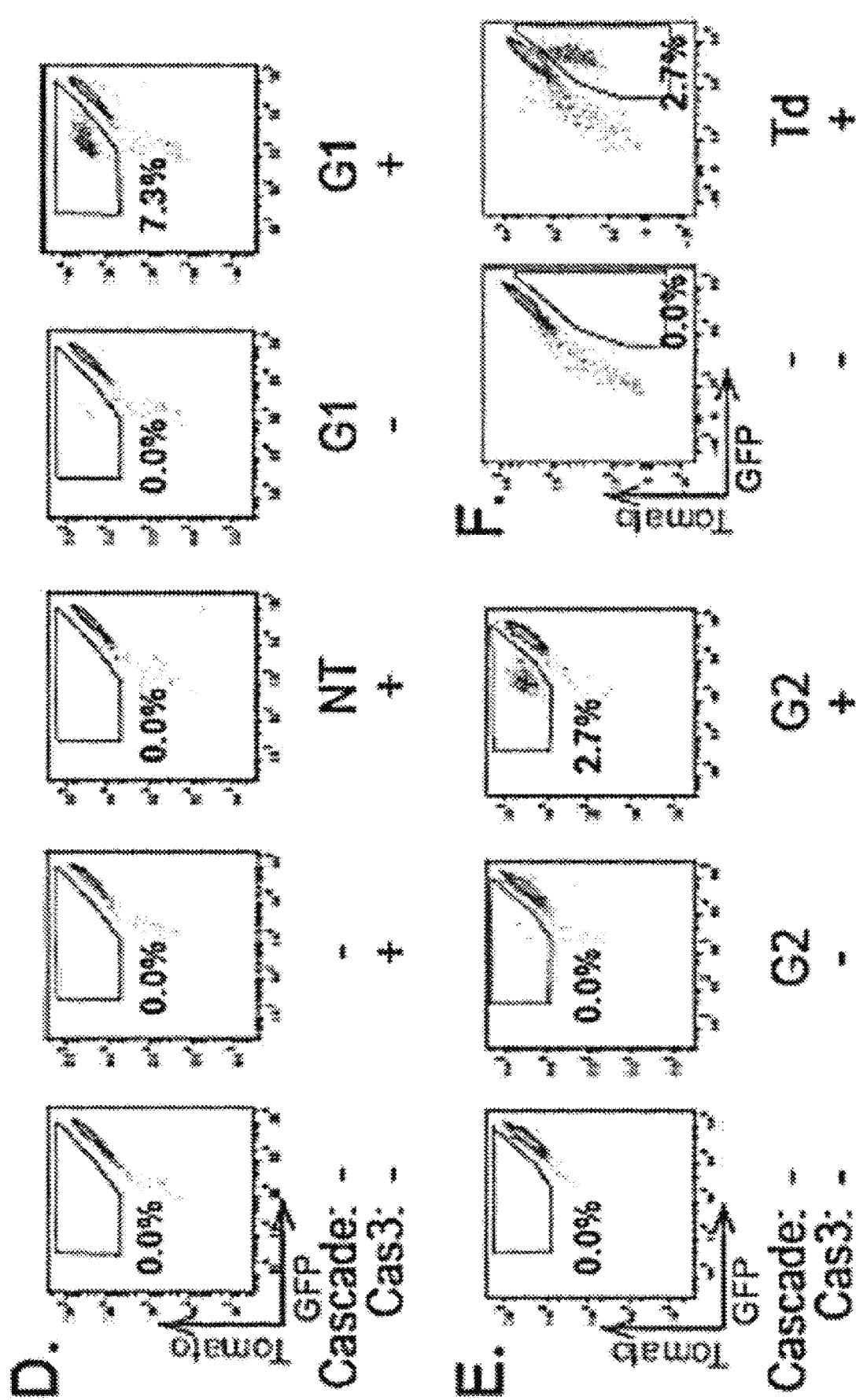

Unless defined otherwise herein, all technical and scientific terms used herein have the same meaning as commonly understood by one of ordinary skill in the art to which this disclosure pertains.

Unless specified to the contrary, it is intended that every maximum numerical limitation given throughout this description includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All nucleotide sequences described herein include the RNA and DNA equivalents of such sequences, i.e., an RNA sequence includes its cDNA. All nucleotide sequences include their complementary sequences.

All temperatures and ranges of temperatures, all buffers, and other reagents, and all combinations thereof, are included in this disclosure.

All nucleotide and amino acid sequences identified by reference to a database, such as a GenBank database reference number, are incorporated herein by reference as the sequence exists on the filing date of this application or patent.

The disclosure includes all embodiments illustrated in the Figures provided with this disclosure.

Any component of the editing systems described herein can be provided on the same or different polynucleotides, such as plasmids, or a polynucleotide integrated into a chromosome. In embodiments, at least one component of the system is heterologous to the cells. In eukaryotic cells, all components of the system can be heterologous.

In embodiments the present disclosure provides compositions and methods for improving the specificity, efficiency, or other desirable properties of Type I CRISPR-based gene editing or target destruction in any eukaryotic cell or eukaryotic organism of interest.

As used herein, the term "Cascade" refers to an RNA-protein complex that is responsible for identifying a DNA target in crRNA-dependent fashion. In this regard, Cascade (CRISPR-Associated Complex for Anti-viral Defense) is a ribonucleoprotein complex comprised of multiple protein subunits and is used naturally in bacteria as a mechanism for nucleic acid-based immune defense. Cascade complexes are characteristic of the Type I CRISPR systems. The Cascade complex recognizes nucleic acid targets via direct base-pairing to an RNA guide contained in the complex. Acceptance of target recognition by Cascade results in a conformational change which, in *E. coli* and other bacteria, recruits a protein component referred to from time to time as Cas3. Cas3 may comprise a single protein unit which contains helicase and nuclease domains. After target validation by Cascade, Cas3 nicks the strand of DNA that is looped out by the R-loop formed by Cascade approximately 9-12 nucleotides inward from the PAM site. Cas3 then uses its helicase/nuclease activity to processively degrade substrate nucleic acids, moving in a 3' to 5' direction.

Mechanisms of previous Cas9, Cpf1, and other single-protein component genome editing, nucleic acid sequence marking, and general applications of nucleic acid modification solutions are fundamentally different than the same problems addressed using a Cascade complex, with or without Cas3, as demonstrated herein. In this regard, and without intending to be bound by any particular theory, it is known that Cas9 produces clean double strand breaks at the target site which is a structure that is inefficient for homology directed repair. Cpf1 produces short overhangs with 5' ends exposed, which are again not preferable substrates for homology directed repair. Cascade with Cas3 produces innate 3' overhangs on the target strand, which is a preferred substrate for homology directed repair. Further, the processive helicase nature of Cas3 provides a platform for targeted, but non-local modification of nucleic acids. Cas9 and other known single-protein component systems recognize a target sequence and do not translocate along DNA in the same way that Cas3 is known to function. This allows for a large region of DNA to be affected by Cas3 or Cas3-fusion proteins from a single targeting event. Further still, and again without intending to be bound by any particular theory, it is considered that target recognition and target degradation being separated by a conformational change validation step provides decreased off-target effects. This is because the nuclease component Cas3 is not present at the target site until after recognition has occurred. Additionally, wild-type Cascade has a 32 nucleotide spacer region (with 5 bases flipped out and not recognized by the crRNA) which makes 27 base pairs of recognition.

Thus, in embodiments, the disclosure comprises a crRNA as a guide RNA comprising constant regions at its 5' and 3'-ends and a variable region in the middle, which comprises a spacer for DNA targeting, and participates in R-loop formation. In embodiments, more than one Cascade/Cas3 is provided. In embodiments, more than one crRNA, or guide RNA is provided. In embodiments, 2, 3, 4, 5, or more crRNAs or guide RNAs are provided.

Figure 13:
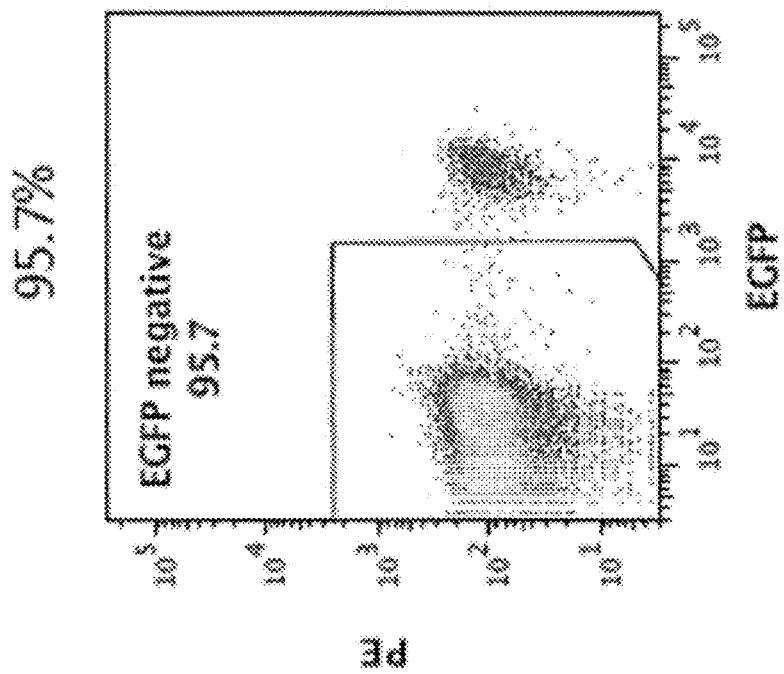
FIG. 13. Electroporation of Cascade+Cas3 RNP into HAP1-EGFP reporter cells enabled 96% editing. Highest eGFP-RNP editing efficiency achieved, 96%. The analysis was performed in novel reporter cell line HAP1-eGFP (neon electroporation).
Figure 13:
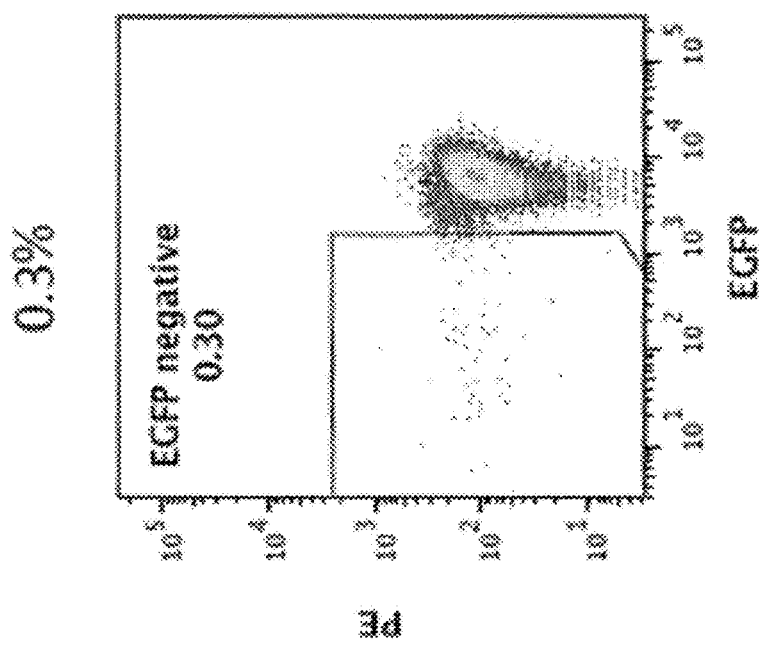
Figure 14:
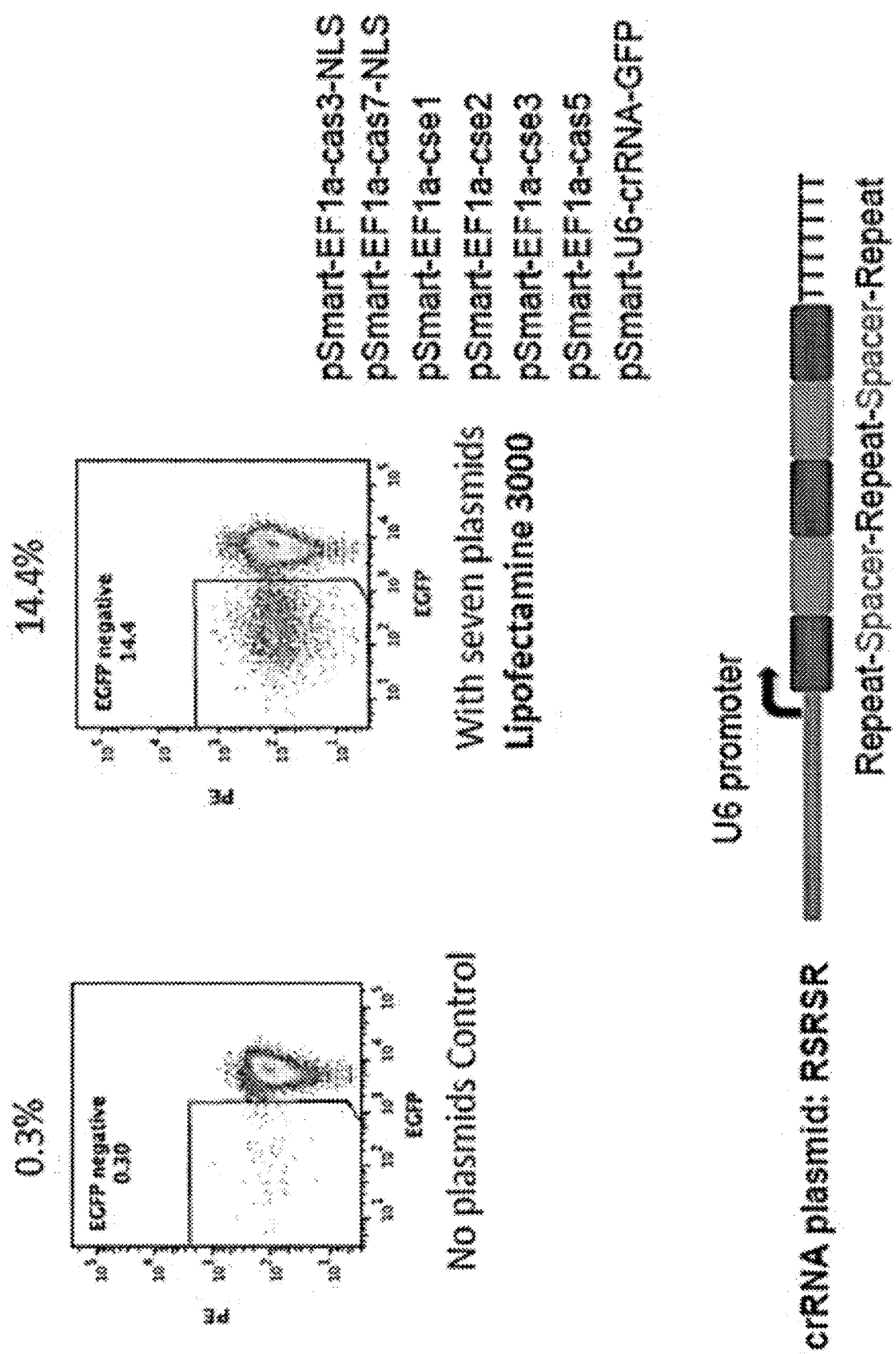
FIG. 14. Delivery of Cascade-Cas3 as plasmids into HAP1-EGFP reporter cells. Plasmid delivery leads to 14.4% editing (lipofectamine 3000).
Figure 15:
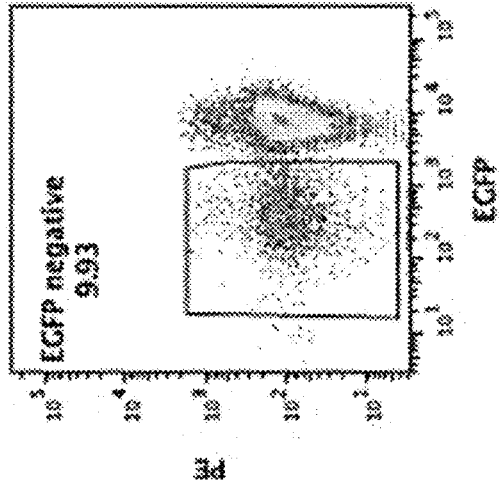
FIG. 15. Electroporation of all cas genes as mRNA+ crRNA as plasmid. Delivery of mRNAs (for all cas genes)+ crRNA plasmid resulted in 10% editing (neon electroporation).
Figure 15:
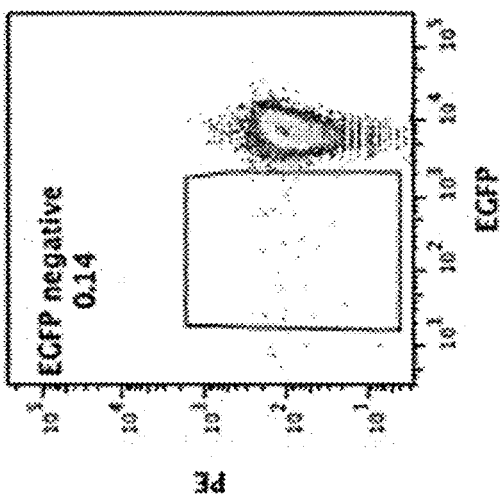
Figure 15:
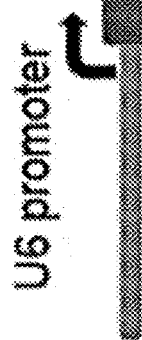

In embodiments, any enzyme or other protein as described herein is introduced into the cell as a recombinant or purified protein, or as an RNA encoding the protein that is expressed once introduced into the cell, or as an expression vector, which is expressed once in the cell. Any suitable expression system can be used and many are commercially available for use with the instant invention, given the benefit of the present description. In embodiments, one or more components of a Cascade system described herein can be delivered to cells as an RNP, or by one or more plasmids, or a combination of proteins, RNA, and/or DNA plasmids. Data presented in, for example, at least FIGS. 1 and 2, demonstrate use of RNP delivery. FIG. 13 demonstrates electroporation of Cascade+Cas3 RNP into HAP1-EGFP reporter cells produced 96% editing. FIG. 14 demonstrates Cascade-Cas3 delivery as plasmids, leading to 14.4% editing, meaning 14.4% of the cells in the cell culture were edited. FIG. 15 demonstrates electroporation of all cas genes as mRNA+crRNA as plasmid. Delivery of mRNAs (for all cas genes)+crRNA plasmid resulted in 10% editing. The percent editing is relative to total cell number in the cell culture.

In embodiments, the disclosure provides one or a combination of the following advantages, relative to certain previously available approaches: i) a multi-component system, ii) increased processivity, iii) selective for a single strand of substrate DNA; iv) longer crRNA; v) different PAM; vi) target recognition/cleavage separate events; vii) leaves behind a unique DNA lesion; viii) crRNA has a simpler structure than certain other systems; ix) leaves the target site intact, x) functions at higher temperatures than other systems.

As is known in the art, Cse1 is also referred to as CasA; Cse2 is also referred to as CasB; Cas7 refers to a combination of Cse4 and CasC; Cas6e is referred to as CasE; Cas3 refers to a contiguous polypeptide comprising nuclease and helicase activity, and degrades DNA after R-loop formation.

Figure 16:
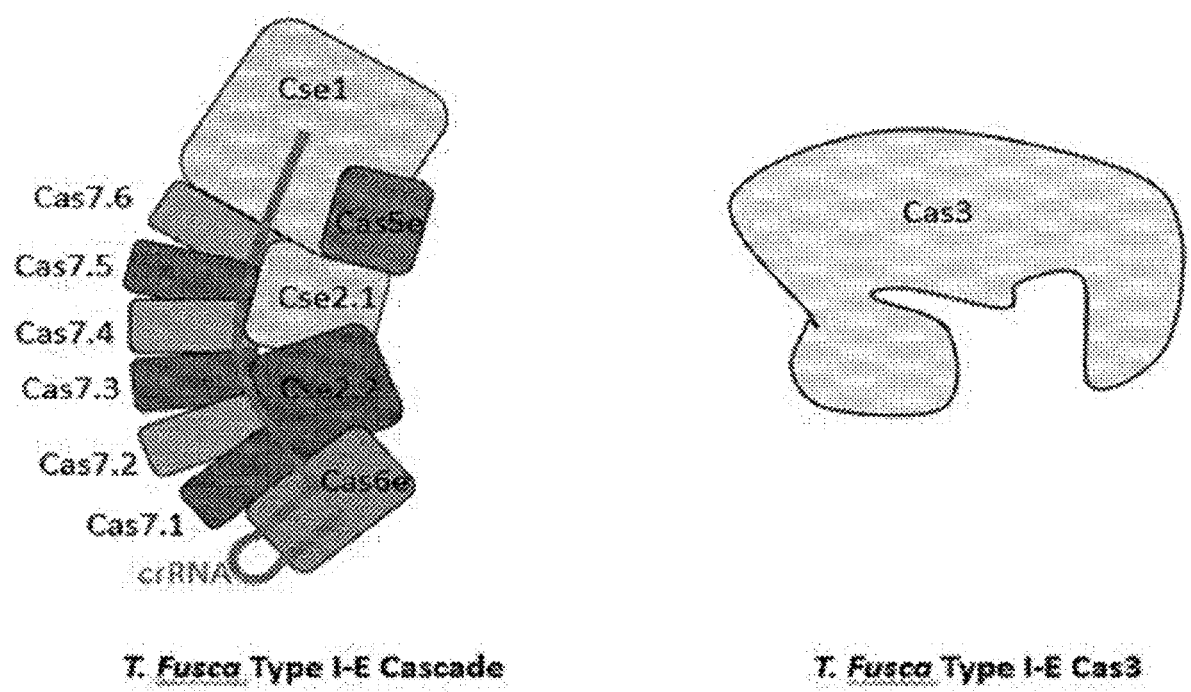
FIG. 16 provides a representative embodiment of a Cascade RNA-protein complex that may be used in embodiments of this disclosure. It shows 6 Cas7 units, one Cse1 unit, 2 Cse2 units, 1 Cse5 unit, and 1 Cas6e unit, along with a crRNA (left panel), and a representative CRISPR Type I-E Cas3 that can be used in embodiments of this disclosure from *T. fusca*, (right panel), but Cas3 from other types of bacteria can be used. In embodiments, a Cascade complex may be used with or without a Cas3.

FIG. 16 provides a representative embodiment of a Cascade RNA-protein complex that may be used in embodiments of this disclosure. It shows 6 Cas7 units, one Cse1 unit, 2 Cse2 units, 1 Cse5 unit, and 1 Cas6e unit, along with a crRNA (left panel), and a representative CRISPR Type I-E Cas3 that can be used in embodiments of this disclosure from *T. fusca*, (right panel), but Cas3 from other types of bacteria can be used. In embodiments, a Cascade complex may be used with or without a Cas3.

Figure 17:
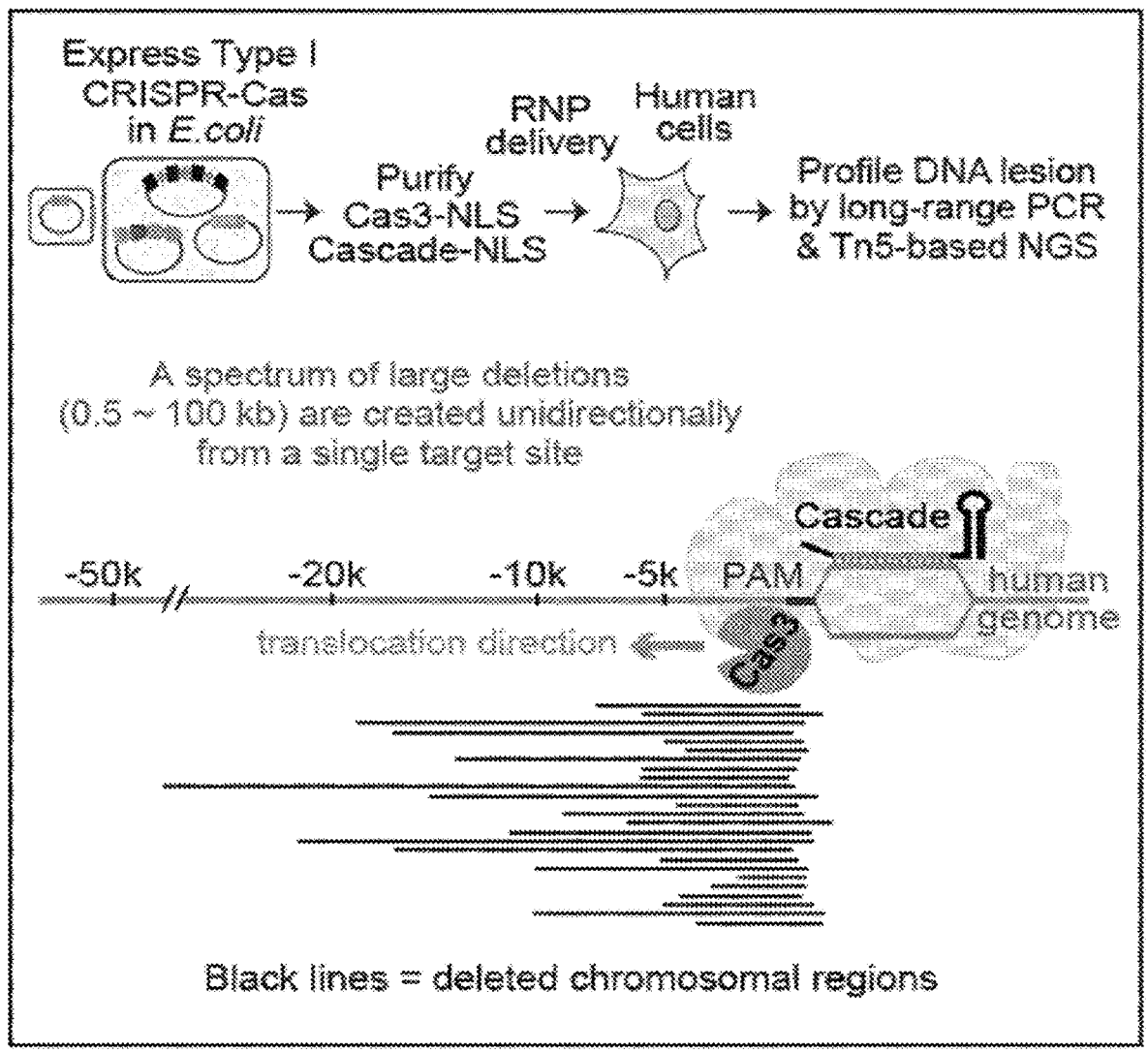
FIG. 17 provides an overview of a non-limiting embodiment of the disclosure using a ribonucleoprotein (RNP) delivery approach to create a spectrum of large deletions.

FIG. 17 provides an overview of a non-limiting embodiment of the disclosure using a ribonucleoprotein (RNP) delivery approach to create a spectrum of large deletions.

In embodiments, the disclosure provides for increased DNA editing, relative to a control value. In embodiments, the disclosure provides for increased editing that involves homology-directed repair (HDR).

In embodiments, the disclosure utilizes a Type I systems protospacer adjacent motifs (PAM) that comprises di- or tri-nucleotide conserved motifs downstream of protospacers opposite of the crRNA 5'-handle. Those skilled in the art will understand that other PAM sequences may be recognized by Cas enzymes from different bacterial types.

In embodiments, the disclosure can include a DNA molecule, such as an externally introduced DNA template, to repair the CRISPR-generated deletion, or other mutation. Thus, the disclosure includes introducing into a cell a DNA donor template, such as a single-stranded oligo DNA nucleotide (ssODN) repair template, that can yield intended nucleotide changes. Additional polynucleotides can be introduced for purposes such as creating an insertion, or a deletion of a segment of DNA in the cells. In embodiments, more than one DNA template is provided.

In embodiments, a Cascade and Cas3 used according to this disclosure generates one or more genome lesions, considered to be long-range deletions, wherein from the lesion(s) are initiated, or are located, from a few nucleotides from a suitable PAM sequence, and to up to 100 kb upstream of the PAM sequence.

In embodiments, the disclosure comprises one or a combination of: targeted mutagenesis by deleting one strand of DNA that is repaired by a ssDNA template via mismatch repair at the targeted site, wherein optionally the repair site is distant from the target site, wherein the distance may be up to 100,000 nts distant from the target site; recombination by engaging endogenous HDR machinery through the production of long 3' ends which are used as homology arms during repair for insertion of a donor; processing one end of DNA into a blunt end via another nuclease; use of a DNA-binding protein to block the processivity of Cas3 activity; using a combination of Cas3 that is deleted for nuclease activity and another Cas3 that is deleted for helicase activity, and performing the method at a temperature above ambient temperature, such as at about 37° C.

The disclosure comprises the modified cells, methods of making the cells, and cells that are mutated using the compositions and methods of this disclosure, and progeny of such cells, including but not limited to modified organisms which include and/or develop from such cells.

In embodiments one or more proteins used in this disclosure has/have between 50-100% identity to a wild type amino acid sequence. In embodiments, the protein comprises a truncation and/or deletion such that only a segment of the protein that is required to achieve a desired effect (i.e., an improvement in DNA editing/deletion relative to a reference) is achieved. In embodiments, a protein used herein comprises an amino acid sequence that includes additional amino acids at the N- or C-terminus, relative to a wild type sequence. Thus, in proteins used herein have an amino acid sequence described herein, and/or are encoded by any of the nucleotide sequences described herein, or any sequence having at least from 50%-100%, inclusive, and including all integers and ranges of integers there between, identity with the foregoing nucleotide and/or amino acid sequences. In embodiments, proteins have 90, 91, 92, 93, 94, 95, 96, 97, 98, or 99% identity across the entire length or a functional segment thereof of the sequences described herein. Thus, variants of the proteins and their nucleotide sequences are included. The term "variant" and its various grammatical forms as used herein refers to a nucleotide sequence or an amino acid sequence with substantial identity to a reference nucleotide sequence or reference amino acid sequence, respectively. The differences in the sequences may be the result of changes, either naturally or by design, in sequence or structure. Designed changes may be specifically designed and introduced into the sequence for specific purposes. Such specific changes may be made in vitro using a variety of mutagenesis techniques. Such sequence variants generated specifically may be referred to as "mutants" or "derivatives" of the original sequence. In a non-limiting embodiment, a system of this disclosure comprises an N23A mutation on Tfu_Cse2. See, for example, www.genome.jp/dbget-bin/www_bget?tfu: Tfu_1591, from which the amino acid sequence of the Cse2 protein is incorporated by references as of the effective filing date of this application or patent.

In embodiments, the disclosure comprises use of one or more *Thermobifida fusca* (*T. fusca*) proteins, or one or more proteins having at from 80-99% similarity to a *T. fusca* protein. In embodiments, the disclosure comprises use of (i) a combination of proteins comprising Cas3, Cse1/CasA, Cse2/CasB, Cas7/CasC, Cas5e/CasD and Cas6e/CasE, each comprising an amino acid sequence that is at least 85% homologous across its entire length to a *T. fusca* protein. In this regard, it is considered, without intending to be constrained by any particular theory, that use of *T. fusca* protein provides certain advantages that are not available using previously described systems. Comparisons of different representative distinct systems are summarized in Table A, wherein the criteria for numerals 1, 2, 3 and 4 are elaborated under the column "Cascade reconstitution & purification." The "-" symbol indicates a negative result.

TABLE A

| CRISPR Type | Species | Cascade reconstitution & purification | Cas3 purification & activity | Genome editing via RNP delivery in human cells | Genome editing profile defined by DNA sequencing |
|---|---|---|---|---|---|
| Type I-E | *T. fusca* | 1. Complex formation: Yes 2. PAM definition: Yes 3. R-loop formation: Yes 4. Cas3 recruitment: Yes | 1. Purification: Yes 2. Nuclease activity: Yes 3. Helicase activity: Yes 4. Cascade-dependent DNase: Yes | GFP K/O: up to 13% in human ES cells. Up to 96% in human HAP1 cells HPRT K/O: 67% in human HAP1 cells. | Sanger sequencing: up to 20 kb deletions. NGS sequencing: up to 100 kb deletions. Unidirectional, Upstream of PAM. Target site remains intact. |
| Type I-E | *E. coli* | 1: Y; 2: Y; 3: Y; 4: Y. | 1: Y; 2: Y; 3: Y; 4: Y. EcoCas3 is well | — | — |

TABLE A-continued

| CRISPR Type | Species | Cascade reconstitution & purification | Cas3 purification & activity | Genome editing via RNP delivery in human cells | Genome editing profile defined by DNA sequencing |
|---|---|---|---|---|---|
| | | | documented to aggregate, activity was inconsistent. One out of five preparations may have nuclease activity. | | |
| Type I-E | Streptymyces sp. SAT1 | — | 1: Y; 2: Y; 3: –; 4: –. | — | — |
| Type I-E | Salinispora arenicola | — | 1: N; 2: –; 3: –; 4: –. | — | — |
| Type I-E | Kitasatospora aureofaciens | — | 1: N; 2: –; 3: –; 4: –. | — | — |
| Type I-A | P. furiosus | 1: Y; 2: Y; 3: Y; 4: Y. PfuCascade prone to mis-assembly, activity low (Kd > 50 nM, 5-fold weaker than TfuCascade). | 1: Y; 2: Y; 3: Y; 4: Y. | Weak (0.05%) to undetectable editing activity. | — |
| Type I-C | B. halodurans | 1: Y; 2: Y; 3: Y; 4: Y. BhaCascade unstable, subunit dissociates easily. | 1: Y; 2: Y; 3: Y; 4: N. Cascade-dependent BhaCas3 activity not detectable. | — | — |

Thus, it is shown that the *T. fusca*-based systems of the present disclosure are superior to previous systems in terms of, for example, the percentage of cells in which DNA is modified, the length and position of the DNA modification, the unidirectional nature of the deletion which occurs upstream (i.e., 5') to the PAM site, and preservation of the target site. Preservation of the target site means that the segment of the DNA to which a segment of the crRNA binds is not modified.

In addition to the advantages of the presently provided systems described above, the present disclosure provides data demonstrating that the *T. fusca*-based systems can work at physiological temperatures characteristic of mammalian, and particularly human, body temperature. Thus, in embodiments, the disclosure provides for use of the systems described herein comprising *T. fusca* protein(s) wherein modifying DNA in eukaryotic cells is performed at a temperature that is higher than ambient temperature, ambient temperature being typically about 30° C. In embodiments, the disclosure provides for using the described systems at a temperature of about 37° C., although data presented herein shows the described systems can work at higher temperatures, such as up to 45° C. and 65° C. In embodiments, performing a method of the disclosure at a temperature of about 37° C. results in improved function, relative to performing the method of the at such a temperature with a system that does not include *T. fusca* protein(s). The term "about" 37° C. means the temperature may be from 36.0-38.0° C. In embodiments, the improved function comprises any one or a combination of the functions described in Table A.

In embodiments, the *T. fusca* proteins are as produced by, or derived from, any of the following organisms/sequences, as shown in Table B, and accordingly may include one or more proteins from *Thermobifida cellulosilytica*.

TABLE B

| | Description | Max score | Total score | Query cover | Per. Ident | Accession No. |
|---|---|---|---|---|---|---|
| Select seq pdb|4QQW|A | Chain A, Crispr-associated Helicase, Cas3 Family [*Thermobifida fusca* YX] | 1921 | 1921 | 100% | 100.00% | 4QQW_A |
| Select seq gb|AAZ55629.1| | CRISPR-associated helicase, Cas3 family [*Thermobifida fusca* YX] | 1920 | 1920 | 100% | 100.00% | AAZ55629.1 |
| Select seq ref|WP_081430412.1| | CRISPR-associated helicase/endonuclease Cas3 [*Thermobifida fusca*] | 1920 | 1920 | 100% | 99.89% | WP_081430412.1 |
| Select seq ref|WP_081638439.1| | CRISPR-associated helicase/endonuclease Cas3 [*Thermobifida fusca*] | 1914 | 1914 | 100% | 99.79% | WP_081638439.1 |

TABLE B-continued

| | Description | Max score | Total score | Query cover | Per. Ident | Accession No. |
|---|---|---|---|---|---|---|
| Select seq ref\|WP_082797692.1\| | CRISPR-associated helicase/endonuclease Cas3 [*Thermobifida fusca*] | 1915 | 1915 | 100% | 99.68% | WP_082797692.1 |
| Select seq ref\|WP_104613119.1\| | CRISPR-associated helicase/endonuclease Cas3 [*Thermobifida fusca*] | 1913 | 1913 | 100% | 99.68% | WP_104613119.1 |
| Select seq gb\|EOR71324.1\| | CRISPR-associated helicase Cas3 family protein [*Thermobifida fusca* TM51] | 1485 | 1485 | 78% | 99.59% | EOR71324.1 |
| Select seq gb\|PZN61028.1\| | CRISPR-associated helicase/endonuclease Cas3 [*Thermobifida fusca*] | 1912 | 1912 | 100% | 99.58% | PZN61028.1 |
| Select seq gb\|PPS91091.1\| | CRISPR-associated protein Cas3 [*Thermobifida fusca*] | 1887 | 1887 | 98% | 99.57% | PPS91091.1 |
| Select seq gb\|KUP97862.1\| | CRISPR-associated protein Cas3 [*Thermobifida cellulosilytica* TB100] | 1523 | 1523 | 98% | 80.75% | KUP97862.1 |
| Select seq ref\|WP_083948036.1\| | CRISPR-associated helicase/endonuclease Cas3 [*Thermobifida cellulosilytica*] | 1533 | 1533 | 100% | 80.11% | WP_083948036.1 |

In embodiments, the disclosure includes a crRNA, which may be considered a "targeting RNA". A crRNA, when transcribed from the portion of the CRISPR system encoding it, comprises at least a segment of RNA sequence that is identical to (with the exception of replacing T for U in the case of RNA) or complementary to (and thus "targets") a DNA sequence in a cell into which the system is introduced. In embodiments the targeting RNA is complementary to a sequence in a chromosome in a eukaryotic cell, or to a dsDNA extrachromosomal element, such as a dsDNA viral genome. Thus, the disclosure includes modifying chromosomes, and dsDNA extrachromosomal elements. The type of dsDNA extrachromosomal elements are not particularly limited. The dsDNA extrachromosomal element may be linear, or circular. In an embodiment, the extrachromosomal element is a viral dsDNA, and/or a cytoplasmic dsDNA that may or may not be from a virus.

Figure 6:
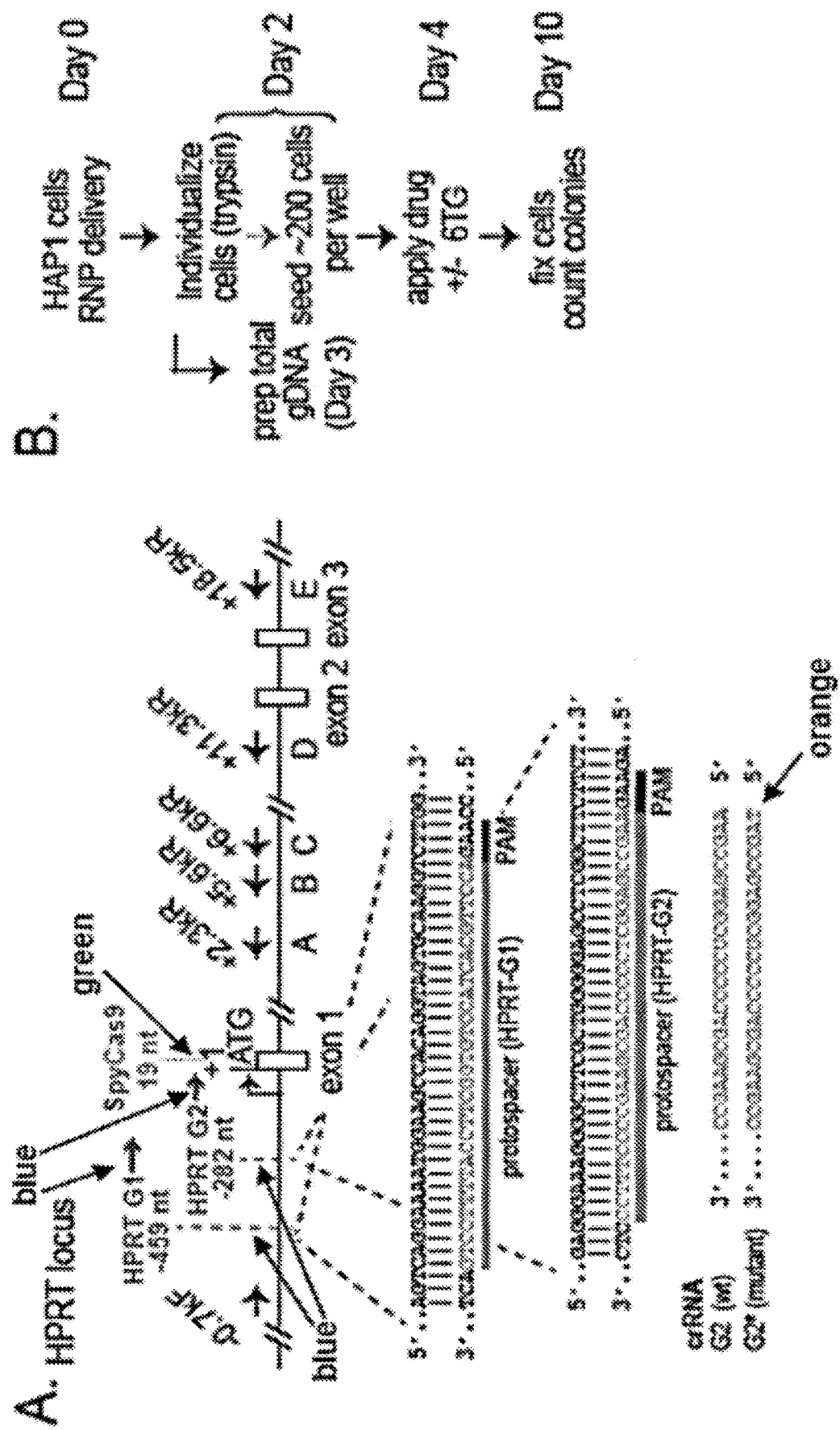
FIG. 6. Efficient editing at the endogenous HPRT locus in HAP1 cells. (A) Schematic of the HPRT locus and annealing sites for six PCR primers used in (E). Top strand sequence for HPRT (first double stranded DNA sequence): agtcag-gaaaatggaagccacaggtagtgcaaggtcttgg (SEQ ID NO:143); bottom strand sequence for HPRT (first double stranded DNA sequence): ccaagaccttgcactacctgtggcttccattttcctgact (SEQ ID NO:144). Top strand sequence for HPRT (second double stranded DNA sequence): gagg-gaaagggcttcgctggggagcctcggcttcttct (SEQ ID NO:145); bottom strand sequence for HPRT (second double stranded DNA sequence): agaagaagccgaggctcccccagcgaagccccttcctc (SEQ ID NO:146). Top strand sequence for crRNA G2 (top RNA sequence): aagccgaggcuccccagcgaagcc (SEQ ID NO:147); bottom strand for crRNA G2* mutant (bottom RNA sequence): tagccgaggcuccccagcgaagcc (SEQ ID NO:148). Protospacers for the two crRNAs are indicated as well as corresponding PAMs. Positions relative to HPRT translation start site (+1) are indicated. Recognition sites (2nd nt of the PAM) for HPRT G1 and G2 are marked by the dashed blue line. Blue arrowhead, direction of Cas3 translocation. Recognition site (1' Gin PAM) for the SpyCas9 is marked by the dashed green line. The G2 guide sequence is shown at the bottom, with the single nt mutation in HPRT-G2* in orange. (B) Procedure of the genome editing experiments in HAP1 cells. (C) Estimate HPRT targeting efficiency by single clone 6-TG cytotoxicity assay. (D) Bar graph plotting the HAP1 colony counts obtained in (C). The average 6-TG survival rates from three independent experiments are indicated. Error bar, standard deviation. (E) A collection of DNA lesions was induced in the HAP1 cells treated with Cas3 and Cascades HPRT-G1 or HPRT-G2, but not the HPRT-G2* mutant. PCR primers used are indicated and their annealing sites depicted in (A). M, DNA size markers. Lanes from two different agarose gels are separated by the dashed black line. (F) Locations of the HPRT genomic deletions. Black lines, deleted genomic regions. Orange (*), green (+), and the lack of dots on the right indicate Groups II, IV, and I deletion junctions as described in FIG. 4B.
Figure 6:
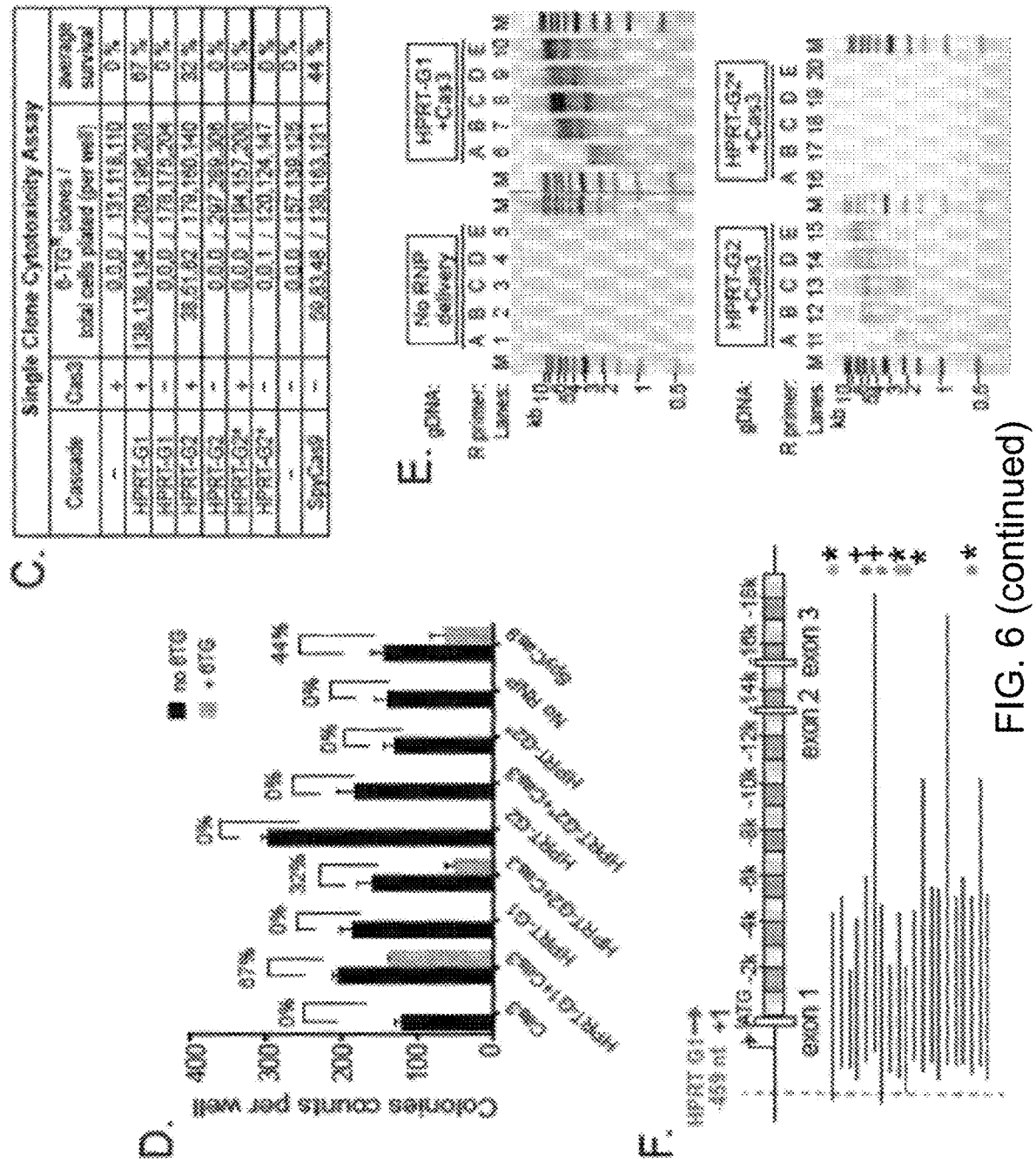

The sequence of the targeting RNA is not particularly limited, other than by the requirement for it to be directed to (i.e., having a segment that is the same as or complementarity to) a CRISPR site that is specific for a target in the cell(s) wherein a modification is to be made, and that it can function in a Cascade complex described herein, or as will otherwise be apparent to those skilled in the art. Non-limiting embodiments of DNA that comprises a targeted sequence are provided. For example, FIG. 6A illustrates a protospacer (which may be referred to herein as a "spacer") and shows the AAG PAM sequence in the bottom strand of the two dsDNA constructs. Suitable crRNA segments are shown below the two dsDNA strand examples. In embodiments, using a system described herein, the PAM and the protospacer sequence (the target sequence) is not modified. In embodiments, crRNA for a system according to this disclosure, such as a *T. fusca* system, is typically 61 nt long. The crRNA It has 32 nt spacer with an 8 nt and 21 nt rsequence at each end respectively.

In embodiments, the modification of genetic content in a cell using Type I CRISPR system described herein is improved relative to a reference. Improvement of the modification can include but is not necessarily limited to improved length of a deletion, or the amount of cells in which DNA modification takes place. Thus, in embodiments, the present disclosure provides for introducing a described Cascade system into a population of cells, wherein the DNA is modified in from 10%-100% of the cells in the population. In embodiments, between 1,000 to between one and three million cells are present in the population. In embodiments, between about 100,000 to about 300,000 cells are present in the population. In embodiments, at least 100,000 cells are present in the population. The amount, number, percentage, etc., of cells in which the DNA modification takes place can be determined using routine approaches, such as by DNA sequencing of the cells in the population.

In embodiments, the disclosure comprises deleting a segment of a chromosome. The deletion may be single or double stranded. In embodiments, the deletions comprise from 500 base pairs, to 100 K base pairs, inclusive, and including all ranges of numbers there between, and including base pair deletions.

In embodiments the disclosure comprises modifying a cell or a population of cells, such as eukaryotic cells by introducing into the cells one or a combination of expression vectors or other polynucleotides encoding a Cascade system.

In embodiments the disclosure may further comprise introducing into cells a DNA mutation template that is intended to be fully or partially inserted into a chromosome or other genetic element within a cell via operation of the present improved Type I CRISPR-Cas system. In embodiments the DNA mutation template comprises a DNA sequence that is homologous to a selected locus in a designated chromosome, and thus may be incorporated into a target genetic element via cooperation of the Type I CRISPR system and any type of homologous recombination. In embodiments the DNA mutation template can comprise a DNA segment having any nucleotide length and homology with a host cell genetic segment comprising a selected locus, so long as the length and sequence identity are adequate to introduce the intended genetic change into the locus via functioning of the Type I CRISPR-Cas system described herein. In embodiments, the DNA mutation template is a single-stranded oligo DNA nucleotide (ssODN). In embodiments, the DNA mutation template is a double-stranded (ds) template. In embodiments, the DNA mutation template is provided as an extrachromosomal element, such as a plasmid or PCR product. The DNA mutation template in certain aspects comprises a segment to be inserted into a chromosome. The segment can be inserted into a protein-coding or non-protein coding portion of a chromosome, or may be present in a regulatory control element, including but not necessarily limited to a promoter or enhancer element, a splice junction, etc.

In embodiments, the cells that are modified by the approaches of this disclosure are totipotent, pluripotent, multipotent, or oligopotent stem cells when the modification is made. In embodiments, the cells are neural stem cells. In embodiments, the cells are hematopoietic stem cells. In embodiments, the cells are leukocytes. In embodiments, the leukocytes are of a myeloid or lymphoid lineage. In embodiments, the cells are embryonic stem cells, or adult stem cells. In embodiments, the cells are epidermal stem cells or epithelial stem cells. In embodiments, the cells are cancer cells, or cancer stem cells. In embodiments, the cells are differentiated cells when the modification is made. In embodiments, the cells are human, or are non-human animal cells. In embodiments, the cells are mammalian cells. In one approach the cells are engineered to express a detectable or selectable marker or a combination thereof.

In embodiments, the disclosure includes obtaining cells from an individual, modifying the cells ex vivo using a Type I CRISPR system as described herein, and reintroducing the cells or their progeny into the individual for prophylaxis and/or therapy of a condition, disease or disorder, or to treat an injury, trauma or anatomical defect. In embodiments, the cells modified ex vivo as described herein are used autologously. In embodiments, the cells are provided as cell lines. In embodiments, the cells are engineered to produce a protein or other compound, and the cells themselves or the protein or compound they produce is used for prophylactic or therapeutic applications.

In various embodiments, the modification introduced into cells according to this disclosure is a homozygous dominant or homozygous recessive or heterozygous dominant or heterozygous recessive mutation correlated with a phenotype or condition, and is thus useful for modeling such phenotype or condition. In embodiments a modification causes a malignant cell to revert to a non-malignant phenotype.

In embodiments, kits for making genetic modifications as described herein are provided. A kit comprises one or more suitable vectors that encode Type I Cascade proteins. The kits can also include other components that are suitable for using the expression vectors to edit DNA in any cell type.

It will be recognized by those skilled in the art that a DNA CRISPR locus can comprise one or more repeats with or without the presence of regulatory elements intended to change transcription of the CRISPR locus. Guide RNAs can be artificially derived from sources such as in-vitro synthesis of RNA molecules, derived from DNA sequences encoding for an equivalent sequence, or from partially natural sources, such as recombinant expression from artificially-derived DNA sequences encoding for an equivalent sequence. There are a variety of publicly available resources that can be used to design suitable targeting RNAs, such as guide RNAs or crRNAs, which can be adapted for use with embodiments of the present disclosure. The guide RNAs can be complexed with Cascade proteins either at the same time as or at a separate time from the production of either the guide RNAs or the Cascade proteins. The guide RNA-containing Cascade Complexes can be either produced in a cell using DNA or RNA encoding for the protein and/or RNA components or delivered in the form of one or more vectors for expression or delivered in the form of RNA encoding for the proteins and/or RNA components or delivered in the form of fully-formed protein-RNA complexes through mechanisms including but not limited to electroporation, injection, or transfection. The guide RNA-containing Cascade complexes described herein, can be recombinantly expressed and purified through known purification technologies and methods either as whole Cascade complexes or as individual proteins. These proteins can be used in various delivery mechanisms including but not limited to electroporation, injection, or transfection for whole-protein delivery to eukaryotic organisms or can be used for in-vitro applications for sequence targeting of nucleic acid substrates or modification of substrates. Cascade complexes containing guides which target a DNA sequence of interest will hybridize to the target sequence and will, if complementarity is sufficient, open a full R-loop along the length of the target site. This Cascade-marked R-loop region adopts a conformation which allows Cas3 to bind to a site which is PAM-proximal, orienting the nuclease domain to initially attack the non-targeted DNA strand approximately 9-12 nucleotides inside the R-looped region. The helicase domain is loaded with the non-target strand, and the Cas3 then processively unwinds the substrate DNA in an ATP-dependent fashion from 3' to 5'. In conjunction with this helicase activity, nuclease activity cleaves the non-target strand in a processive fashion. The DNA sequence that is targeted is not particularly limited. In embodiments, an RNA coding sequence is targeted. In embodiments, an intron is targeted. In embodiments, a non-coding, non-intronic sequence is targeted. In embodiments, an essential gene is targeted, such that the modification of the essential gene may be lethal to the cell. In embodiments, more than one DNA sequence is targeted, such as by using multiple Cascade systems concurrently or sequentially, and/or by introducing more than one distinct creRNA.

In embodiments, the disclosure uses wild-type Cas3 proteins, or modifications or derivatives thereof. For example, in a case where either wild-type Cas3 or an otherwise engineered Cas3 is capable of cleaving both strands of DNA during a processive mode, once recruited to a validated target sequence by Cascade, Cas3 inherently produces a 3' overhang on the target strand. This is because Cascade is protecting the target strand from just after the PAM site to the end of the R-loop. Thus, once Cas3 is loaded on the non-target strand and begins its processive cleavage, the earliest nucleotide on the target strand that is available for cleavage is at the PAM site. In comparison, degradation of the non-target strand occurs 9-12 nucleotides inside the R-loop region. This introduced lesion can then be repaired with a provided donor nucleic acid template which is either single-stranded or double-stranded. The lesion can also be repaired in the absence of a donor template and due to the processive nature of Cas3 and multiple cleavage events introduced, drop-out of genomic DNA or a cross-over event can occur resulting in either production of a region deletion or in the production of a homozygous set of alleles which previously was heterozygous.

In a case where either wild-type Cas3 or an otherwise engineered Cas3 is capable of confining its cleavage activity to one or the other strand of substrate DNA, two or more Cascade targeting complexes can be used, such that the PAM sites are facing towards one another, to recruit Cas3 to each target site and degrade the intervening section of DNA on both strands. This will produce 3' overhangs on both strands of DNA and a degraded segment of DNA between.

In a case where either wild-type Cas3 or an otherwise engineered Cas3 is capable of confining its cleavage activity to one or the other strand of substrate DNA, an approach for replacing a strand of DNA with a donor ssDNA oligo can provide a means for targeted, precise, and predictable point mutation which is PAM independent.

In a case where helicase activity of Cas3 is decreased or destroyed, one or more Cascade targeting complexes can be used to recruit Cas3 to each target site and nick the non-target strand at each site. These nicks may be recognized by DNA repair proteins in the cell and repaired with a provided DNA donor which is either single-stranded or double-stranded.

Likewise, in a case where Cas3's helicase activity is decreased or destroyed (Helicase Dead, Nuclease Active or HDNA), and a separate protein with nuclease activity attenuated or destroyed (Helicase Active, Nuclease Dead or HAND), the substrate could be processed sequentially. In such a case, an HDNA Cas3 is recruited to one or more Cascade complexes at one or more target sites and produces a nick. Since helicase activity is required for further cleavage of the substrate, such an HDNA Cas3 would be unable to achieve any further modification of the substrate. If a HAND Cas3 is recruited to Cascade before an HDNA Cas3, it will be unable to perform any activity on the substrate DNA and will leave the binding site after some time. After initial nicking by an HDNA Cas3, HAND cas3 would bind and load the substrate DNA to the helicase, translocating along the substrate without nuclease activity. Without intending to be constrained by any particular theory, it is considered that Cas3's helicase is a translocase, and does not unwind DNA to produce two single-strands. If this is correct, the disclosure includes adding a ssDNA binding domain for HAND Cas3. This domain would bind the substrate DNA, and cause looping at the Cas3 helicase. This will place the substrate DNA out of register and decrease the likelihood of re-annealing to promote the formation of single stranded DNA.

As discussed above, variations on Cascade are encompassed in this disclosure. For example, Cascade complexes may be generated to contain a DNA guide instead of an RNA guide. Temperature-sensitive mutations may also be useful to either decrease the thermal requirement of activity for a thermophilic complex or to increase the thermal tolerance of a mesophilic complex. These mutations could affect protein stability, R-loop formation efficiency, expression or purification, off-target effects, or other complex functions or properties. Mutations to decrease the thermal dependence of T. fusca Cascade R-loop formation have been performed and analyzed in previous work. Epitopes, tags, and/or functional groups may be added to Cascade to aid in visualization, localization, or to confer new activity or other properties to the Cascade complex. It may be possible to generate hybrid Cascade complexes in which subunits from different organisms are used to form a single Cascade complex which may provide distinct advantages of individual sub-units from different organisms. It may be possible to engineer an interface on Cascade such that it interacts with the Cas3 protein of a different organism or with an engineered Cas3 protein.

The disclosure also includes using Cas3 variants and derivatives. For example, mutations can be made that affect protein stability, R-loop recruitment efficiency, initial nicking efficiency, helicase activity, processive nuclease activity, expression or purification, off-target effects, or other protein functions or properties. Temperature-sensitive mutations may also be useful to either decrease the thermal requirement of activity for a thermophilic protein or to increase the thermal tolerance of a mesophilic protein. Epitopes, tags, and/or functional groups may be added to Cas3 to aid in visualization, localization, or to confer new activity or other properties to Cas3. It may be possible to engineer an interface on Cas3 such that it interacts with the Cascade complex of a different organism or with an engineered Cascade complex.

Cascade complexes containing guides which target a nucleic acid sequence of interest can be tagged through protein fusion to any number of fluorescent proteins or groups for chemical modification and addition of fluorescent groups or some other functional unit that allows for detection, or by fusion to an antigen that allows for detection. The crRNA that is complexed with the Cascade protein may also be chemically modified to possess a chemical group that exhibits fluorescence or another method of detection. Additionally, Cas3 in either the wild-type, nuclease dead, helicase dead, or other mutant form or any combination thereof may be fused to any number of fluorescent proteins or groups for chemical modification and addition of fluorescent groups or some other functional unit that allows for detection, or by fusion to an antigen that allows for detection. Cas3 being tagged in such a way is expected to provide lower background detection signal when visualized optically due to Cas3 only being recruited to the site of a fully-formed Cascade R-loop constituting a properly recognized and validated target sequence. Epitopes, tags, or chemical groups added to Cascade, Cas3, or a crRNA can also be used as a mechanism for affinity purification. Hybridization of the crRNA to a target sequence prior to purification allows for a pull-down of sequences with significant complementarity to the crRNA and may be used to detect a sequence of interest or to infer the copy number of a sequence of interest through a method such as quantitative PCR.

The following examples are presented to illustrate the present disclosure. They are not intended to be limiting in any manner.

EXAMPLES

Design of T. fusca Type I-E CRISPR-Cas for Genome Editing in hESCs

Figure 7:
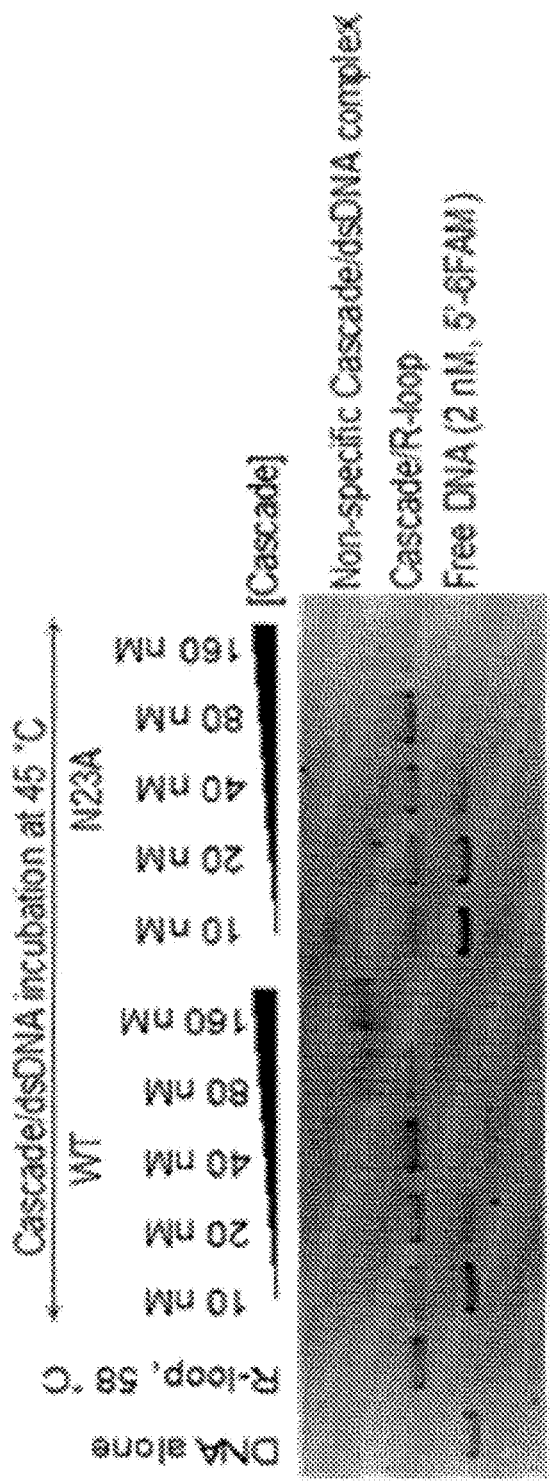
FIG. 7. Biochemistry on the *T. fusca* Type I-E CRISPR system. Related to FIG. 1. (A) R-loop formation behavior of WT and N23A mutant TfuCascade at 45° C. N23A interacts with dsDNA less non-specifically. (B) In comparison with WT, N23A mutant TfuCascade enables more efficient DNA nicking and degradation by TfuCas3 at 37° C. (C) NLS-tagged TfuCascade behaves similarly as the untagged version. (D) SDS-PAGE analysis of TfuCas3 and TfuCascade used in the genome editing experiments. TfuCascade was programmed with different guide RNAs, as referred in the text.
Figure 7:
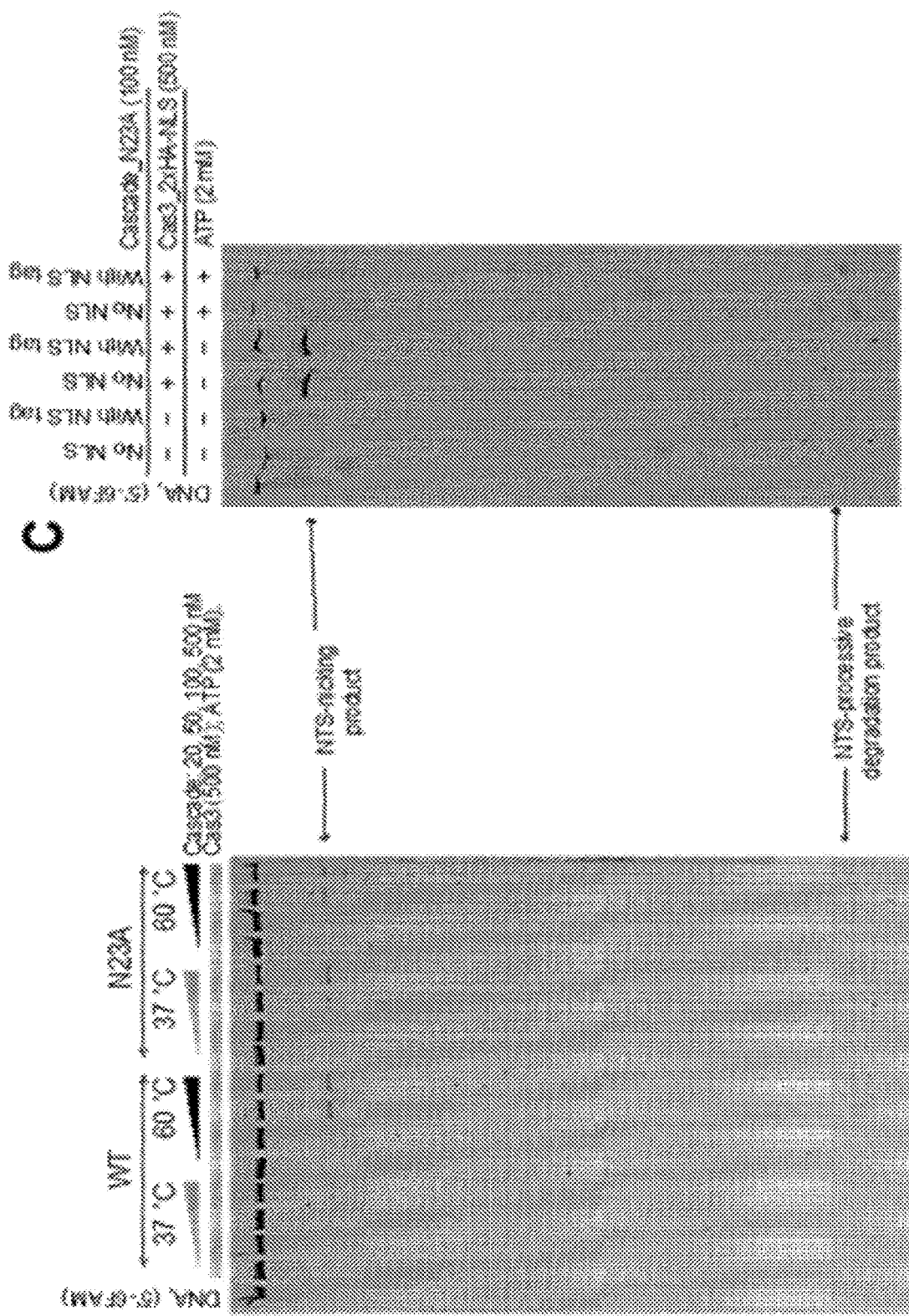
Figure 7:
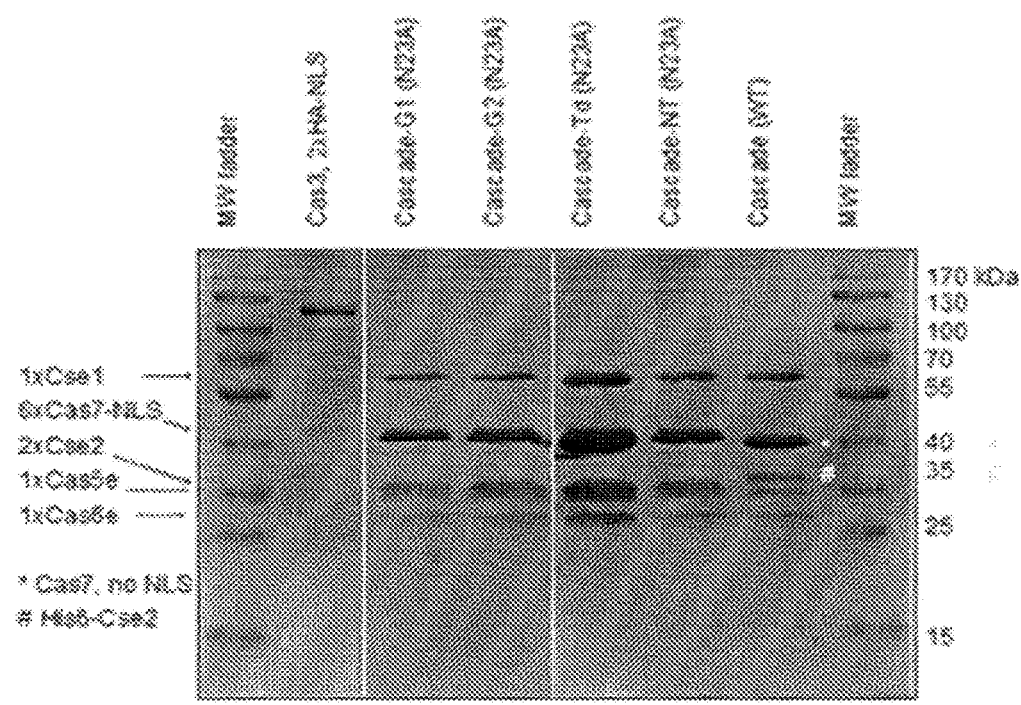

We chose the T. fusca Type I-E system to develop eukaryotic genome editing tools (FIG. 1A) for its clearly defined mechanisms and the highly active Cas3 nuclease. Several modifications were introduced to adapt this system for potential use in hESCs. First, the optimal growth temperature for T. fusca is 55° C. and R-loop formation by TfuCascade exhibits a strong temperature dependency (Xiao et al., 2017), which presents a potential technical hurdle for its adoption for mammalian use. Although robust in vivo interference activity was observed at 37° C. from T. fusca Type I-E CRISPR system functioning inside the E. coli cells (Huo et al., 2014), as a precaution, we screened a number of structure-guided mutations aimed at weakening the thermostability features of TfuCascade using in vitro approaches. TfuCascade bearing an N23A mutation in the Cse2 subunit (Xiao et al., 2017) was found to be more specific in DNA-binding and equally efficient in R-loop formation at mesothermic temperature (FIG. 7A). More importantly, this same mutant was more efficient in recruiting TfuCas3 for DNA nicking and degradation at 37° C. (FIG. 7B).

We decided to deliver this mutant version of TfuCascade and wild type TfuCas3 into hESCs via electroporation. RNP delivery was chosen over a plasmid-based expression method, partly to bypass the optimization steps needed for expressing and assembling a multi-subunit RNP complex in hESCs, and partly to avoid the possible off-target editing or cellular toxicity typically associated with long-term expression of CRISPR-Cas (Kim et al., 2014). Moreover, RNP delivery has been reported to be less stressful to hESCs (Kim et al., 2014). We attached nuclear localization signals (NLSs) to the C-terminus of TfuCas3 and the C-terminus of each of the six Cas7 subunits in TfuCascade to promote nuclear import. This NLS tagging scheme did not affect the stability of Cascade, nor its ability to target DNA for degradation in conjunction with Cas3 (FIG. 7C-D). To assay for genome editing activity (FIG. 1B), we created a hESC dual reporter line (H9-DNMT3B-tdTomato/EGFP) bearing knock-ins of a tandem dimer tomato fluorescent protein (tdTomato) gene and an enhanced green fluorescent protein (EGFP) gene at the two alleles of the highly expressed DNMT3B locus (FIG. 1C), leading to high levels of dual fluorescence. RNA-guided gene disruption of the EGFP reporter would lead to the accumulation of EGFP-negative/tdTomato-positive cells, and vice versa for the tdTomato gene disruption. Human ES cells were chosen for this disclosure over cancer-derived cell lines for their normal karyotype and DNA repair mechanisms.

Cascade and Cas3 Enable Programmable RNA-guided Gene Disruption in hESCs

We first programmed TfuCascade with a 61-nt crRNA containing guide sequence G1 against a 32 base pair (bp) region in EGFP that was flanked by an interference-enabling PAM 5'-AAG (FIG. 1C), purified this TfuCascade-G1 RNP, and electroporated it together with TfuCas3 into the hESC dual-reporter line. A sub-population (7.3%) of EGFP-negative and tdTomato-positive cells became detectable by flow cytometry after 4-5 days (FIG. 1D). Negligible levels of EGFP-negative/tdTomato-positive cells were detected in control transfections that included TfuCascade-G1 alone, or TfuCas3 alone, or a non-targeting (NT) TfuCascade together with TfuCas3 (FIG. 1D). A very small fraction of cells lacking both EGFP and tdTomato fluorescence were observed for each reaction, even when no CRISPR components were delivered. This was most likely caused by spontaneous hESC differentiation that leads to rapid repression of the DNMT3B locus (Sperger et al., 2003), which results in the simultaneous loss of both EGFP and tdTomato expression in the presently used reporter line. No apparent cell toxicity was observed for any combination of Cas3 and/or Cascade delivery. Collectively, these results suggest that the *T. fusca* Type I-E CRISPR-Cas system can induce RNA-guided gene disruption in hESCs, and that both the nuclease-helicase effector Cas3 and a cognate Cascade are required.

To demonstrate that the editing is programmable, we designed two additional TfuCascade RNPs. Co-delivery of a TfuCascade-G2 targeting the opposite strand of EGFP (FIG. 1C) together with TfuCas3 lead to the accumulation of 2.7% EGFP-negative and tdTomato-positive cells (FIG. 1E). Moreover, electroporation of a tdTomato-targeting (Td) TfuCascade (FIG. 1C) in conjunction with TfuCas3 resulted in a 2.7% tdTomato-negative and EGFP-positive cell population (FIG. 1F). These results further demonstrated that this Type I CRISPR-based novel gene editing platform is re-programmable.

Figure 8:
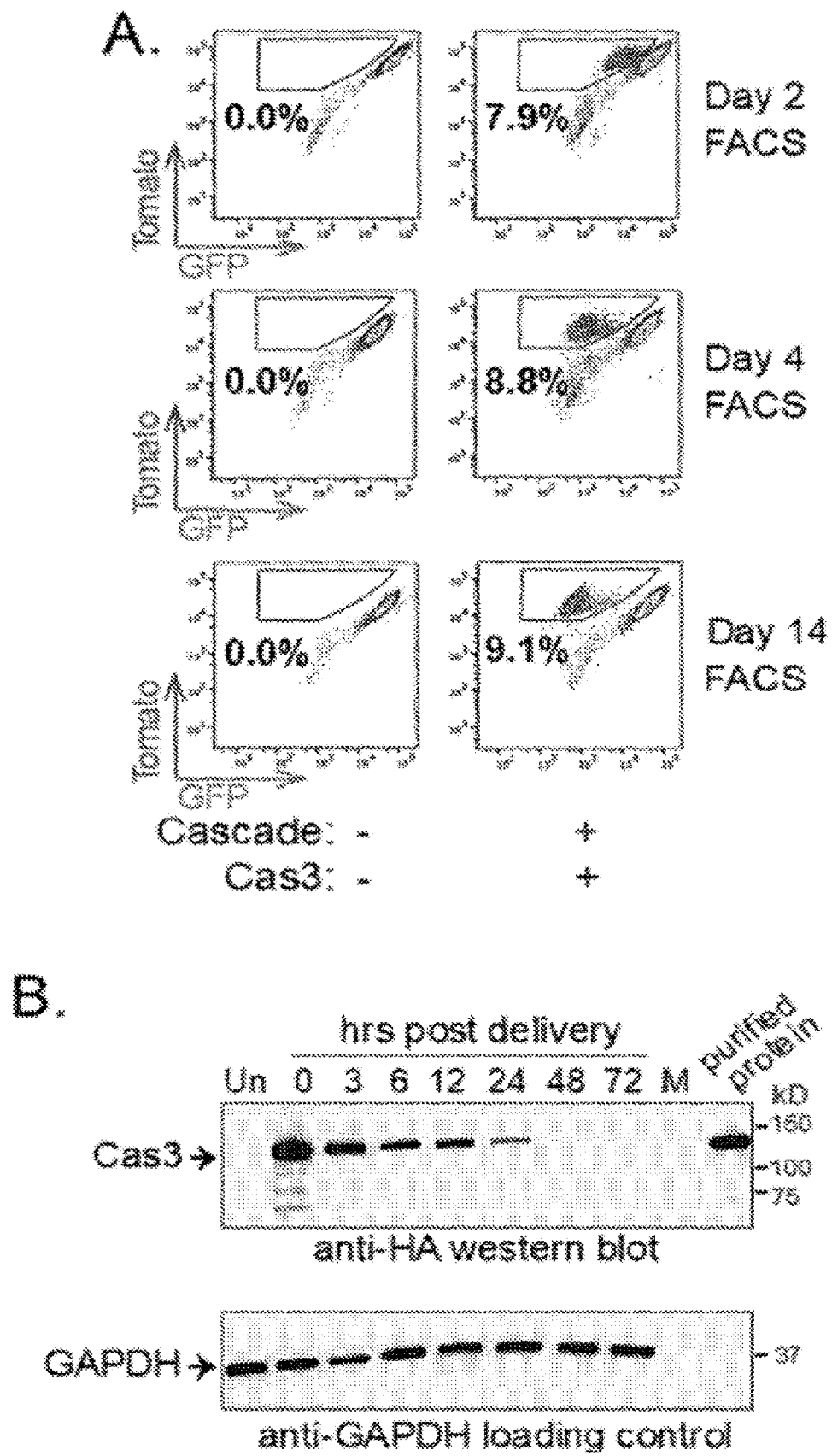
FIG. 8. Type I CRISPR-mediated GFP disruption is not due to transient transcriptional repression. Related to FIG. 1. (A) H9-DNMT3B-EGFP-tdTomato dual-reporter hESCs were analyzed by flow cytometry 2, 4 and 14 days after electroporation with Cas3 and Cascade-G1 RNP. The percentages of GFP-negative/tdTomato-positive cells (boxed) were indicated. (B) H9-DNMT3B-EGFP-tdTomato dual-reporter hESCs were collected at the indicated time points after electroporation with Cas3 and Cascade-G1 RNP, and the abundance of Cas3 that remained in the cells was analyzed by western blot using anit-HA antibody. GAPDH serves as internal loading control. Purified Cas3 protein is the positive control. Un, un-transfected cells; M, DNA size markers.

Since Cascade alone has been shown to silence the targeted gene in bacteria by sterically blocking transcription (Luo et al., 2015; Rath et al., 2015), we felt compelled to distinguish whether the silencing mechanism was due to DNA editing or transcriptional repression. Several lines of evidence argue that the loss of EGFP fluorescence in the present experiment was not due to Cascade-mediated transcriptional silencing. First, hESCs that received Cascade-G1 RNP alone exhibited zero EGFP-negative/tdTomato-positive events (FIG. 1D), suggesting that the DNA degradation factor Cas3 is indispensable for GFP silencing. Second, editing at the DNA level would persist through generations, whereas transcriptional effects enabled by RNP delivery would be titrated away as cells divide. When we cultured the Cascade-G1/Cas3 treated cells continuously and retrieved samples on days 2, 4 and 14 post RNP delivery for flow cytometry analysis, a 7.9% EGFP-negative/tdTomato-positive sub-population appeared within two days and remained at ~9% on days 4 and 14 (FIG. 8A). The background EGFP intensity in the EGFP−/tdTomato+ cells further diminished with extended culturing, probably because the existing EGFP proteins degraded over time (FIG. 8A). These observations again are consistent with permanent DNA changes rather than transient transcriptional suppression. Lastly, we monitored Cas protein stability in hESCs after RNP delivery using western blot. The vast majority of HA-tagged TfuCas3 was degraded rapidly within the first 24 hrs (FIG. 8B), which is on par with the reported persistence time of Cas9-sgRNA RNP in human cells (Kim et al., 2014). Although an antibody was not in hand to track Cascade stability, there was no reason to suspect that Cascade-caused transcriptional blockage, if any, would still persist after 14 days of cell growth and divisions.

Editing Efficiency is Limited by the Activity of Cascade, but not Cas3

We attempted to optimize this editing platform by varying the amount of Cascade and Cas3 delivered. The efficiency of EGFP disruption positively correlated with TfuCascade abundance, increasing from 3.3% to 13.1% when the amount of TfuCascade-G1 RNP delivered via a 10 μL electroporation reaction was increased from 20 to 80 pmole, with TfuCas3 kept constant at 20 pmole (FIG. 2A). A similar correlation was observed between the amount of electroporated TfuCascade-G2 RNP and the editing efficiency (FIG. 2B). In contrast, doubling, tripling, or quadrupling the amount of TfuCas3 while keeping Cascade constant did not improve the editing efficiency (FIG. 2C). These findings suggest that the editing efficiency in hESCs might be currently limited by the target-searching activity or the chemical stability of TfuCascade, rather than DNA degradation by TfuCas3.

Type I CRISPR-Cas Editing Induces a Spectrum of Large Chromosomal Deletions

We analyzed whether chromosomal deletions may be induced upstream (i.e. PAM-proximal direction) of the target site. To understand the genomic lesions that underlie EGFP disruption, we extracted genomic DNA from the TfuCascade-G1/Cas3 edited hESCs before and after fluorescence activated cell sorting (FACS), and PCR-amplified a ~5.1 kb region using two primers spanning a region 4.7 kb upstream and 400 bp downstream of the target site (FIG. 3A, −4.4 kF and R1). The untransfected cells and the TfuCascade-NT/Cas3 treated cells served as two controls, and both produced a single PCR band of 5.1 kb, suggesting that the DNMT3B-EGFP locus was intact (FIG. 3B, lanes 1-2). The amplicons from the unsorted total cells after the TfuCascade-G1/Cas3 treatment contained a faint ladder of smaller bands in addition to the full-length product, indicating that a fraction of these cells harbor deletions of varying lengths at the DNMT3B-EGFP locus (FIG. 3B, lane 3). Notably, PCR amplifications from the sorted EGFP-negative/tdTomato-positive population were highly enriched with a distribution of smaller products, ranging from 5 kb to ~1 kb in size. The lack of a discernible full-length product (~5.1 kb) also implies that small indel-mediated EGFP disruption was rare during Type I CRISPR editing (FIG. 3B, lane 4). Speculating that some deletions might extend beyond the 4.7 kb detection limit, we repeated the experiment using a different forward primer annealing further upstream of the target site (FIG. 3A, −8.2 kF). The resulting PCR band pattern indeed suggests that the chromosomal deletions were well-represented all the way up to ~7.5 kb (FIG. 3B, lanes 5-8). Control PCRs amplifying a 5.5 kb region downstream of EGFP detected no genomic deletions (FIG. 3B, lanes 9-12), in agreement with the idea that Cas3 is a highly processive helicase-nuclease that translocates uni-directionally towards the PAM-proximal direction. The observed lesion profile for Cascade/Cas3 is in stark contrast to that of eukaryotic gene editing by the Cas9 or Cas12 nucleases, which typically lead to small indels at the target site.

Because the DNA lesion pattern could not be comprehensively captured in any single PCR reaction, we performed a series of long-range PCRs using a common reverse primer annealing 2 kb downstream, paired up with one of the nine forward primers tiling along a 22 kb region upstream of the EGFP targeted site (FIG. 3C, +2.3 kR and nine tiling primers A through I). FACS-sorted, Cascade-G1/Cas3-edited cells from six independent experiments were pooled together, and nine individual PCR amplifications from this "pooled" genomic DNA all gave rise to a collection of smaller products of varying sizes (FIG. 3D, lanes 1-9), indicating that heterologous large deletions were induced across the 22 kb upstream region. Control PCR amplifications using the same nine primer pairs on untransfected cells (FIG. 3D, right) generated either the expected full-length product (lanes 10-13), discrete non-specific bands (lanes 11-12 and 14-17), or no product (lane 18).

Figure 9:
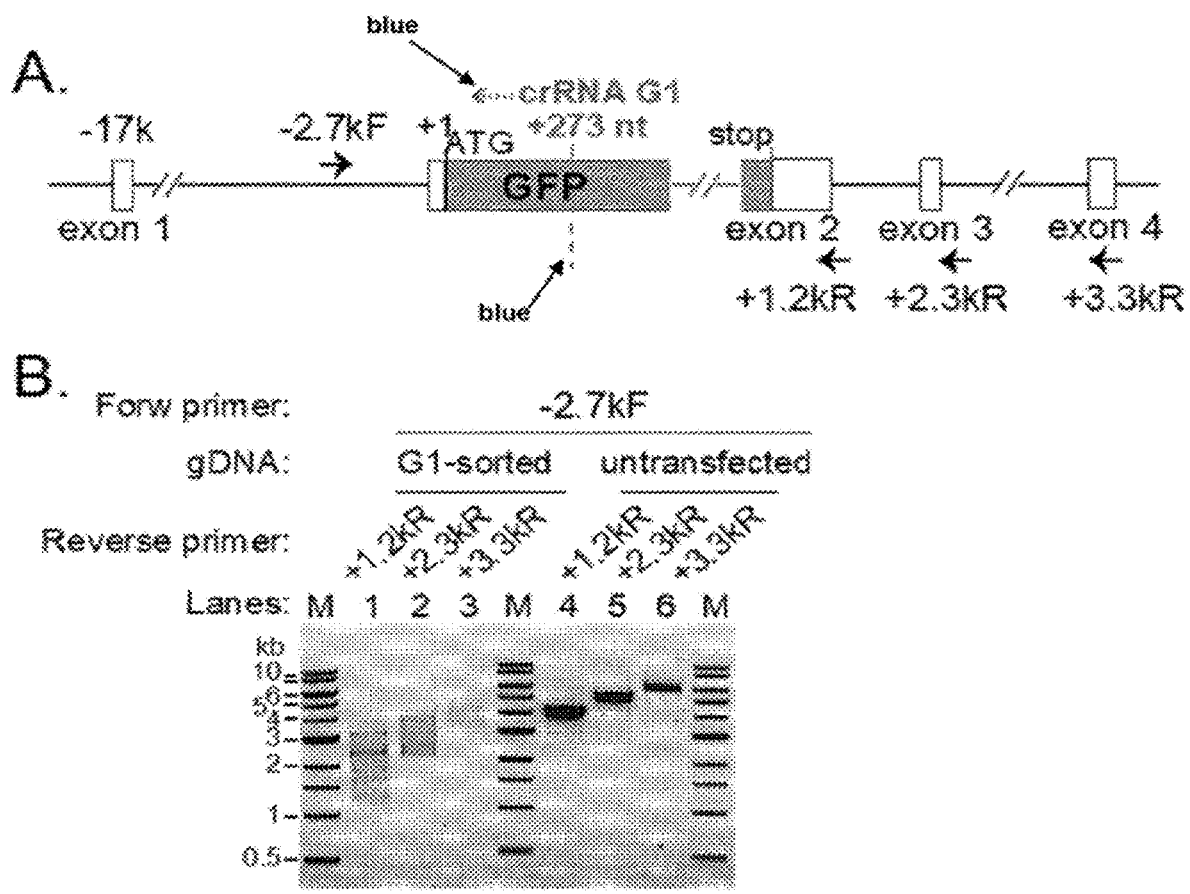
FIG. 9. Long-range PCR characterization of genomic lesions induced by Type I CRISPR-Cas. Related to FIG. 3. (A) Schematic of the EGFP reporter at DNMT3B locus and annealing sites for four PCR primers used in (B). Positions relative to the EGFP translation start site (+1) are indicated. Recognition site for Cascade G1 is marked by the dashed blue line. Blue arrowhead, direction of Cas3 translocation. (B) Long-range PCR based genomic lesion characterization. A spectrum of chromosomal lesions was introduced upstream of EGFP by Cascade-G1 and Cas3 in the sorted EGFP-negative population. Genomic DNA from un-transfected WT cells serves as controls. PCR primers used are indicated and their annealing sites depicted in (A). M, DNA size markers. Note that the minimum amplicon size in lanes 1-3 varied in accordance with the distance between the target site and the annealing position for the reverse primer used.

A recent study showed that in addition to the desired small indels, CRISPR-Cas9 may also cause rare complex distal deletions (kilobases in size) in mouse embryonic stem cells (mESCs) (Kosicki et al., 2018), and the observed deletions could be bi-directional from the Cas9 cut site, which is distinct from the uni-directional deletion pattern observed for Type I editing events (FIGS. 3A-B). We further investigated whether deletion events spanning both PAM-proximal and PAM-distal regions may exist among the edited human cells, due to Type I-editing induced genome instability. First, we noticed that the smallest PCR products in lanes 1 through 9 of FIG. 3D were all around or slightly above 2 kb, which matches the genomic distance between the targeting site and the annealing site of the common downstream primer. This suggests that the deletion events did not extend to the PAM-distal (downstream) region. Secondly, we performed additional PCRs using a common forward primer (−2.7 kF) but varying the reverse primer annealing site to be ~0.9 kb, 2.0 kb, or 3.0 kb 3' of the target site (FIG. 9A). The minimum amplicon size in each reaction varied in accordance with the distance between the target site and the annealing position for the reverse primer used (FIG. 9B, lanes 1-3). These observations together suggest that the present Type I editing demonstrations rarely led to complex bi-directional deletion events spanning the target site, as seen in the Cas9 study (Kosicki et al., 2018).

An Unusual Pattern of Type I CRISPR-Mediated Genomic Lesions

To map out the precise boundaries of the Cascade-G1/Cas3-induced deletions, we first employed a Sanger sequencing based low-throughput method that can reveal DNA lesions at single-nucleotide resolution. The amplicons from lanes 1 through 9 in FIG. 3D were pooled and TOPO-cloned. Two hundred and eleven positive clones were randomly chosen for Sanger sequencing using the GFP reverse primer R1 to identify the chromosomal junctions; an additional fifteen random clones from the TOPO-cloned PCR products from lanes 4 or 8 of FIG. 3B were also sequenced. 215 out of the 226 sequenced clones yielded good quality sequencing trace. A total of 180 unique chromosomal lesions were identified, and they can be categorized into four major groups based on the features of their junctions (FIGS. 4B, 4D-E and 10, a complete list in Table 2). Group I is the most prevalent, consisting of 140 cases (78% of 180) where the 5' and 3' regions flanking the deletions were re-ligated seamlessly, presumably via the NHEJ pathway in human cells. This finding suggests that the *T. fusca* Type I CRISPR-Cas likely induced at least two DSBs in the upstream region; more DSBs possibly occurred in between but were masked by the terminal DSBs. We were not able to distinguish if any small deletions were further generated at the junction during NHEJ repair, because the precise locations of the DSBs and the nature of the resulting DNA ends (blunt or recessive) are unclear.

Group II contains 25 cases (14% of 180) of a single large deletion combined with a short insertion at the repair junction (FIGS. 4B, 4D-E, 10, and Table 2). Among them, fifteen deletions were associated with a small insertion less than 18 bp; while ten deletions were associated an insertion of a few hundred bp (seven of which could be mapped back to part of the deleted genomic sequence in reverse orientation. i.e. inverted). Group III only has 4 examples containing a large deletion combined with a point mutation near the junction (FIGS. 4B, 4D-E, 10, and Table 2). Groups II and III products are presumably formed by the mutagenic NHEJ repair pathway(s).

Interestingly, eleven group IV cases exist, each contains two large deletions separated by an intervening chromosomal sequence of a few hundred base pairs (FIGS. 4B, 4D-E, 10, and Table 2). One potential cause of the group IV events may be the re-insertion of a segment of the originally deleted genome during the repair of one large deletion, and it is possible that the re-inserted segments are Cas3-generated dsDNA fragments. Notably, for 95% of all unique lesions (171/180), the Cascade recognition site and its flanking PAM remained intact after editing and repair (FIG. 4A, and Table 2), and in theory might be able to support additional rounds of editing if free Cascade and Cas3 are available. Therefore, we cannot rule out the possibility that group IV events resulted from two successive rounds of editing events.

The 5' deletion boundaries, which likely reflect the last DSB generated by Cas3 before its dissociation from DNA, are distributed across the ~20 kb upstream region, highlighting the heterogeneous nature of the long-range lesions induced by Cas3 and a single-CRISPR-programmed Cascade. An unexpected finding was that the 3' boundaries of these deletions, which possibly represent the first DSB by Cas3, did not line up precisely with Cas3's first nicking site, which is 9-11 nt after the PAM, into the R-loop (or protospacer) region (Xiao et al., 2017). Instead, they spread out along a ~400 bp window upstream of the target site, which included the first ~300 bp of EGFP coding sequence and the preceding 100 bp sequence in the upstream intron (FIGS. 4A and 4C). More editing events may have started further upstream, but would not be enriched by cell sorting if the deletions were limited to the intronic region and did not affect EGFP expression. This observation suggests that Cas3 does not necessarily elicit DSBs during the very initial phase of its DNA translocation. Previous single molecule studies revealed that after recruitment by Cascade, Cas3 nicks the non-target strand DNA, then initially remains associated with Cascade and reels dsDNA towards itself repeatedly, and eventually dissociates from Cascade and translocates alone for kilobases along the DNA (Dillard et al., 2018); in both phases NTS DNA was sporadically erased, leading to the exposure of short TS single-stranded DNA (ssDNA) tracts (Dillard et al., 2018; Redding et al., 2015). DSB formation was not frequently observed at the single molecule level (Dillard et al., 2018; Redding et al., 2015). However, dsDNA targets were found to be shredded by Cas3 into pieces in bulk biochemical experiments (Dillard et al., 2018; Kunne et al., 2016; Redding et al., 2015).

To define the genome lesion at single cell level, we isolated fifteen single cell clones from the sorted GFP-negative cells from the Cascade G1/Cas3 editing experiment in FIG. 1D. All clones appear healthy. Their genomic DNAs were subjected to the tiling PCR and Sanger sequencing analysis described in FIGS. 3D and 4A, to identify potential lesions within the 20 kb PAM-proximal DNMT3B region. Nine clones each contains an identifiable, unique long-range deletion (listed in Table 2); it is unclear what kind of DNA lesions exist for the other six clones.

Heterogeneous Large Deletions Introduced on a Second Chromosomal Target Site.

To understand if the formation of a spectrum of large deletions is a generalized feature for Type I CRISPR editing, we did lesion analysis for another target site on the opposite strand of EGFP specified by Cascade-G2 (FIG. 1C). Because Cas3 was oriented by Cascade-G2 to translocate in the opposite direction as Cascade-G1, we anticipated that chromosomal deletions would occur downstream of GFP accordingly. We extracted genomic DNA from the sorted EGFP-negative/tdTomato-positive cells from the experiment in FIG. 1E and PCR-amplified a 6.5 kb region using primers bracketing the EGFP coding sequence and 4.9 kb downstream of GFP (FIG. 11A, F and +6.5 KR). As expected, a spectrum of PCR products smaller than 6.5 kb was amplified from the sorted cells; whereas two negative control PCRs from untransfected cells or TfuCascade-NT/Cas3 treated cells both produced a single 6.5 kb band (FIG. 11B, lanes 1-3). A similar pattern was observed when the PCR was repeated using a reverse primer annealing 3.5 kb further downstream; while control PCRs amplifying a 4.4 kb region upstream of the target revealed no genomic lesions (FIGS. 11A, 11B, lanes 4-9).

We TOPO-cloned the amplicons in lanes 3 or 6 of FIG. 11B, and randomly picked 53 clones for Sanger sequencing. 26 unique lesion events were identified, among which 22 were seamless junctions (Group I), one was a deletion plus a 2 bp small insertion (Group II), one was a deletion with a point mutation 3 bp nearby (Group III), and two had double deletion junctions (Group IV) (FIGS. 11C-D, a complete list in Table 2). The 5' deletion boundaries here, likely reflecting the first DSB by Cas3, spread out in a ~390 bp window right after the target site; and the recognition site for Cascade-G2 remained intact for all the 22 lesion cases. The 3' endpoints of lesions, which possibly represent the last DSB by Cas3, were distributed across a 9.7 kb region downstream of the target site (FIG. 11C). Collectively, these results further demonstrated that Type I CRISPR-Cas could be reprogrammed to induce a spectrum of large deletions on the PAM-proximal side of a single CRISPR-targeted site.

Comprehensive Lesion Analysis by Tn5-Based Next-Generation Sequencing (NGS)

To define Type I CRISPR-induced lesions more comprehensively, we developed a Tn5 tagmentation and NGS based method (FIG. 5A). The genomic DNAs of FACS-sorted, Cascade-G1/Cas3 edited EGFP−/tdTomato+hESCs from six independent experiments were pooled together and treated with adapter-loaded Tn5 transposase, which randomly fragments DNA and attaches a single type of adapter onto the fragmented ends. We then did a multi-step PCR using nested EGFP primers and a primer specific for the Tn5 adapter to enrich for sequences spanning the lesion junctions (FIG. 5A). The resulting NGS library was sequenced on an Illumina MiSeq using 50×450 bp paired end sequencing, and the long R2 reads were analyzed to determine the extent of the corresponding deletions, as described in Methods. Since 97% (174/180) of all unique lesions detected by Sanger sequencing in FIG. 4 started within ~330 bp from the Cascade binding site, we analyzed whether we could cover most of the junctions using the 450 bp MiSeq reads from the EGFP-specific primer used for library construction. Bioinformatic analysis of the NGS dataset detected DNA lesions in 33.2% of the 278,074 aligned MiSeq reads obtained, and identified roughly 3,376 unique junctions (it is unclear whether the repeated instances of identical junctions reflect PCR duplicates or genuine repeated biological events). Out of the total set of reads, 95.3% of the reads have at least 95% of their length aligned to the ~130 kb region consisting of the DNMT3B-GFP locus and its upstream sequence. The remainder (4.7%) could represent either sequencing errors, cases where insertions were drawn from other portions of the genome, or deletions too large to be identified in the reference sequence—we excluded all such reads from further consideration. Among the considered set of lesion reads, consistent with Sanger sequencing results, the vast majority (86%) contain Group I events, with one junction between the 5' and 3' flanking regions of a large chromosomal deletion (FIG. 5B). Their 3' deletion endpoints occur within a ~400 bp window upstream of the targeted EGFP sequence, whereas the locations of the 5' endpoints are far more spread out and can be tens of kilobases upstream (FIG. 5C). The sizes of these Type I-E CRISPR-induced Group I deletions are concentrated within a 30 kb range, however, a portion of deletions exists even above 50 kb (FIG. 5D). In roughly 12% of the considered set of lesion reads, we observed an inverted segment of the human DNMT3B locus forming a junction with what is presumably the 3' endpoint of a Cas3-induced deletion. Due to the sequencing length limitation, we cannot see the deletion's 5' breakpoint, but nonetheless still classified these events into Group II lesions (a deletion with an insertion, in this case inverted) (FIG. 5B). Finally, 2% of the considered lesion reads contain Group IV cases with two large deletions (FIG. 5B). We have also observed that a portion of the analyzed reads appear to have small un-mappable insertions between the two alignable ends of the deletion junction. Due to NGS sequencing error rates and the possibility of minor alignment error, we decided to not call point mutations or small insertions less than 10 bp at the repair junctions, and all such reads were classified into Group I lesions in FIG. 5B. Deletion junctions with an un-mappable insertion larger than 9 bp only account for <2% of all the lesion reads, and are classified into Group I or II events.

Highly Efficient Targeting of the Endogenous HPRT Locus in HAP1 Cells

Figure 12:
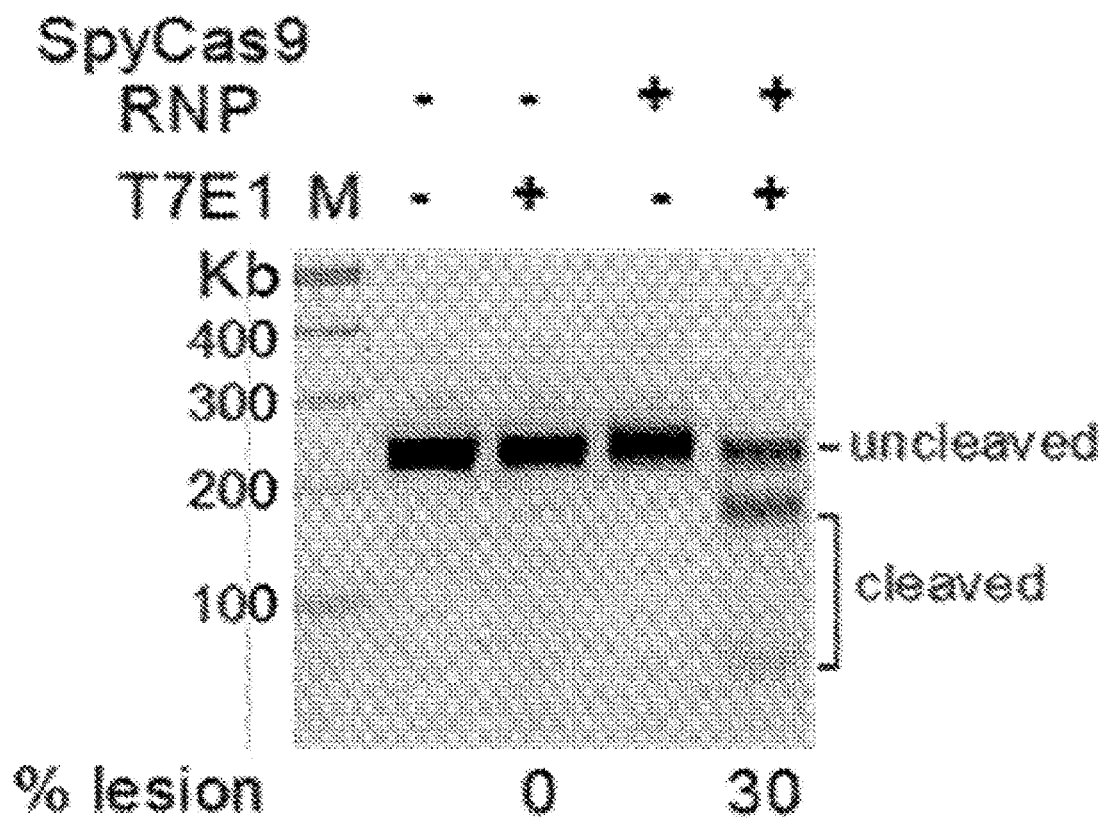
FIG. 12. Estimate indel formation rates for the HPRT-targeting SpyCas9 using TIDE and T7E1 assays. Related to FIG. 6. T7E1 analysis of editing efficiency at the same SpyCas9-targeted HPRT site, for HAP1 cells that received SpyCas9 RNP or no treatment. Input and cleaved products are indicated. Calculated lesion efficiencies were shown at the bottom. M, DNA size markers.

To test if Type I CRISPR can be exploited to engineer an endogenous locus in a different cell line, we programmed Cascade with two crRNAs targeting the promoter region ~280 or ~460 nt upstream of the HPRT gene (HPRT-G1 and HPRT-G2, FIG. 6A), and tested them in the near-haploid chronic myeloid leukemia derived cell line HAP1. Genomic deletions caused by CRISPR targeting and Cas3 translocation towards the coding sequence would disrupt HPRT production, leading to resistance to 6-thioguanine (6-TG). After RNP delivery, we estimated the editing efficiency by comparing the single cell colony forming capability in the presence or absence of 6-TG in the culture media (FIG. 6B). When co-delivered with Cas3, Cascade HPRT-G1 or HPRT-G2 enabled 67% and 32% targeting, respectively (FIGS. 6C-D). Importantly, a single nucleotide mutation introduced at the beginning of the crRNA spacer (HPRT-G2*, FIG. 6A) prevented editing (FIGS. 6C-D), suggesting that genome targeting by the Tfu Type I-E CRISPR is stringent. For comparison, a SpyCas9 RNP recognizing a site within HPRT exon 1 exhibited 44% editing in the single clone 6-TG cytotoxicity assay (FIGS. 6A, 6C-D), consistent with the indel formation rates assessed using the tracking of indels by decomposition (TIDE) analysis (Brinkman et al., 2014) and T7E1 assay (Guschin et al., 2010) (FIG. 12).

Genomic lesions caused by HPRT-G1/Cas3 and HPRT-G2/Cas3 were characterized by long-range PCRs using a forward primer and one of the reverse primers tiling along the HPRT locus (FIG. 6A). Wild type genomic DNA failed to produce amplicons, possibly because a GC-rich region in exon 1 prevented PCR amplification; whereas the genomic DNA from the edited cells produced heterogeneous deletions, evidenced by the ladder of smaller PCR products (FIG. 6E). Consistent with the 6-TG cytotoxicity results, HPRT-G2* mutant failed to induce DNA lesions because no amplicons were produced (FIG. 6E). Next, we pooled amplicons from lanes 6-10 of FIG. 6E for TOPO-cloning and picked 20 clones for Sanger sequencing. Each clone revealed a unique uni-directional DNA lesion, and Group I, II and IV deletions/junctions events were all observed (FIG. 6F), suggesting that the editing pattern by Type I CRISPR is likely not cell type- or locus-specific.

EXPERIMENTAL MODELS AND SUBJECT DETAILS

*Escherichia coli* BL21 (DE3). *E. coli* BL21 (DE3) cells were used for protein production. Cells were grown in Lysogeny Broth (LB) or M9 medium supplemented with appropriate antibiotics.

*Escherichia coli* DH5alpha. This strain was used for cloning. Cells were grown at 37° C. in LB supplemented with appropriate antibiotics.

Human embryonic stem cell (hESC) culture. Human ESC line H9 (sex: female) were cultured in E8 medium on matrigel (Corning) coated tissue culture plates at 37° C. and 5% $CO_2$ in a humidified incubator, with daily media change. Cells were split every 4-5 days with 0.5 mM EDTA in 1×PBS.

HAP1 cell culture. Human HAP1 cells (Horizon Discovery) were cultured in IMDM (Gibco) supplemented with 10% FBS (Corning) at 37° C. and 5% $CO_2$ in a humidified incubator, with daily media change. Cells were split every 2 to 3 days using TrypLE Express (Gibco).

Method Details

Expression and Purification of TfuCas3 and TfuCascade

T. *fusca* Cascade and Cas3 was purified as described previously (Xiao et al., 2018), with minor modifications. TfuCascade was recombinantly expressed in *E. coli* BL21 cells in LB media using a three-plasmid co-expression system. Cse1 is encoded on one vector (pET19b) with an N-terminal 6×His-TwinStrep-SUMO tag. The rest of the Cascade components (Cse2, Cse4, Cas5e, and Cse3) were encoded polycistronically in another vector (pCDF-Duet1) with a C-terminal NLS tag on Cse4. The crRNA was expressed from a synthetic CRISPR array containing three repeats and two spacers in ORF1 position of pRSF-Duet1. Cells were grown at 37° C. until the OD600 is between 0.6 and 1.0. Protein and RNA expression were induced by adding IPTG to a final concentration of 0.5 mM, and allowing the cell to grow overnight at 22° C. 12 liters of cells were harvested and lysed by sonication in lysis buffer containing 30 mM HEPES pH 7.5 and 500 mM NaCl. The supernatant after centrifugation was loaded onto ~5 mL of StrepTactin resin and 2 mg Avidin per L of cells was supplemented to prevent cellular biotin from binding to the column. The column was washed with 3×15 ml of lysis buffer, and the protein eluted with 10 ml of lysis buffer supplemented with 5 mM Desthiobiotin. After cleaving the TwinStrep-SUMO tag with SUMO protease overnight at 4° C., TfuCascade was concentrated and buffer-exchanged to a buffer containing 30 mM HEPES pH 7.5 and 200 mM NaCl, and further purified on MonoQ. The pooled fractions were further purified by size-exclusion chromatography (Superdex 200 Increase 10/300 GL, GE Healthcare). The final RNP was buffer-exchanged to 30 mM HEPES pH8.0 and 150 mM NaCl, sterilized with a syringe filter, concentrated to >20 µM, and flash-frozen for −80° C. storage. To account for the nucleic acid component of TfuCascade, nanodrop UV 260/280 measurements were taken alongside a Bradford Assay standard curve. A conversion ratio was determined to more accurately estimate the concentration of the protein components.

TfuCas3 was expressed from M9 minimal media with an N-terminal TwinStrep-PreScission tag and a C-terminal 2×HA-NLS tag from a pET52b plasmid. A 5 ml starting culture was grown from LB media overnight at 37° C., propagated to a 100 mL M9 culture overnight at 37 C, then used to inoculate 3×2 L of M9 media. The trace metal supplement was left out of the standard M9 media to prevent $Fe^i$ incorporation into the Cas3 active site. 100 µM final concentration of cobalt chloride was added to the cell culture 30 minutes prior to IPTG induction, when the OD600 reached 0.6. Protein expression was induced by 1 mM IPTG overnight at 20° C. The cells were harvested, resuspended in lysis buffer (30 mM HEPES pH 7.5 and 500 mM NaCl), lysed by sonication, and purified with a Strep-Tactin column similar to TfuCascade purification. The eluted protein was treated with PreScission protease overnight at 4° C. to remove the TwinStrep tag. Cas3 was further purified over a HiLoad Superdex 200 size-exclusion column (SEC) equilibrated with 30 mM HEPES 7.5 and 150 mM NaCl. The main peak fractions were pooled and concentrated, flash-frozen in liquid nitrogen, and stored at −80° C. until needed.

Construction of hESC Dual-Reporter Line and DNMT3b Targeting Plasmids

Cells for transfection were harvested 2 days post passaging using TrypLE (Life Technologies) and resuspended in OptiMem (Life Technologies) at a final concentration of $5×10^6$ cells/mL. 500 µL of cell suspension was added to a 0.4 cm cuvette containing 30 µg of the linearized DNMT3B-EGFP vector. Cells were electroporated using condition 320 V, 200 µF, then plated on a 10 cm matrigel-coated dish in E8 media supplemented with 10 µM Y-27632 (Cayman Chemical). 0.5 µg/mL puromycin was added to the medium 3 days post-transfection, and drug-resistant colonies exhibiting uniform EGFP expression were identified by fluorescent microscopy. A single EGFP+ clone was expanded and the puromycin selection cassette removed following electroporation of CRE recombinase mRNA. A subsequent round of targeting was performed as described above using the DNMT3B-tdTomato vector. Individual colonies expressing both tdTomato and EGFP reporters were identified, isolated and expanded. Successful biallelic targeting of the endogenous DNMT3B was confirmed by genotyping PCR using primers flanking the DNMT3B start codon.

To create DNMT3B targeting constructs (hES-2A-DNMT3B-EGFP and hES-2A-DNMT3B-tdTomato), a BAC clone (CTD-2608L15) containing the complete DNMT3B coding region was obtained from CalTech Human BAC Library (Life Technologies). Red-ET recombination was used to insert a DNA cassette encoding a tdTomato or EGFP reporter gene adjacent to a loxP-flanked PGK promoter driven puromycin resistance gene at the DNMT3B start codon in exon 2. The ~40 kb SbfI fragment containing the modified DNMT3B locus was then subcloned into the copy number inducible BAC vector, hES-2A. Prior to transfection, these DNMT3B targeting constructs were linearized by SwaI.

RNP Electroporation of hESCs

The H9-DNMT3B-tdTomato/EGFP dual-reporter cells were electroporated using the Neon Transfection system (ThermoFisher) according to the manufacturer's instructions. Briefly, reporter cells were individualized with Accutase (ThermoFisher), washed once with DMEM/F12 (ThermoFisher) and resuspended in Neon buffer R to a concentration of $2 \times 10^6$ cells/mL. 20-120 pmoles of NLS-TfuCascade and 20-60 pmoles of NLS-TfuCas3 were mixed with approximately $10^5$ cells in buffer R in a total volume of 10 μL. This mixture was then electroporated with a 10 μL Neon tip (1100V, 20 ms, 2 pulses) and plated in 24-well matrigel-coated plates containing 500 μL E8 medium supplemented with 10 μM Y-27632. The media was changed to regular E8 medium 24 hrs post electroporation. Cells were cultured in E8 with daily media change until analysis.

RNP Electroporation of HAP1 Cells and Single Cell 6-TG Cytotoxicity Assay

The HAP1 cells were electroporated using the Neon Transfection system (ThermoFisher) according to the manufacturer's instructions. Briefly, HAP1 cells were individualized with TrypLE Express (Gibco), washed once with IMDM, 10% FBS and resuspended in Neon buffer R to a concentration of $2 \times 10^6$ cells/mL. 20-60 pmoles of NLS-TfuCascade and 20 pmoles of NLS-TfuCas3 were mixed with approximately $10^5$ cells in buffer R in a total volume of 10 μL. Each mixture was then electroporated with a 10 μL Neon tip (1575V, 10 ms, 3 pulses) and plated in 24-well tissue culture plates containing 500 μL IMDM, 10% FBS. Cells were individualized 2 days after electroporation and seeded into 6-well plates at a density of ~200 cells per well. 6-TG (6-Thioguanine, Sigma) was added to the media 2 days after cell seeding at a final concentration of 15 μM. 6-TG selection was carried out for 6 days. The cells were then fixed with ice cold 90% methanol for 30 min, washed once with 1×PBS and stained with 0.5% crystal violet at RT for 5 min. After destain with water, the plates were allowed to air-dry at RT overnight. The number of surviving colonies on the plate was then counted by OpenCFU (Geissmann, 2013).

Flow Cytometry Analysis, FACS Sorting and Single Cell Isolation

Cells were individualized with Accutase 4-5 days after electroporation and resuspended in DMEM/F12 media immediately before experiments. For analysis, individualized cells were analyzed on an LSR Fortessa (BD) using 488 nm laser for EGFP and 561 nm laser for tdTomato. Data analysis was performed using FlowJo® v10.4.1. For FACS sorting, individualized cells were put on a SH800 cell sorter (Sony) fitted with a 130 μm chip and GFP negative cells were sorted directly into a well of a 24-well plate coated with matrigel and filled with 1.5 ml E8 media supplemented with 10 μM Y-27632 and 25 μg/mL recombinant human albumin (Sigma). Sorted cells were then cultured in tissue culture incubator with 5% $CO_2$ at 37° C. Media was changed to regular E8 one day after sorting and daily media change with E8 was carried out thereafter. For isolating single cell clones, GFP-negative and tdTomato-positive cells were sorted directly into 96-well plate (one cell per well) coated with matrigel and filled with 150 μL E8 media supplemented with 10 μM Y-27632 and 25 μg/mL recombinant human albumin (Sigma). Media was changed to regular E8 two days after sorting and media change with E8 was carried out every two days thereafter.

DNA Lesion Analysis by Long-Range PCR Genotyping

Genomic DNAs of hESCs or HAP1 cells were isolated using Gentra Puregene Cell Kit (Qiagen) per manufacturer protocol. Long-range PCRs in FIGS. 3B, 3D, 6E, 9B, and 11B were all done using Q5 DNA Polymerase (NEB). Products were resolved on 1% agarose gel stained by SYBR Safe (Invitrogen) and visualized with Chemidoc MP imager (Biorad). See Table 1 for all primers used for long-range PCRs.

Figure 4:
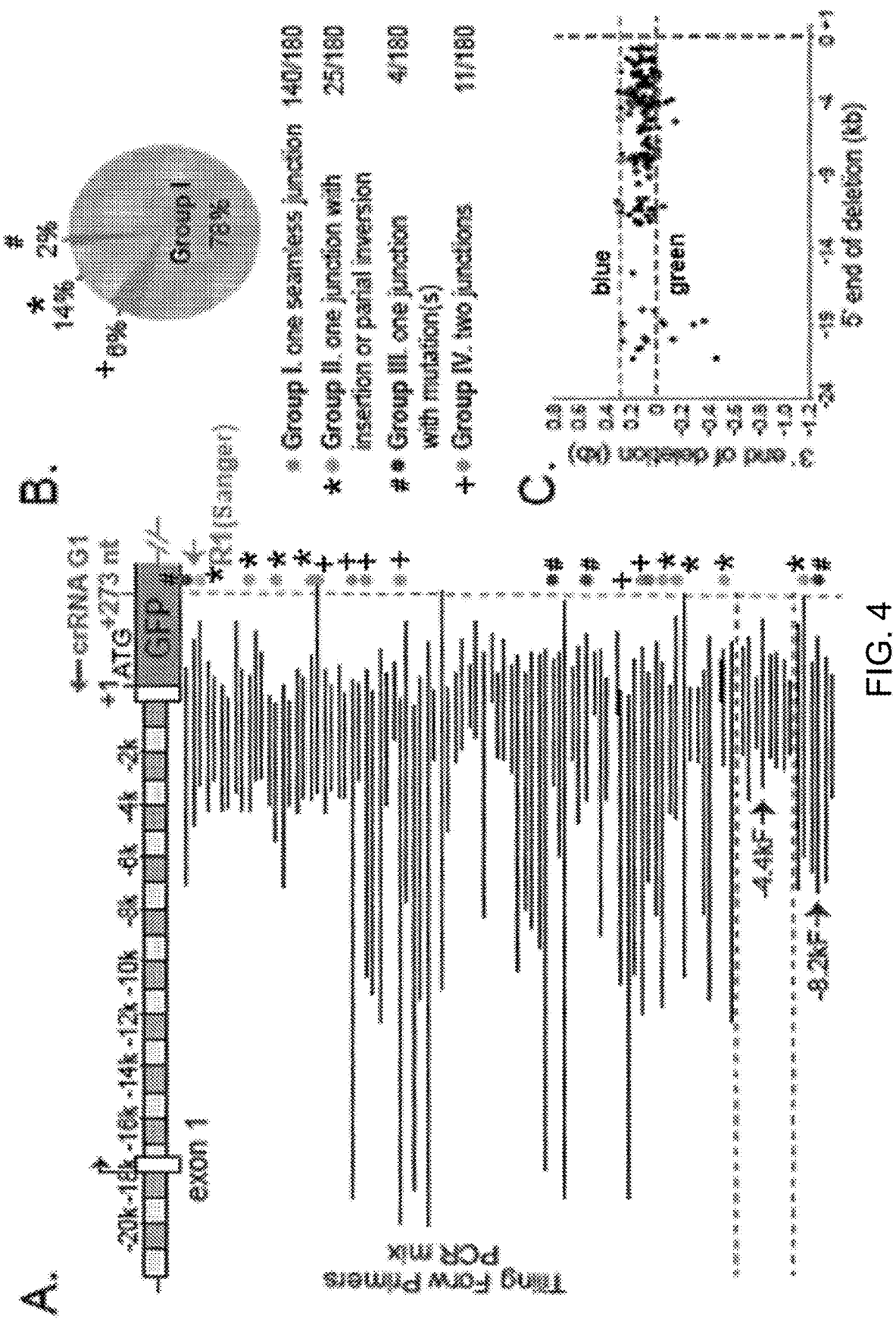
FIG. 4. Type I CRISPR induced deletion/repair junctions are revealed at single nucleotide resolution by sanger-sequencing. (A) Representative deletion locations at the DNMT3B-EGFP locus, revealed by cloning of pooled tiling PCRs in FIG. 3D and Sanger sequencing. The entire PCR in lanes 4 or 8 of FIG. 3B was also analyzed, the detected lesions are shown at the bottom. R1, reverse primer used for Sanger sequencing. Black lines, deleted genomic regions. Orange (*), magenta (#), green (+), and the lack of dots on the right indicate Groups II, III, IV, and I deletion junctions as described in (B). (B) A pie chart of the four groups of deletion junctions identified. Group I (light blue), one seamless junction; Group II (orange (*)), one deletion with a small insertion or partial inversion; Group III (pink (#)), one deletion with point mutations; Group IV (green (+)), two deletions. (C) Scatter plot for the 180 unique junctions, showing the upstream (5', X-axis) and downstream (3', Y-axis) end points of the chromosomal deletions, relative to the EGFP translation start site (+1, marked by the dashed green line) at the DNMT3B locus. Dashed blue line, recognition site for Cascade-G1. (D) Schematics of the gene structure of representative groups I, II, III, and IV lesion junctions. Black horizontal line, reference and sequenced alleles; gray shadow; direct match between the reference and sequenced alleles. Lack of grey shadow at the reference locus represents a deletion in the sequenced allele. Orange bar, an insertion or partial inversion; pink line, point mutation(s). Cascade-G1 recognition site (+273, relative to the beginning of EGFP ORF+1) is marked by the vertical dashed line in (A) and (C). (E) Example Sanger sequencing results showing representative lesion events by location. Sizes of the deletions are shown in parentheses.
Figure 4:
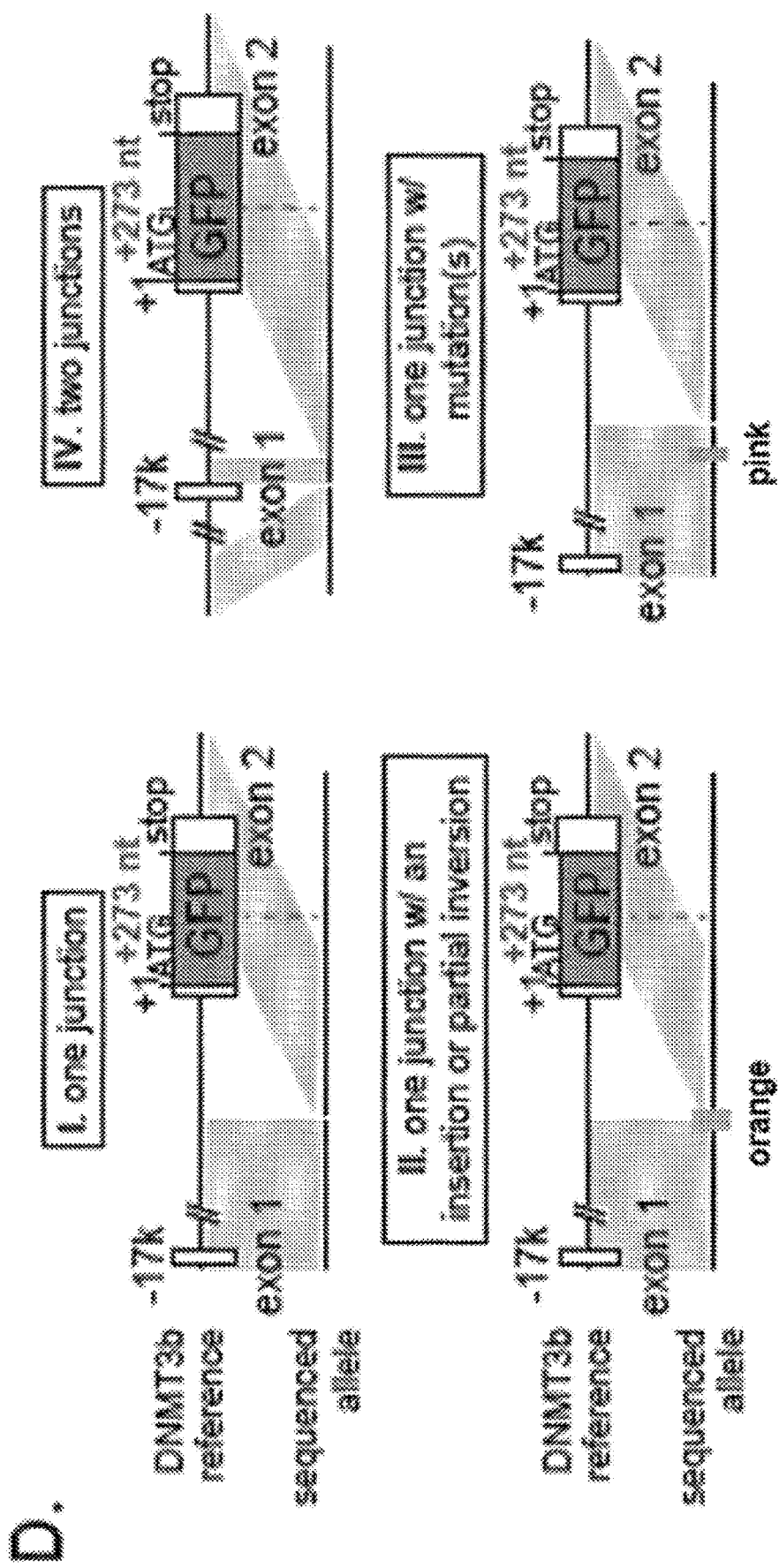
Figure 5:
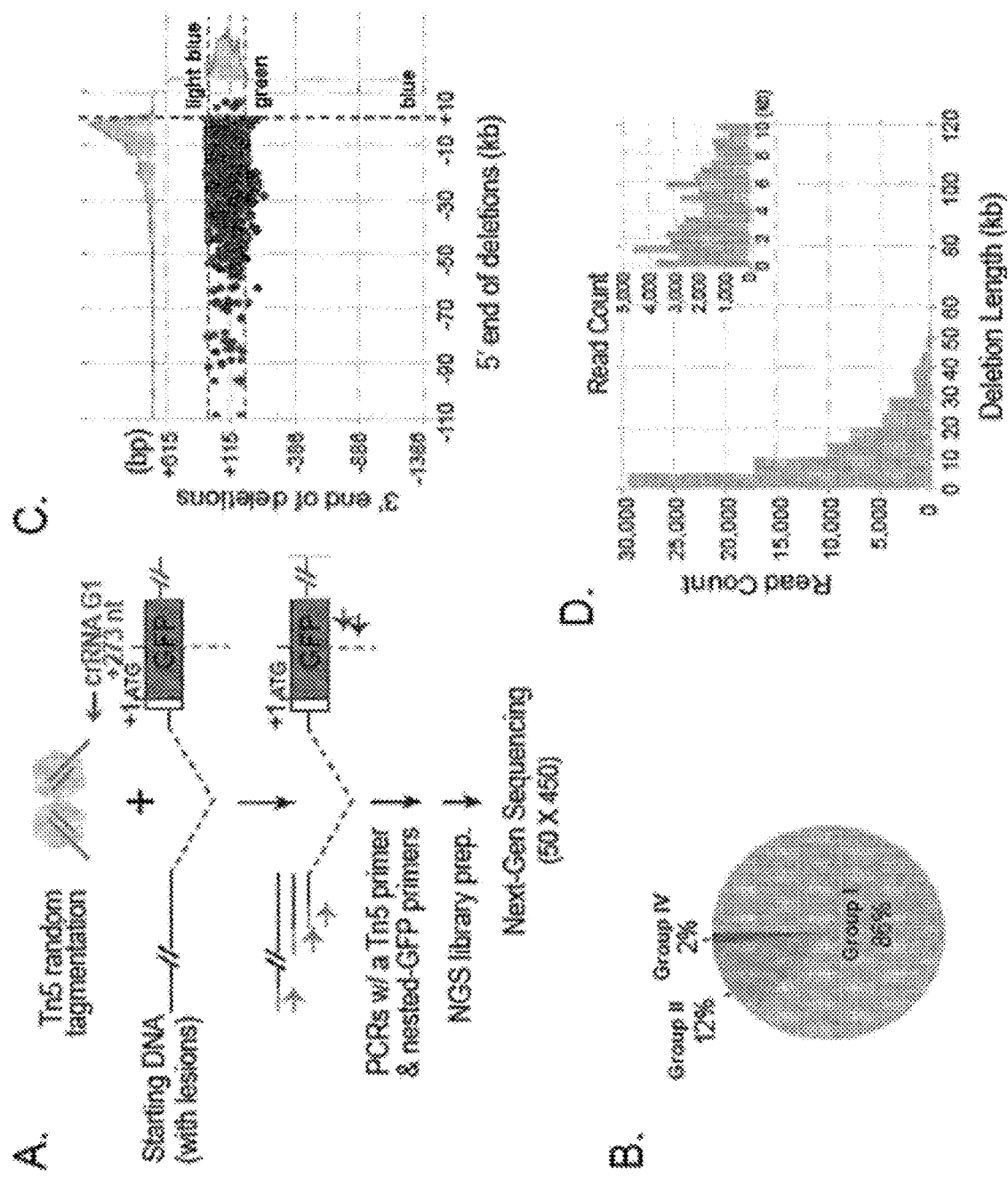
FIG. 5. Tn5- and NGS-based characterization of Type I CRISPR-induced genome deletions. (A) Schematic of Tn5 tagmentation procedure and NGS library construction. (B) Pie chart of three main types of lesion-containing reads identified by Miseq analysis. Light blue, Group I (one deletion junction); orange, Group II (a deletion with a large [>=9 bp] insertion, including partial inversion); green, Group IV (two deletions). The coloring and labeling scheme and categorization for deletion junctions are consistent with FIG. 4B. (C) Scatter plot for all Group I lesion-containing reads, showing the upstream (5', X-axis) and downstream (3', Y-axis) end points of the chromosomal deletions, relative to the EGFP translation start site (+1) at the DNMT3B locus. Dashed green line, and light blue lines, the (+1) start of the EGFP ORF; dashed blue line, recognition site for Cascade-G1. Kernel density estimates for the marginal distributions are shown along the axes, revealing the narrow range of downstream deletion endpoints and very long-tailed distribution of upstream deletion endpoints. (D) Histogram showing the distribution of deletion lengths observed for all the Group I reads in (B). The inset view on the top right corner is a zoom-in on deletions smaller than 10 kb.
Figure 11:
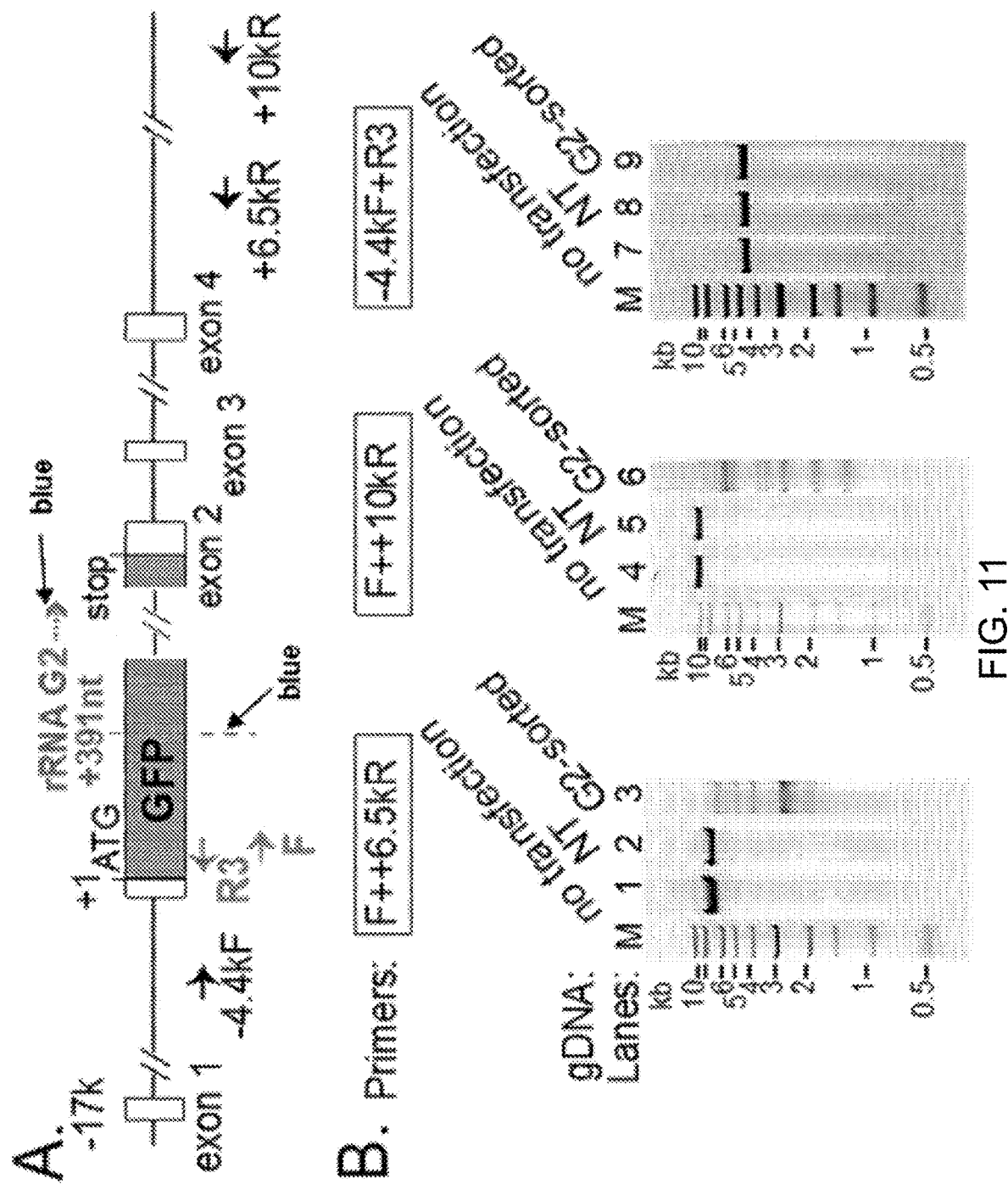
FIG. 11. Long-range PCR and Sanger sequencing analysis of deletions induced by Type I CRISPR at a $2^{nd}$ target site G2. Related to FIGS. 1-2. (A) Schematic of the EGFP reporter at DNMT3B locus and annealing sites for five PCR primers used in (B). Positions relative to the EGFP translation start site (+1) are indicated. Recognition site for Cascade-G2 is marked by the dashed blue line. Blue arrowhead, direction of Cas3 translocation. (B) PCR-based DNA lesion characterization. A spectrum of chromosomal deletions was introduced downstream of EGFP by Cascade-G2 and Cas3, in the sorted EGFP-negative population. PCR primers used are indicated and their annealing sites depicted in (A). M, DNA size markers. (C) Representative lesion locations revealed by cloning of the entire PCR in lanes 3 and 6 in (B) and Sanger sequencing. Black lines, deleted genomic regions. Orange (*), magenta (#), green (+), and the lack of dots on the left indicate groups II, III, IV, and I junctions, as in FIG. 4. (D) 4 representative Sanger sequencing results showing DNA lesion events designated by position. Sizes of the deletions are shown in parentheses.
Figure 11:
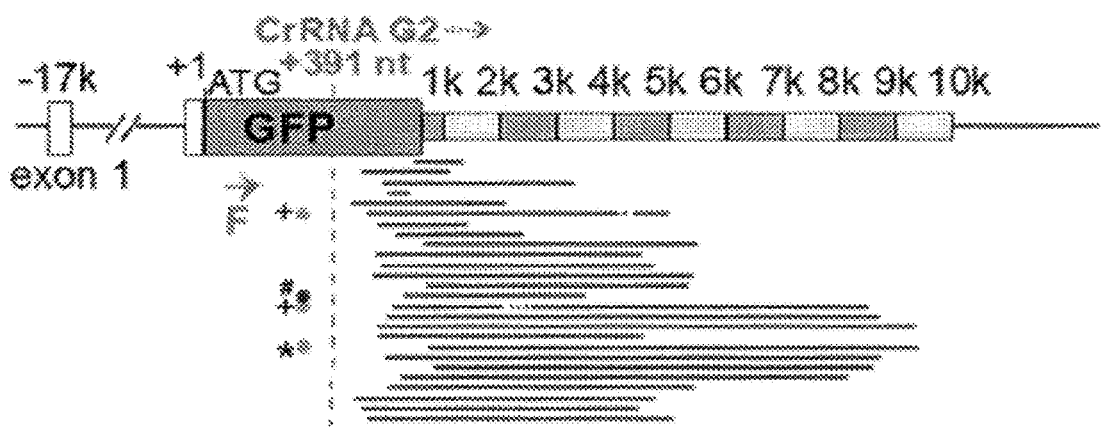

To define lesion junctions shown in FIGS. 4, 6F, 11 and Table 3, lesion PCR reactions were purified using QIAquick PCR Purification Kit (Qiagen), and cloned into PCR-BluntII-TOPO vector (Invitrogen). Colony PCR with M13 forward and reverse primers were carried out from the resulting colonies, and randomly selected positive clone amplicons were Sanger sequenced (Eurofin) using an EGFP reverse primer HZG511 or HPRT primer oYZ960. Sanger sequencing results were analyzed using Snapgene and BLASTN search.

Tn5 Tagmentation-Based NGS Library Construction

Tn5 transposase was purified and loaded with one pre-annealed oligo pair ME-A/ME-rev as previously described (Picelli et al., 2014). Tagmentation was performed in 10 mM Tris pH8.5, 5 mM $MgCl_2$ and 50% DMF using 300 ng of genomic DNA and 1.4 μg of loaded Tn5, in a total volume of 40 μL. After 7 min incubation at 55° C., tagmentation reactions were stopped by addition of 1 μL Protease K (20 mg/ml) and incubation at 55° C. for 7 min and 95° C. for 10 min. Tagmented DNA was purified with 32 μl AMPure beads and eluted with 15 μL 10 mM Tris pH 8.0. For NGS library construction, $1^{st}$ step PCR amplification was carried out using Q5 DNA Polymerase for 15 cycles with oligos OYZ510+478, and then treated with Exonuclease I (NEB) to digest excess primers. $2^{nd}$ step of nested-PCR was done for another 15 cycles using Q5 with OYZ510+511. After Exonuclease I treatment, the $3^{rd}$ step PCR was carried out for 10 cycles with OYZ510 and index primers. The final NGS libraries were purified using Select-a-Size DNA Clean & Concentrator MagBead Kit (Zymo Research) using a 400 bp cutoff, eluted in 10 mM Tris pH 8.5 and sequenced on Illumina MiSeq with a 500 cycles Nano kit for 50×450 bp paired-end reads. 450 cycles were performed for R2 and 50 cycles for R1.

NGS Data Analysis

MiSeq R2 sequencing reads were first subjected to adapter trimming using cutadapt 1.8.1 (Martin, 2011) to ensure that all reads began with the expected sequence immediately following the GFP sequencing primer, and trimming the Tn5 adapter sequence from the ends of reads in case of read-through. Reads were then quality trimmed using Trimmomatic v0.33 (Bolger et al., 2014) filter settings "TRAILING:3 SLIDINGWINDOW:4:15 MINLEN:10", and then aligned to a defined window of the human genome spanning ~130 kb, which covered the entire DNMT3B locus with EGFP sequence inserted along with 91 kb upstream of DNMT3B transcription start site. Alignment was performed using nucmer 4.0.0beta2 (Kurtz et al., 2004) with a minimum match length of 10 and minimum cluster length of 20. nucmer alignments were then filtered using an in-house python program first to prune any alignments which overlapped by more than 10% of their length with another, longer alignment of the same read, thus removing redundant alignments which would otherwise occur, and then to remove any alignments that were not properly anchored to the expected start site based on the sequencing primer used. Python and bash programs were subsequently used to extract and plot read counts and locations.

Purification and Assembly of SpyCas9 RNP

NLS-tagged SpyCas9 was purified using a modified protocol as described previously (Zuris et al., 2015). Briefly, BL21 (DE3) cells were grown at 37° C. until the OD600 reaches 0.6. Protein expression was induced by adding IPTG to a final concentration of 0.5 mM, and allowing the cell to grow overnight at 18° C. Cells were collected by centrifugation, resuspended in 1×PBS with 350 mM NaCl and lysed by sonication. Cleared lysate was mixed with Ni resin at 4° C. for 1 hour. After washing with lysis buffer, bound proteins were eluted with 1×PBS, 350 mM NaCl and 0.5 M Imidazole. Proteins eluted from Ni resin was then loaded onto a 5 ml Heparin column (GE Healthcare) and eluted with a step gradient of NaCl (1×PBS with 600 mM NaCl, 850 mM NaCl and 2 M NaCl). Cas9 containing fractions were pooled, concentrated and dialyzed into 1×PBS, 20% glycerol overnight. Dialyzed proteins were filter sterilized and stored at −80° C. until use.

The HPRT1-targeting sgRNA for SpyCas9 was generated using GeneArt Precision gRNA Synthesis Kit (ThermoFisher) following manufacture's instruction. For SpyCas9 RNP assembly, 3 µg (19 pmoles) of NLS-SpyCas9 and 1.2 µg (37 pmoles) of sgRNA were mixed in buffer R to 5 µL. After 10 min incubation at RT, this reaction was mixed with $10^5$ cells in buffer R to a final volume of 10 µL for electroporation.

T7E1 Assay 50 ng genomic DNA was used for PCR amplification using Q5 DNA polymerase supplemented with 1×GC enhancer (NEB) with oligos oYZ954+oYZ955 that flank the targeted site. 20 µL of each PCR product was heated to 95° C. for 1 min and cooled down to 23° C. at a rate of 0.1° C./sec. 10 µL annealed PCR product was digested with 1 µL T7 endonuclease I (NEB) reaction in 1×NEBuffer 2.1 at 37° C. for 1 hr, and resolved on a 2.5% agarose/1×TAE gel. The gels were imaged with ChemiDoc MP and quantified using Image Lab (BioRad). Editing efficiency (% lesion) was calculated using the formula: $100×(1−(1−\text{fraction cleaved})^{1/2})$(Guschin et al., 2010).

In Silico Off-Target Prediction

To predict potential off-target sites, we searched the entire human genome for sequences that match the intended target site as closely as possible. We demanded a 'NAG' PAM (−3, −2, −1 positions) and a perfectly matched seed-proximal region (positions 1-5, 7-11), while allowing all possible mismatches to the kinked positions ($6^{th}$, $12^{th}$, $18^{th}$, $24^{th}$, and $30^{th}$ positions). Top predicted off-targets sites with minimum number of mismatches at the non-seed, non-kinked positions are listed in Table 3. The search and scoring described above were implemented using elementary string operations in python 2.7, with sequence input provided by Biopython, and applied to the hg38 reference sequence The following representative sequences are used to illustrate, but not limit embodiments of the disclosure, including but not limited to representative modifications of sequences.

```
T. fusca:
Cas3
Nucleotide:
                                                        (SEQ ID NO: 3)
cccgaacacgattctacagatgacaagcacggtatcccaccgctcgacttgaggttctgggcgaaagaacgcggccttcgcggcaa gacctacccccttggtgtgccattccctcgacgctgctgccgcggcattggtgttgtggaacgaatatctctctcccgggctgcgagaca cgatcgcttcgtctatggagactgacgaagagcacgcgggacactgcatcgctttctgggcggggttgcatgacatagggaaactaa cccgagagttccaacagcagatcgctatcgacctttccgcttatcccggggaggagctcagtggggaacaaaggtcccatgctgccg cgaccggtaaatggctgccgttcgcgcttccttcactcggctatcccaacggaggactagtcaccggcctcgttcccagatgcttggg ggccatcacggtacgttccacccacaccccctcttttcaaagccgcaatccgctagcggagttcggcttttcctcgccgcactgggagaa gcagcgccacgccctgctgcacgcagttttttgatgcgacggggcgtcccacacctcctgacatgcttgacgggcctacagcatcggt cgtgtgcggcctggtcatccttgctgactggctggtcagccaggaggattttctcctggaacgtctcacctccctgcccgcagacggttc cgcgtctgcactgcgcgcccactttgaaacgtcgctacggcgcatccctcacttctcgacgccgcgggtctacggccgatcacagtt cctccggccacgttcactgagtcgtttccgcacctgagcaagcccaacgccttcaagcatcgttggcgaaacaccttccttgcctgtg caccggtccgggattagtgctgatcaccgcgcccatgggtgagggcaagaccgaagccgcctaccatgtggcggatctgctgggga aggcaacggggcgccctggacgttttcttgcgcttccaccatggccactgctgaccagatgcacacccggctcaaggagtacgcac gctaccgggtggagaacacagaccttccgcgctcctccacgctggccctcctgcattcaatggcgtggctgaatcccgactacgccc ccgccgacctgccaggcgtgtcgaaagtgctctctaatctcgggcaccgcgatccgtttgccgcaactgactggctgatgggggcgtaa acggggcctactcgctccctgggcagtcggcacaatcgaccaagcactcatggcggtgctgcgtgcgaaacacaacgcgctgcgc
```

-continued

```
ctgttcgggcttgctgggaaagtggtggttgtcgacgaggcgcacgcggtcgacccttacatgcaggtcctcttggaacagttgctgc
gctggctgggcacgcttgatgtgccggtagtgctgctgtcggccgccttgcatcacagcatcgcgaactcacttgtcaaggcgtacctg
gaaggtgcccgaggcagaaggtggaacaggtctgaaccgcagcctgtttcggaggtctcctaccctggctggctgcacgttgacgct
cggatcggaaaagtgactcgcagcagcgacgtcgacccttgcctatcgctacgactccccgcaagcccttggaggtgcggcttgtg
gacgtgccggtcaaggagggagccctaaaccggtccacggtgctcgctaaggagctgactccactagtgaagcagggaggatgcg
cagcgatcatctgcaccacggttgctgaagcccagggagtctacgatctgctttcccagtggtttgcgacgctcggtgaggacgcccc
cgacctttacctgctgcattcgcggttccctaaccggcagcgcacggagatcaccgcgaccatcgttgacctgttcggtaaagaaggt
gcacagagcggacggagacccactcgcggcgctgtcctggtagccacccaagtggtggagcagtccctcgacttggacgtggattt
gatgatcagcgacctcgctccagtgtcgctgttgctgcaaacgggcgggacgctgctggcggcacgaacacctgggcatcatcaacc
gtccccaatgggccaaacagcccgagcttgtggtactcacccccgaacagaacggcgacgctgatagggctccgtggtttccgcgtt
cctggacatcggtgtacccgctggcattgctccagcgcacgtacacactgctgcgccgcaggaacggggcccggtgcagattcct
gaagacgtgcagcagcttgtggacgacgtgtatgacgacgactcgctcgctgaagatctagaagcagacatggagcgcatggggga
ggagctggcacaacgcggcttggcgcgaacgcggtcatccccgacccagacgatgcggaagacaacctgaacgggctcaccga
gttcagctttgatgtggacgagcacgtgctcgcgacccggttcggtgccggttcagtccgggtgttgtgctactacgtggacacggcg
gggaaccgctggcttgaccctgaatgcacggtcgagtttcctgaacagggcacggggcgagagggccggttcaccatggcagact
gccgcgacctggtggcccgcacgatcccggtgcgtatgggtccctgggcgagtcaactcaccgaggacaaccatcctcctgaggca
tggcgggagtcgttctaccttcgcgacctggttcttatacctcaacgtgtgacagacgagggcgcggtgctccccactgaaaccggtg
gacgagagtggttgcttgatccctgtaaggggctgatcttttAa
```

Protein: (SEQ ID NO: 1)

PEHDSTDDKHGIPPLDLRFWAKERGLRGKTYPLVCHSLDAAAAALVLWNEYLSPGL
RDTIASSMETDEEHAGHCIAFWAGLHDIGKLTREFQQQIAIDLSAYPGEELSGEQRSH
AAATGKWLPFALPSLGYPNGGLVTGLVAQMLGGHHGTFHPHPSFQSRNPLAEFGFS
SPHWEKQRHALLHAVFDATGRPTPPDMLDGPTASVVCGLVILADWLVSQEDFLLER
LTSLPADGSASALRAHFETSLRRIPSLLDAAGLRPITVPPATFTESFPHLSKPNGLQASL
AKHLPCLCTGPGLVLITAPMGEGKTEAAYHVADLLGKATGRPGRFLALPTMATADQ
MHTRLKEYARYRVENTDLPRSSTLALLHSMAWLNPDYAPADLPGVSKVLSNLGHR
DPFAATDWLMGRKRGLLAPWAVGTIDQALMAVLRAKHNALRLFGLAGKVVVVDE
AHAVDPYMQVLLEQLLRWLGTLDVPVVLLSATLEIRSIANSLVKAYLEGARGRRWN
RSEPQPVSEVSYPGWLHVDARIGKVTRSSDVDPLPIATTPRKPLEVRLVDVPVKEGAL
NRSTVLAKELTPLVKQGGCAAIICTTVAEAQGVYDLLSQWFATLGEDAPDLYLLHSR
FPNRQRTEITATIVDLFGKEGAQSGRRPTRGAVLVATQVVEQSLDLDVDLMISDLAP
VSLLLQRAGRCWRHEHLGIINRPQWAKQPELVVLTPEQNGDADRAPWFPRSWTSVY
PLALLQRTYTLLRRRNGAPVQIPEDVQQLVDDVYDDDSLAEDLEADMERMGEELAQ
RGLARNAVIPDPDDAEDNLNGLTEFSFDVDEHVLATRFGAGSVRVLCYYVDTAGNR
WLDPECTVEFPEQGTGREGRFTMADCRDLVARTIPVRMGPWASQLTEDNHPPEAWR
ESFYLRDLVLIPQRVTDEGAVLPTETGGREWLLDPCKGLIF-

Modifications:
C-terminal 2xHA-NLS Tag: (SEQ ID NO: 4)

. . . CKGLIFGSVGYPYDVPDYAGYPYDVPDYAGSYPEFPKKKRKV

N-terminal Twin-Strep-HRV: (SEQ ID NO: 5)

MWSHPQFEKGGGSGGGSGGSAWSHPQFEKLEVLFQGPVPEHD . . .

-continued

Cse1/CasA
Nucleotide:

(SEQ ID NO: 6)

GTGCTGTCGGTTGCCCTGTGTTTTCTTGTGGGAGGAGCCATTCCTTCACCGCCGTC

ATTTGATGTGACCATCGCTCCTTGGCTGATTGCGCGCAGCCGCGACGTCCTGGCC

GCACCCGAAATGCTGGGACTGCGTGACGTTCTCATCCGCTCCCACGAACTCTCCG

ACGTGGAGATTCCGCTTCCGCCTGGCGCGGCAGTACTGTGGCGGATACTCGCACT

GATCACCGCCCGCATCACCGGCCTCGACCAGCCGCCAAACAAGAATCCGAAGCG

GAAATGGCAGGCTCGCCGCAGCCAGATCCTCAGCAAAGGACGACTCGACCCGGA

AGCGGTCGACGCCTACTTCGCCGACTACTCGGAGCGCTTCGACCTGTTCCACCCT

GAGCGGCCCTGGTTGCAAGATCCTCGCCTGCGTGAAGAGTGTCCGAAAACCTCG

GGTGTCAACAAGCTGGCATGGGGCGCACCGCGGGAGAGAACCAGGTGTGGCTC

GGCGGCCACCACCATGACCTCGACCCGCACCCCCTCGACTCCGCTGAGGCTGTCT

GGCACCTGCTGGCAACTCTCGGCTACGGGCCTTCAGGGATGTGCACGGCTCGCGT

TGTCCGGGGAAGAAGCGAACGCAACGTCACCGCGGGGCCGCTGCGCGGCACCGT

CTCCTACCACCCGTTGGGCCGCACCCTGTTCGAAAGCCTGATCCTCAACATTCCC

TACCCCGGCACTGGTGCAGCCGACCTCGCCTTCTGGGAACAGCCAGAGCTCAAC

GACCCGCTCGGTCTTCCCGAAGAATCCGCGGGACTCGCCGGGATTCTGAGGCTCG

ACCACTTCCGCCATGCTGTCCTGCTGCACCCCTCGCCAGATGGTTCACACGTCGT

GGATGCATGGGTGACCTGGGCGTGGCGGGAACGCAACATTTCGCCAGAACTCGA

CCCTTACCTCATCTACCAGACAAGCAAGGAAGGCCGTGTCTATCCGCGGCCAGCC

GAAGCGGAACGGGCCATATGGCGGGACCTCGACGCCTTGCTGCACTACGGCGAA

GACGGCAACTACCGGCCGACAATTTTGGACAACTGCACGCCTTTGGCGCAGGTTC

CCCAAGAAGTCCTGGACTCCCTGCGGCTGCGCGCCTTCGGGTTCGACCAGGACG

GTCAGGCCCGTGACAAACAGTGGTTCACCGCCACCACCCCGGCCGTGCTGCGCT

GGCTAGCAGACCGGGAAACCGACGACAACGAGAACGCCCGAATCGTGCGTCGTA

TCACCCTGGCTCGCAAAGCCGCGGAAGCACTCGGCCGCCGCCTAGAAAAAGCGT

GCAAAGAAGCGTGGAAGGAAAGCAACAGCCCTAGCTCCACTAGCTCCGGCACCA

ACGCTAAGACCGAGACCGGTGTCGGACCCTGGGTGCAGCACGGCATGAGCCGCT

ACTGGGCGAAAGCCGAGCCGGTCTTCTGGAACATCGTCTACGACCGGCCCGCTC

AAGGCTACACCCCCGGCATGGCAGGCCCCGGAAACGCCTTCAACCTGGTCGCGT

TAGCTGCCTACGACGAGGTGACCGGTCCCTACTGTGAACGGCCCCGCGTGGCCA

AAGTCGTGGAGCGGCACCGCAGCACCCTGTTCAGCAACTGGACACCGAAACAGG

ACAAGGAAGCCGCGTGA

Protein:

(SEQ ID NO: 7)

VLSVALCFLVGGAIPSPPSFDVTIAPWLIARSRDVLAAPEMLGLRDVLIRSHELSDVEI

PLPPGAAVLWRILALITARITGLDQPPNKNPKRKWQARRSQILSKGRLDPEAVDAYF

ADYSERFDLFHPERPWLQDPRLREECPKTSGVNKLAWGRTAGENQVWLGGHHHDL

DPHPLDSAEAVWHLLATLGYGPSGMCTARVVRGRSERNVTAGPLRGTVSYHPLGRT

LFESLILNIPYPGTGAADLAFWEQPELNDPLGLPEESAGLAGILRLDHFRHAVLLHPSP

DGSHVVDAWVTWAWRERNISPELDPYLIYQTSKEGRVYPRPAEAERAIWRDLDALL

HYGEDGNYRPTILDNCTPLAQVPQEVLDSLRLRAFGFDQDGQARDKQWFTATTPAV

```
-continued
LRWLADRETDDNENARIVRRITLARKAAEALGRRLEKACKEAWKESNSPSSTSSGTN

AKTETGVGPWVQHGMSRYWAKAEPVFWNIVYDRPAQGYTPGMAGPGNAFNLVAL

AAYDEVTGPYCERPRVAKVVERHRSTLFSNWTPKQDKEAA-

Modifications:
N-terminal 6xHis-TwinStrep Sumo Tag:
                                                                (SEQ ID NO: 8)
MHHHHHHSSGLVPRGSHMASWSHPQFEKGGGSGGGSGGSAWSHPQFEKMSDSEVN

QEAKPEVKPEVKPETHINLKVSDGSSEIFFKIKKTTPLRRLMEAFAKRQGKEMDSLRF

LYDGIRIQADQTPEDLDMEDNDIIEAHREQIGGSLSV...

Cse2/CasB
Nucleotide:
                                                                (SEQ ID NO: 9)
GTGAACAGCGACTACATACTCCAGCACGCTGATGCCCTCGTGAAACGGGTGAGC

AAGCTCATTGTCAACGAACCAGCGGCACGGGCCGCACTGCGGCGCGGTGTGGGA

CTGGCCCCCGAGGATCCGCGCATGCTGGCCGCTCACCGCGTGGTCGCCCCTTACG

TTCCCGTCCCCACCGACTACGACGTCGACCGTCGCCGGGCCGCGTCCCTATGGGA

CGTCCACGCTGTGGAGCGCGCCTTCTACGCAGTCGCAGCAATCATGGCCGCACA

GCCCAGAAGCGCCCGCGACCAGGAAGCGGAAGCTACCGAAGAACAAACCGGAG

AACCACAGGACAGCGAGGCACTCACTGAGCCAACCCCTGCCGAAGAAAGCAGC

GCCACCAAGGATGGAAAGCCGGACCGGCGGCCCAACCTGGGAGTATCCCTCGCT

CAAGCCGTCTTCGACAAAGGGCTCAACGCTGACAGCACCGAGCAGCGCCTGCAC

CTGATCGCCCGCCAGAACCTCGACGGCGTCCACCGCCACCTGCCGCGCCTGGTCC

TATACCTGCGCAGCGACCAAGTCCACATCGACTGGGGGATCCTCATCCGAGACCT

GGCCCGCTGGGGCCACACCCCCGCCACGTCGCCCGCGAATGGGTCCAGGACTA

CCACCGCACCCTCGAAACCCTGACCCGTCAAGCAGAGCAGAAAAACAAGAACAA

CACCACCGATGAGGAGGCCGAAGCAGCATGA

Protein:
                                                                (SEQ ID NO: 2)
VNSDYILQHADALVKRVSKLIVNEPAARAALRRGVGLAPEDPRMLAAHRVVAPYVP

VPTDYDVDRRRAASLWDVHAVERAFYAVAAIMAAQPRSARDQEAEATEEQTGEPQ

DSEALTEPTPAEESSATKDGKPDRRPNLGVSLAQAVFDKGLNADSTEQRLHLIARQN

LDGVHRHLPRLVLYLRSDQVHIDWGILIRDLARWGHTPRHVAREWVQDYHRTLETL

TRQAEQKNKNNTTDEEAEAA-

Modifications:
Sum Total of all Engineering (all region deletions/mutations relative to the
wild type sequence alignment can be used in combination, or individually):
                                                                (SEQ ID NO: 10)
MVNSDYILQHADALVKRVSKLIVAEPAARAALRRGVGLAPEDPRMLAAHRVVA

PYVPVPTDYDVDRRRAASLWDVHAVERAFYAVAAIMAAQPRSARDDRMHQRR

PNLGVSLAQAVPDKGLNADSTEQRLHLIARQNLDGVHRHLPRLVLYLRSDQVHI

DWGILIRDLARWGHTPRHVAREWVQDYHRTL*

Cse4/Cas7e/CasC
Nucleotide:
                                                                (SEQ ID NO: 11)
ATGACTTTCGTTGACATTCACGCCATCCAGACCCTGCCCTACTCCAACATCAACC

GCGACGACTTGGGCTCCCCCAAGACGGTCGTCTACGGCGGCAAGGAACGCACTC

GCGTGTCCAGCCAGAGCTGGAAGCGCGCCGTCCGCCACGAAGTGGAAGCCCGGC

TCGGCGACAAGGCGGTCCGCACCCGCCGTATCATCAGCGAGATCGCCAAGCGGC
```

-continued

```
TTCGGGAACGCGGCTGGGACGCTGACCTCGCTGACGCCGGAGCACGCCAAGTCG
TGCTGTCTGTCGGTAAGAAGAGCGGCATCAAACTGGAAAAGGAGAAAGACAGCG
AGGCCCCTGCCACTTCTGTCCTGTTCTACCTCCCGGTCCCCGCAATCGACGAACT
CGCCGCCATCGCCGATGAGCACCGGGACGCCGTCGCCAAAGAAGCAGCCAAGAA
GACCCCCAAGGGAATCCTCCCCGCTGACCGCATCACCGAAGTACTGAAGAGCCG
CAACGTCTCAGTCAACTTGTTCGGTCGGATGCTCGCTGAACTGCCCTCCACCGAG
GTCGACGGCGCAGTGCAGTTCGCGCACGCGTTCACCGTGCACGGCACCACCGTA
GAAGTCGACTTCTTCACCGCTGTCGACGACATCCCCAAAGAAAACGACCACGGT
AGTGGCCACATGAACGCGGGCCAGTTCAGTGCCGGAACGTTCTACCGCTACGCC
AACGTCAACCTCGACCGACTGGTGGAAAACACCGGTGACGCCCAAACCGCCCGC
ACCGCCGTGGCCGAGTTCCTCCGCGCTTTCCTGAGCACGGTCCCCTCCGGGAAAC
AGAACGCTACCGCTGCCATGACCCTGCCCGACCTGGTACACATCGCGGTACGCTT
CGACCGACCCATCTCTTTCGCTCCCGCGTTCGAAACCGCGCTATACGGCAGCGAC
GGCTACACCCTCCGCGCCTGCCAGGAACTCAACAACTACGCCGAACGGCTCCGC
GAAGTCTGGCCCGACGACGCGATCCGCGGCTACGCGACCGTGGAAAACAAGACC
GACCTCGCCGCGTTGGGGGAGCGGTACGACTCCTACCCGGCGCTCATCGACGCC
ATGGTCGCGGCAGCCTTCGAGGGGAGCGGGAGTGA
```

Protein:
(SEQ ID NO: 12)
```
MTFVDIHAIQTLPYSNINRDDLGSPKTVVYGGKERTRVSSQSWKRAVRHEVEARLGD
KAVRTRRIISEIAKRLRERGWDADLADAGARQVVLSVGKKSGIKLEKEKDSEAPATS
VLFYLPVPAIDELAAIADEHRDAVAKEAAKKTPKGILPADRITEVLKSRNVSVNLFGR
MLAELPSTEVDGAVQFAHAFTVHGTTVEVDFFTAVDDIPKENDHGSGHMNAGQFSA
GTFYRYANVNLDRLVENTGDAQTARTAVAEFLRAFLSTVPSGKQNATAAMTLPDLV
HIAVRFDRPISFAPAFETALYGSDGYTLRACQELNNYAERLREVWPDDAIRGYATVE
NKTDLAALGERYDSYPALIDAMVAAAFEGERE-
```

Modifications:
C-terminal NLS Tag:
(SEQ ID NO: 13)
AMVAAAFGSGSGGKLPKKKRKVEGERE-

Cas5e/CasD
Nucleotide:
(SEQ ID NO: 14)
```
GTGAGTGGCTTCCTGCTGCGGCTAGCTGGCCCCATGCAAAGCTGGGGCGAACAC
AGCATGTTCGGGGAACGCGACACCCTGCCTTACCCGAGCCGCTCCGGTCTGATCG
GAATGTTCGCTGCCGCCCAGGGGGTGCGCCGCGGCGACCCTCTGGACCGCTACA
AGGAACTGAAGTTCACCGTTCGCGTCGACCGGCCAGGGGTGCGGCTCGTCGACTT
CCACACGATCGGCGGCGGCCTTCCCAAAGAGCGCACCGTGCCCACCGCTGCAGG
TGAACGGCGCGACCCTAAGAAAGCCACCATCGTCACCAGCCGTTCCTACCTGGC
CGACGCCGTGTTCACCGTCGCTGTCACCGGACCGGAAGCAGACACTATCGCCGA
CGCGTTAGCCGCCCCCTACTGGCAGCCCTACCTGGGGCGGCGCGCGTTCGTTCCT
GACCCGCTACTGGTCCTGCGCCGCAGGGTCGCTGACCCGGTGCGAGAACTAGTG
GAAGCGGTGCCGCTCCCCCATCGCAGGGTGGAAGAAGACGCTGCAACTGTGCTT
GTGGACTTGATCTATGAAGAGGGCGAATACCCAGATACGCGCACTCTGACGGTG
CTCAACGACGTTCCGCTCTCGTTCGACAGCAAGAGCCGCCGCTACTCCACCCGAC
```

-continued

AGATCCGAGTAGTTCCCACCGAGGTTCCCGCGACACTCGTGGCCGGTCCCGGCA

GGGACTACCAGAACAAGCTTTTCACATACGTCAAGCAGTGCGCCGAGGAGGCAG

CATGA

Protein: (SEQ ID NO: 15)

VSGFLLRLAGPMQSWGEHSMFGERDTLPYPSRSGLIGMFAAAQGVRRGDPLDRYKE

LKFTVRVDRPGVRLVDFHTIGGGLPKERTVPTAAGERRDPKKATIVTSRSYLADAVF

TVAVTGPEADTIADALAAPYWQPYLGRRAFVPDPLLVLRRRVADPVRELVEAVPLP

HRRVEEDAATVLVDLIYEEGEYPDTRTLTVLNDVPLSFDSKSRRYSTRQIRVVPTEVP

ATLVAGPGRDYQNKLFTYVKQCAEEAA-

Cse3/Cas6e/CasE
Nucleotide: (SEQ ID NO: 16)

<u>ATGA</u>CGTGGCTAACCAAGATCGTTCCTGACCTGCGCTACCGCCAGACCCGAGCA

GACTTCCGTACCGCTGGAAATCTACATCGTAAACTCATCCGGCTTTCTTCTGACCT

CGGTGAGGAGCGGATCGCTAACCCCCGTCAGCAATCCGGCTTACTGTTCCGCATC

GAAGAAACCAGAAACGAGCTCTACCTGCTGGTACAGAGTCACTCCCCCCTGCGG

GTTGACCGGCTTGGCCCCGGATACCACGGGGTCCAGATGCGTAACCTCGACCCTT

TCCTGGCTCGGCTAGACAAAGGCAGCCGTGTCCGCTACCGGATTGTGGCCAGTCC

CACCAAACGACTCGGCCGGTCCGAGAACAACACCCAACGCCTTGGCCTGAAAGA

GCCGCCGAAAAAACCAAGAGAGTACACCTGGGCTCTGCGCGGGGCCGCAGCCGA

GGAGTGGTGGCATTCCCGTGCGGCAGCCAACGGACTGGAACTCCTCAGCACCTA

CGCGCAGACACTCGATGACGTCCGCGACCCTGGGACCGCTGACCGTAGCCGCAA

AATCCGCCACCCAGCCGTGCGCTTCGACGGTGAAGCCGTCATCTCTGACGTCGAC

GCCGTGCGTCATGCGGTACTTAACGGCATCGGCCGCGGCAAATCCTACGGCTGC

GGGCTGCTCAGCCTCGCCCTAATCGAGGAAGGAGAACATGGATAA

Protein: (SEQ ID NO: 17)

MTWLTKIVPDLRYRQTRADFRTAGNLHRKLIRLSSDLGEERIANPRQQSGLLFRIEET

RNELYLLVQSHSPLRVDRLGPGYHGVQMRNLDPFLARLDKGSRVRYRIVASPTKRL

GRSENNTQRLGLKEPPKKPREYTWALRGAAAEEWWHSRAAANGLELLSTYAQTLD

DVRDPGTADRSRKIRHPAVRFDGEAVISDVDAVRHAVLNGIGRGKSYGCGLLSLALI

EEGEHGcrRNA
Generic (single unit unprocessed - Repeat-Spacer-Repeat): (SEQ ID NO: 18)

GTGAGCCCCACGCACGTGGGGATGGACCGNNNNNNNNNNNNNNNNNNNNNNN

NNNNNNNNNGTGAGCCCCACGCACGTGGGGATGGACCG

Generic (processed) (SEQ ID NO: 19)

ATGGACCGNNNNNNNNNNNNNNNNNNNNNNNNNNNNNNNNGTGAGCCCCACGC

ACGTGGG

Spacers:
GFP crRNA-A:
Sequence: (SEQ ID NO: 20)

GTGGCATCGCCCTCGCCCTCGCCGGACACGCT

Expression Cassette:

(SEQ ID NO: 21)

ggatccGAGCCCCACGCACGTGGGGATGGACCGTGGCATCGCCCTCGCCCTCGC
CGGACACGCTGTGAGCCCCACGCACGTGGGGATGGACCGTGGCATCGCCCT
CGCCCTCGCCGGACACGCTGTGAGCCCCACGCACGTGGGGATGGTGACgaattc GFP crRNA-B:
Sequence:

(SEQ ID NO: 22)

*GCTAC*GTCCAGGAGCGCACCATCTTCTTCAAG

Expression Cassette:

(SEQ ID NO: 23)

gaattcGAGCCCCACGCACGTGGGGATGGACC*TACGTCCAGGAGCGCACCAT*
*CTTCTTCAAG*GTGAGCCCCACGCACGTGGGGATGGACC*gCTACGTCCAGGAG*
*CGCACCATCTTCTTCAAG*GTGAGCCCCACGCACGTGGGGATGGTGACaagctt GFP crRNA-C:
Sequence:

(SEQ ID NO: 24)

TCGATGCCCTTCAGCTCGATGCGGTTCACCAG

Expression Cassette:

(SEQ ID NO: 25)

aagcttGAGCCCCACGCACGTGGGGATGGACCTCGATGCCCTTCAGCTCGATGC
GGTTCACCAGGTGAGCCCCACGCACGTGGGGATGGACCTCGATGCCCTTCAG
CTCGATGCGGTTCACCAGGTGAGCCCCACGCACGTGGGGATGGTGACgcggccgc GFP crRNA-D:
Sequence:

(SEQ ID NO: 26)

CGCGATCACATGGTCCTGCTGGAGTTCGTGAC

Expression Cassette:

(SEQ ID NO: 27)

gcggccgcGAGCCCCACGCACGTGGGGATGGACCCGCGATCACATGGTCCTGCT
GGAGTTCGTGACGTGAGCCCCACGCACGTGGGGATGGACCCGCGATCACAT
GGTCCTGCTGGAGTTCGTGACGTGAGCCCCACGCACGTGGGGATGGTGACctcg
ag tdTomato crRNA-A:
Sequence:

(SEQ ID NO: 28)

ctggacatcacctcccacaacgaggactacac

Expression Cassette:

(SEQ ID NO: 29)

GGATCCGAGCCCCACGCACGTGGGGATGGACCGctggacatcacctcccacaacgaggactacacG
TGAGCCCCACGCACGTGGGGATGGACCGttttGAATTC

TABLE 1

Oligonucleotides used in this disclosure.

| No. | Oligo Name | Sequence, 5'-3' | Purpose |
|---|---|---|---|
| | | For Cascade, Cas3 expression and purification. | |
| 117 | CasC NLS 2 Fwd | GGCAAGCTTCCCAAGAAGAAGAGGAA<br>GGTGGAGGGGGAGCGGGAGTGAGTG<br>(SEQ ID NO: 30) | pCDF-Duet1/wt<br>CasB, CasC-NLS,<br>CasD, CasE |
| 118 | CasC GSLink 2<br>Rev | ACCTGAACCGCTACCGAAGGCTGCCGC<br>GACCATGG (SEQ ID NO: 31) | |
| 136 | CasD RBS Fwd | TTTAAGAAGGAGATATACATATGAGTG<br>GCTTCCTGCTGCGGCTA (SEQ ID NO: 32) | pCDF-Duet1/wt<br>CasB, CasC-NLS, rbs-<br>CasD, CasE |
| 137 | CasD RBS Rev | attaaagttaaacaaaaTTATTCCCGCTCCCCCT<br>CCACC (SEQ ID NO: 33) | |

TABLE 1-continued

Oligonucleotides used in this disclosure.

| No. | Oligo Name | Sequence, 5'-3' | Purpose |
|---|---|---|---|
| 134 | pRSF conversion for crRNA Fwd | Tcatcgaattttttgcagcag (SEQ ID NO: 34) | pRSF/crRNA expression, streamlined |
| 127 | pRSF conversion for crRNA Rev | Accatggcctatagtgagtcgtattaatttcctaatgc (SEQ ID NO: 35) | |
| | HPRT_target1 R | aattcGAGCCCCACGCACGTGGGGATGGA CCGaccttgcactacctgtgcttccattdcctgGTGAG CCCCACGCACGTGGGGa (SEQ ID NO: 36) | pRSF-crRNA-HPRT-G1 expression, streamlined |
| | HPRT_target1 S | agcttCCCCACGTGCGTGGGGCTCACcagga aaatggaagccacaggtagtgcaaggtCGGTCCATCC CCACGTGCGTGGGGCTCg (SEQ ID NO: 37) | |
| | HPRT_target2 R | aattcGAGCCCCACGCACGTGGGGATGGA CCGaagccgaggctcccccagcgaagccccdtccGTG AGCCCCACGCACGTGGGGa (SEQ ID NO: 38) | pRSF-crRNA-HPRT-G2 expression, streamlined |
| | HPRT_target2 S | agcttCCCCACGTGCGTGGGGCTCACggaaa ggggcttcgctgggggagcctcggcttCGGTCCATCC CCACGTGCGTGGGGCTCg (SEQ ID NO: 39) | |
| | HPRT_target2_mut* R | aattcGAGCCCCACGCACGTGGGGATGGA CCGCagccgaggctcccccagcgaagccccdtccGTG AGCCCCACGCACGTGGGGa (SEQ ID NO: 40) | pRSF-crRNA-HPRT-G2* expression, streamlined |
| | HPRT_target2_mut* S | agcttCCCCACGTGCGTGGGGCTCACggaaa ggggcttcgctgggggagcctcggctGCGGTCCATC CCCACGTGCGTGGGGCTCg (SEQ ID NO: 41) | |
| 113 | Cas3 CTD+2XHA-NLS (gBlock) | Cacgtgctcgcgaccccggttcggtgccggttcagtccgggtgt tgtgctactacgtggacacggcggggaaccgctggcttgaccc tgaatgcacggtcgagtttcctgaacagggcacggggcgaga gggccggttcaccatggcagactgccgcgacctggtggcccg cacgatcccggtgcgtatgggtccctgggcgagtcaactcacc gaggacaaccatcctcctgaggcatggcgggagtcgttctacc ttcgcgacctggttcttataccctcaacgtgtgacagacgagggc gcggtgctcccactgaaaccggtggacgagagtggttgcttg atccctgtaaggggctgatcdtGGATCCGTTggtTAC CCATACGATGTTCCTGACTATGCGGGC TATCCCTATGACGTCCCGGACTATGCA GGATCCTATCCAGAATTCcccaagaagaagag gaaggtgtAactcgag (SEQ ID NO: 42) | pET28b/Cas3-2xHA-NLS |
| | GFP crRNA-G1 Synthesis | gaattcGAGCCCCACGCACGTGGGGATGG ACCGGCTACGTCCAGGAGCGCACCATC TTCTTCAAGGTGAGCCCCACGCACGTG GGGATGGACCGGCTACGTCCAGGAGC GCACCATCTTCTTCAAGGTGAGCCCCA CGCACGTGGGGATGGTGACaagctt (SEQ ID NO: 43) | pRSF/crRNA-G-1 |
| | GFP crRNA-G2 Synthesis | aagcttGAGCCCCACGCACGTGGGGATGG ACCGTCGATGCCCTTCAGCTCGATGCG GTTCACCAGGTGAGCCCCACGCACGTG GGGATGGACCGTCGATGCCCTTCAGCT CGATGCGGTTCACCAGGTGAGCCCCAC GCACGTGGGGATGGTGACgcggccgc (SEQ ID NO: 44) | pRSF/crRNA-G-2 |
| | crRNA-NT Synthesis | gaattcTAATACGACTCACTATAGGGAGC CCCACGCACGTGGGGATGGACCGCCA GTGATAAGTGGAATGCCATGTGGGCTG TCGTGAGCCCCACGCACGTGGGGATGG ACCGCCAGTGATAAGTGGAATGCCATG TGGGCTGTCGTGAGCCCCACGCACGTG GGGATGGACCGCCAGTGATAAGTGGA ATGCCATGTGGGCTGTCGTGAGCCCCA CGCACGTGGGGATGGACCGCAGTGA TAAGTGGAATGCCATGTGGGCTGTCGT GAGCCCCACGCACGTGGGGATGGACC GCCAGTGATAAGTGGAATGCCATGTGG GCTGTCGTGAGCCCCACGCACGTGGGG ATGGACCGCTAGCATAACCCCTTGGGG | pRSF/crRNA-NT |

TABLE 1-continued

Oligonucleotides used in this disclosure.

| No. | Oligo Name | Sequence, 5'-3' | Purpose |
|---|---|---|---|
| | | CCTCTAAACGGGTCTTGAGGGGTTTTT Tggatcc (SEQ ID NO: 45) | |
| | tdTomato crRNA synthesis | ATATCATAGTACAATAGGATCCGAGCC CCACGCACGTGGGGATGGACCGctggacat cacctcccacaacgaggactacacGTGAGCCCCAC GCACGTGGGGATGGACCGGAATTCAG TCGTAGTTTCGCGCATCATGGCCATA (SEQ ID NO: 46) | pRSF/crRNA-G-Td |

For PCR-based lesion analysis

| No. | Oligo Name | Sequence, 5'-3' | Purpose |
|---|---|---|---|
| OYZ438 | DNMT3b-F-4.4k | GATGGGGTGGGGGTTAAAGG (SEQ ID NO: 47) | PCR, FIGS. 3B, 3D, S5 |
| OYZ440 | DNMT3b-F-8.2k | AGTACTGCACTCTTTGCCCC (SEQ ID NO: 48) | PCR, FIGS. 3B, 3D |
| HZG81 | DNMT3b-F+1.0k | AAGGGAGACACCAGGCATC (SEQ ID NO: 49) | PCR, FIG. 3B |
| OYZ462 | DNMT3b+6.5kR | GGCCAATTACTGGGTTCAGG (SEQ ID NO: 50) | PCR, FIGS. 3B, S5 |
| OYZ478 | EGFP-R1 | ACGAACTCCAGCAGGACC (SEQ ID NO: 51) | PCR, FIG. 3B; NGS library |
| OYZ441 | DNMT3b+2.3kR | TAGCTCGGCAACCCTCCATA (SEQ ID NO: 52) | PCR, FIGS. 3D, S3B |
| OYZ437 | DNMT3b-2.7kF | ACTCTATGCCAGGCCCACTA (SEQ ID NO: 53) | |
| OYZ439 | DNMT3b-6.2kF | TCCTTTGGATGTGCTGTCCC (SEQ ID NO: 54) | PCR, FIG. 3D |
| OYZ868 | DNMT3b-11.5kF | AATGGCACTGGAGGAAGAGC (SEQ ID NO: 55) | |
| OYZ869 | DNMT3b-12.3kF | TGATGCCTTTGTAGGGCGTT (SEQ ID NO: 56) | |
| OYZ870 | DNMT3b-15.8kF | TCCACGATTAGGGAGTTGGC (SEQ ID NO: 57) | |
| OYZ882 | DNMT3b-21.4kF | TTGCAAGGTGACCACACAGT (SEQ ID NO: 58) | |
| OYZ883 | DNMT3b-19.1kF | TCGCGGTAAGTGCTAGGAAC (SEQ ID NO: 59) | |
| HZG511 | EGFP-R2 | GGTCTTGTAGTTGCCGTCGT (SEQ ID NO: 60) | For Sanger sequencings |
| OYZ635 | DNMT3b+1.2kR | GATCTCCGGGGTGCGGATA (SEQ ID NO: 61) | PCR |
| OYZ935 | DNMT3b+3.3kR | TGTCTTCCTCCTTTGCACTTT (SEQ ID NO: 62) | |
| OYZ826 | EGFP-R3 | CTTGTGGCCGTTTACGTCGC (SEQ ID NO: 63) | PCR |
| HZG707 | EGFP-F | GTGAGCAAGGGCGAGGAG (SEQ ID NO: 64) | PCR |
| OYZ463 | DNTM3b+10kR | CCTAAACCCAACTCCATGCC (SEQ ID NO: 65) | |
| OYZ960 | HPRT1-0.7kF | TGTCCTCTCAGATGTGTACCCT (SEQ ID NO: 66) | PCR |
| OYZ963 | HPRT1+2.3kR | ACACCCCAAAGCTAAAAGCG (SEQ ID NO: 67) | |
| OYZ964 | HPRT1+5.6kR | GGAGGGGCCTAGAAGTGGTA (SEQ ID NO: 68) | |
| OYZ965 | HPRT1+6.6kR | TCGACAAGCCCAGAAACTTGT (SEQ ID NO: 69) | |
| OYZ967 | HPRT1+11.3kR | CCGCTACCCCAATCCCAAAT (SEQ ID NO: 70) | |
| OYZ968 | HPRT1+18.5kR | CCCCAGGCAATTTCCCATCT (SEQ ID NO: 71) | |
| OYZ954 | HPRT1-Forw | TCCTCCTCCTGAGCAGTCA (SEQ ID NO: 72) | PCR for T7E1 assay |

TABLE 1-continued

Oligonucleotides used in this disclosure.

| No. | Oligo Name | Sequence, 5'-3' | Purpose |
|---|---|---|---|
| OYZ955 | HPRT1-AS | GTGACGTAAAGCCGAACCC (SEQ ID NO: 73) | |
| For sgRNA generation | | | |
| OYZ952 | HPRT-guide-F | TAATACGACTCACTATAGTTATGGCGA CCCGCAGCCC (SEQ ID NO: 74) | For GeneArt Precision gRNA (SpyCas9) Synthesis Kit |
| OYZ953 | HPRT-guide-R | TTCTAGCTCTAAAACGGGCTGCGGGTC GCCATAAC (SEQ ID NO: 75) | |
| For Tagmentation and NGS library preparation | | | |
| OYZ507 | Tn5-ME-rev | /5phos/CTGTCTCTTATACACATCT (SEQ ID NO: 76) | Tn5 loading |
| OYZ508 | Tn5-ME-A | TCGTCGGCAGCGTCAGATGTGTATAAG AGACAG (SEQ ID NO: 77) | |
| OYZ510 | Nextera P5 | AATGATACGGCGACCACCGAGATCTAC ACTCGTCGGCAGCGTC (SEQ ID NO: 78) | NGS library prep |
| OYZ511 | EGFP-302-Illumina | GTGACTGGAGTTCAGACGTGTGCTCTT CCGATCTggtcttgtagttgccgtcgt (SEQ ID NO: 79) | |
| N/A | Index primer | CAAGCAGAAGACGGCATACGAGATNN NNGTGACTGGAGTTCAGACGTG TGCT (SEQ ID NO: 80) | |

TABLE 2

EGFP Guide 1 - modifications detected include seamless junctions, deletions with an insertion or partial inversion, deletion with nearby point mutations, pairs of deletions, and duplicated lesions All Sanger Sequencing results for Cascade-G1 + Cas3 editing outcome, in hESCs

| Clone number | deletion size bp | 5' end (relative to ATG of GFP) | 3' end (relative to ATG of GFP) | features at the junction site, etc |
|---|---|---|---|---|
| 1 | 2511 | −2377 | 134 | |
| 2 | 4355 | −4200 | 155 | |
| 3 | 2059 | −2048 | 11 | |
| 4 | 3910 | −3702 | 208 | |
| 5 | 2691 | −2593 | 98 | |
| 6 | 3075 | −2972 | 103 | |
| 7 | 3093 | −3005 | 88 | |
| 8 | 2623 | −2621 | 2 | |
| 9 | 7978 | −7800 | 178 | |
| 10 | 7961 | −7691 | 270 | 1 bp insertion (A) |
| 11 | 7290 | −7236 | 54 | |
| 12 | 7724 | −7631 | 93 | |
| 13 | 8079 | −7923 | 156 | 1 nt mutation/SNP @ 2 nt 5' of junction |
| 14 | 7155 | −7069 | 86 | 1 nt mutation/SNP @ 4 nt 5' of junction |
| 15 | 4279 | −4272 | 7 | |
| 16 | 3455 | −3255 | 200 | 18 bp insertion (CAGTGCTTCAGCCGCTAC (SEQ ID NO: 81)) matches to 208 to 225, downstream of the deletion site |

TABLE 2-continued

EGFP Guide 1 - modifications detected include seamless junctions,
deletions with an insertion or partial inversion, deletion with nearby point mutations, pairs of
deletions, and duplicated lesions All Sanger Sequencing results for Cascade-G1 + Cas3 editing outcome, in hESCs

| Clone number | deletion size bp | 5' end (relative to ATG of GFP) | 3' end (relative to ATG of GFP) | features at the junction site, etc |
|---|---|---|---|---|
| 17 | 4031 | -3867 | 164 | with a concurrent small deletion +275 to +284 (9 nt). |
| 18 | 4375 | -4294 | 81 | |
| 19 | 3027 | -2994 | 33 | |
| 20 | 4379 | -4373 | 6 | |
| 21 | 4079 | -4156 | -77 | |
| 22 | 3780 | -3591 | 189 | |
| 23 | 4208 | -4178 | 30 | 290 bp insertion matches to inverted and deleted region -1440 to -1727 with two internal 1 bp insertion within this 290 bp region. 290 nt insertion is (GGCTCCCTGTAGGCTTCAACTCCCAGGG CTTCAGTGATCCTCCAGCTGGGCCCACA GGTGTGTGCCACCAGGTGTGGCTAATTTT TTGTAGAAACAGAGTCTGGCTATGTTGC CCAGGCTGGCCTCAAACTCCTGGCCTCA AGGGGATCCTCCCAACCTCAGCATCTCA AACCAGGGTACCTTCTAGAAGCCACACC TTGTATTGCGGGCTCCAAGCTGCACTGGC GCCACTGGCATCGCCCACCAGGGGGCAC CGTGAGCTCAGTCTGATGAGCCCAGTGG CGCCCCCA) (SEQ ID NO: 82) |
| 24 | 4358 | -4305 | 53 | |
| 25 | 3214 | -3073 | 141 | |
| 26 | 3084 | -2950 | 134 | |
| 27 | 4275 | -4289 | -14 | |
| 28 | 5316 | -5463 | -147 | with insertion of 161 bp. 154 bp of this insertion matches to the inverted and deleted sequence of -2113 to -2266. 161 bp insertion is (GGCATGCGCCACCACGCCCAGCTGATTT TTGTATTTTTAGTAGAGACAGGTTTCACC ATGTTGGCCAGGATGGTCTCGATGTCTTG TCCTCGTGATCTGCCCACCTCAGCCTACC AAAGTGCTGGGATTACAGGCGTGAGCCA CCACACCCGGCTGACCTA) (SEQ ID NO: 83) |
| 29 | 7344 | -7348 | -4 | |
| 30 | 3877 | -3997 | -120 | |
| 31 | 4338 | -4266 | 72 | |
| 32 | 3921 | -3878 | 43 | |
| 33 | 4252 | -4129 | 123 | 12 bp insertion (GTTGACCACCTG) (SEQ ID NO: 84) |
| 34 | | -3478 | 292 | There are two deletions (middle piece is 572 nt). One deletion from -1363 to 292, another and from -1935 to -3478 |
| 35 | 4398 | -4319 | 79 | |
| 36 | 3625 | -3624 | 1 | |

TABLE 2-continued

EGFP Guide 1 - modifications detected include seamless junctions,
deletions with an insertion or partial inversion, deletion with nearby point mutations, pairs of
deletions, and duplicated lesions All Sanger Sequencing results for Cascade-G1 + Cas3 editing outcome, in hESCs

| Clone number | deletion size bp | 5' end (relative to ATG of GFP) | 3' end (relative to ATG of GFP) | features at the junction site, etc |
|---|---|---|---|---|
| 37 | 3812 | -3716 | 96 | |
| 38 | 3351 | -3350 | 1 | |
| 39 | 18927 | -18985 | -58 | There are two deletions (middle piece is 286 nt), the first one from -58 to -2793, the second is from -3080 to -18985. |
| 40 | 3097 | -3048 | 49 | |
| 41 | 8263 | -8180 | 83 | |
| 42 | 11286 | -11276 | 10 | There are two deletions (middle piece is 298 nt), the first one from 10 to -10784, the second is from -11084 to -11276 |
| 43 | 11722 | -11705 | 17 | |
| 44 | 12323 | -12168 | 155 | |
| 45 | 4222 | -4123 | 99 | |
| 46 | 1549 | -1426 | 123 | |
| 47 | 19875 | -20001 | -126 | There are two deletions (middle piece is 39 nt), the first one from -126 to -16458, the second is from -16499 to -20001. |
| 48 | 8201 | -7989 | 212 | |
| 49 | 18810 | -18853 | -43 | |
| 50 | 11378 | -11336 | 42 | |
| 51 | 20835 | -20693 | 142 | |
| 52 | 2342 | -2350 | -8 | |
| 53 | 11368 | -11093 | 275 | |
| 54 | 5289 | -5275 | 14 | |
| 55 | 2588 | -2512 | 76 | |
| 56 | 2240 | -2113 | 127 | |
| 57 | 1214 | -1199 | 15 | |
| 58 | 1677 | -1491 | 186 | |
| 59 | 8644 | -8582 | 62 | |
| 60 | 767 | -621 | 146 | |
| 61 | 2449 | -2444 | 5 | |
| 62 | 2413 | -2230 | 183 | |
| 63 | 3175 | -3103 | 72 | |
| 64 | 10720 | -10636 | 84 | |
| 65 | 8165 | -8118 | 47 | |
| 66 | 8970 | -8811 | 159 | |
| 67 | 9783 | -9640 | 143 | |

TABLE 2-continued

EGFP Guide 1 - modifications detected include seamless junctions,
deletions with an insertion or partial inversion, deletion with nearby point mutations, pairs of
deletions, and duplicated lesions All Sanger Sequencing results for Cascade-G1 +
Cas3 editing outcome, in hESCs

| Clone number | deletion size bp | 5' end (relative to ATG of GFP) | 3' end (relative to ATG of GFP) | features at the junction site, etc |
|---|---|---|---|---|
| 68 | 4024 | −3908 | 116 | T to G mutation 3 bp 5' to the junction site (pink) |
| 69 | 18142 | −18032 | 110 | |
| 70 | 6155 | −6052 | 103 | |
| 71 | 19221 | −18954 | 267 | |
| 72 | 2460 | −2433 | 27 | |
| 73 | 4927 | −4824 | 103 | |
| 74 | 3956 | −3796 | 160 | 1 bp mutation 1 bp 5' of junction site (pink) |
| 75 | 668 | −622 | 46 | |
| 76 | 9225 | −9166 | 59 | |
| 77 | 4199 | −4191 | 8 | |
| 78 | 859 | −723 | 136 | |
| 79 | | | 111 | only see the junction with an partial inversion (matches to inverted −1517 to −1349), cannot see the other side of the deletion (due to sequencing length). |
| 80 | 11114 | −11164 | −50 | |
| 81 | 18739 | −19027 | −288 | |
| 82 | 12392 | −12267 | 125 | There are two deletions (middle piece is 289 nt), the first one from 125 to −10130, the second one from −10420 to −12267 |
| 83 | 7067 | −6999 | 68 | There are two deletions (middle piece is 154 nt), the first one from 68 to −5437, the second one from −5592 to −6999 |
| 84 | 10782 | −10647 | 135 | |
| 85 | | | 72 | detected the junction with a partial inversion (matches to inverted −6825 to −6712). other end of the deletion not detected due to sequencing length. |
| 86 | | | 160 | detected the junction with a partial inversion (matches to inverted (−498 to −988), other end of the deletion not detected due to sequencing length.. |
| 87 | 8517 | −8348 | 169 | |
| 88 | 11844 | −11771 | 73 | 1 bp insertion (A) at the junction site and 1 bp mutation 4 nt 5'of junction |
| 89 | 4716 | −4521 | 195 | 2 bp insertion (AC) |
| 90 | 4234 | −4236 | −2 | |
| 91 | 11145 | −10843 | 302 | |
| 92 | 2223 | −2227 | −4 | 1 bp insertion (T) |
| 93 | 2341 | −2350 | −9 | |
| 94 | 8114 | −8042 | 72 | |

TABLE 2-continued

EGFP Guide 1 - modifications detected include seamless junctions,
deletions with an insertion or partial inversion, deletion with nearby point mutations, pairs of
deletions, and duplicated lesions All Sanger Sequencing results for Cascade-G1 +
Cas3 editing outcome, in hESCs

| Clone number | deletion size bp | 5' end (relative to ATG of GFP) | 3' end (relative to ATG of GFP) | features at the junction site, etc |
|---|---|---|---|---|
| 95 | 11253 | -11113 | 140 | |
| 96 | 667 | -590 | 77 | |
| 97 | 2684 | -2577 | 107 | insertion of 418 bp, this insertion maps to inverted and deleted sequence from -904 to -1321 418 bp insertion is (TCCCCCTAGGGAGACTGGGGAGCTCACC TTCTAGAAAAAGAAAACTGACATCCAGA CTAGGTTATTCTCCAAGGTCATATAGCCC ATCTAAGAGGTAGGGCCAGGATTAGATA GAGAACGAGTAAAAAACTTCAGGGCATA AATCCCCGCTGAAACCGAGTTTTCCAAG TCACTTGCCTTTGCTTTTTGTTCCACCTTT GGTTGGCAAAAATATTATAAAAGCCTAG GCATAATGAGACCTCCAGGCCCCCATCC CTGAACCACAAACAGCTCCAGGTCACTC ACACCACACCCTTGTGTCCTGGAACCGT GCCTGGGAAAAGCTTCCCCAATAAGCTG CTGCCATATGCACCGGGCCTCCCTGCCTC GGGCTCCATCGTGGAGACATACCAGCCC CTGCCAGACAACCCGTGCTAGC)) (SEQ ID NO: 85) |
| 98 | 12380 | -12254 | 126 | |
| 99 | 1309 | -1255 | 54 | |
| 100 | 4731 | -4649 | 82 | |
| 101 | 7041 | -6942 | 99 | |
| 102 | 2556 | -2384 | 172 | There are two deletions (middle piece is 874 nt), one from 172 to -686 and one from -1560 to -2384 |
| 103 | 8405 | -8127 | 278 | There are two deletions (middle piece 179 nt), one from -8126 to 30, 2nd from 208 to 278 (with 2 nt insertion). |
| 104 | 20714 | -20595 | 119 | |
| 105 | 4161 | -4166 | -5 | |
| 106 | 3246 | -3126 | 120 | |
| 107 | 12190 | -12141 | 49 | |
| 108 | 8285 | -8124 | 161 | |
| 109 | 7725 | -7721 | 4 | |
| 110 | 1873 | -1706 | 167 | with an 281 nt insertion of sequence matchs to inverted and deleted sequence from -1379 to -1660. One point mutation at junction. With a concurrent small indel 4 bp deletion from 272 to 275. insertion is (ATCTATCTTAGAGACAGGGTCTCACTTG GTCACCCAGGCTGGAGTGCAGTGGCGTG ATCACGGCTCCCTGTAGGCTTCAACTCCC AGGGCTTCAGTGATCCTCCAGCTGGGCC CACAGGTGTGTGCCACCAGGTGTGGCTA ATTTTTTGTAGAAACAGAGTCTGGCTATG TTGCCCAGGCTGGCCTCAAACTCCTGGCC TCAAGGGATCCTCCCACCTCAGCATCTCA AACCAGGGTACCTTCTAGAAGCCACACC TTGTATTGCGGGCTCCAAGCTGCAC) (SEQ ID NO: 86) |

TABLE 2-continued

EGFP Guide 1 - modifications detected include seamless junctions,
deletions with an insertion or partial inversion, deletion with nearby point mutations, pairs of
deletions, and duplicated lesions All Sanger Sequencing results for Cascade-G1 +
Cas3 editing outcome, in hESCs

| Clone number | deletion size bp | 5' end (relative to ATG of GFP) | 3' end (relative to ATG of GFP) | features at the junction site, etc |
|---|---|---|---|---|
| 111 | 4280 | -4186 | 94 | |
| 112 | 5401 | -5355 | 46 | |
| 113 | 5873 | -5886 | -13 | an 361 bp insertion of inverted and deleted sequence from -1508 to -1868 (CAGGTGTGGCTAATTTTTTGTAGAAACA GAGTCTGGCTATGTTGCCCAGGCTGGCCT CAAACTCCTGGCCTCAAGGGATCCTCCC ACCTCAGCATCTCAAACCAGGGTACCTT CTAGAAGCCACACCTTGTATTGCGGGCT CCAAGCTGCACTGGCGCCACTGGCATCG CCCACCAGGGGGCACCGTGAGCTCAGTC TGATGAGCCCAGTGGCGCCCCCAGGCAG AGGTGCAATCTGTGGTGAGAGCTCCCAA TTCCAGACCCTGCACCTGCCCATGGCATG GGGCAACTGGACCTCTGCTGCTACTCCCT GTGTGGCCCAGGAGCCACGCAGGCTACA GTACCATGAACTGAGAGCTGCT) (SEQ ID NO: 87) |
| 114 | 4296 | -4171 | 125 | |
| 115 | 12404 | -12269 | 135 | |
| 116 | 4441 | -4314 | 127 | 2 bp insertion (GG) or 1 bp |
| 117 | 7310 | -7261 | 49 | |
| 118 | 11392 | -11342 | 50 | 1 bp insertion (A) or mutation |
| 119 | 8143 | -7985 | 158 | There are two deletions (middle piece 491 nt), one from 158 to -1043, the other from -1536 to -7985. |
| 120 | 21528 | -21345 | 183 | |
| 121 | 4458 | -4459 | -1 | |
| 122 | 7791 | -7728 | 63 | |
| 123 | 7132 | -7053 | 79 | |
| 124 | 4593 | -4545 | 48 | |
| 125 | 5778 | -5683 | 95 | |
| 126 | 4102 | -3989 | 113 | |
| 127 | 2398 | -2123 | 275 | 1 bp insertion (C) or mutation |
| 128 | 11809 | -11530 | 279 | |
| 129 | 6695 | -6627 | 68 | |
| 130 | 5146 | -4934 | 212 | |
| 131 | 2945 | -2872 | 73 | |
| 132 | 3586 | -3426 | 160 | |
| 133 | 4219 | -4174 | 45 | insertion of 8 bp (CGGCGATT) |
| 134 | 4553 | -4510 | 43 | |
| 135 | 1219 | -1102 | 117 | |
| 136 | 11470 | -11350 | 120 | |

TABLE 2-continued

EGFP Guide 1 - modifications detected include seamless junctions,
deletions with an insertion or partial inversion, deletion with nearby point mutations, pairs of
deletions, and duplicated lesions All Sanger Sequencing results for Cascade-G1 +
Cas3 editing outcome, in hESCs

| Clone number | deletion size bp | 5' end (relative to ATG of GFP) | 3' end (relative to ATG of GFP) | features at the junction site, etc |
|---|---|---|---|---|
| 137 | 1531 | −1507 | 24 | |
| 138 | 11113 | −11164 | −51 | |
| 139 | 18145 | −18131 | 14 | |
| 140 | 1489 | −1265 | 224 | |
| 141 | 4274 | −4116 | 158 | 3 bp insertion (CGT) |
| 142 | 789 | −601 | 188 | |
| 143 | 7372 | −7374 | −2 | |
| 144 | 7829 | −7830 | −1 | |
| 145 | 1485 | −1407 | 78 | |
| 146 | 8297 | −8232 | 65 | |
| 147 | 5957 | −5911 | 46 | |
| 148 | 11523 | −11402 | 121 | |
| 149 | 6793 | −6801 | −8 | |
| 150 | 5965 | −5840 | 125 | |
| 151 | 2462 | −2305 | 157 | |
| 152 | 11763 | −11483 | 280 | |
| 153 | 6032 | −5964 | 68 | One 289 nt insertion matches to inverted and deleted sequence from −2468 to −2180. The 289 nt insertion is (GGATGGTCTCGATGTCTTGTCCTCGTGATCTGCCCACCTCAGCCTACCAAAGTGCTGGGATTACAGGCGTGAGCCACCACACCCGGCCTGAAGCGGGATTTTCACAAGACATTTTAACACACACAAGTCATGCCTAGGTGATTAATATGCATGTTAAAGCAGCATTGTTCAGATTATAAACATGTGCGCTGATACATAACACATAGGCTTTCTGTGCCTTCACATGATCCAGAGTGTGTATCAGCACCTGTTAAGGAATTTCCCCTACCAAGGACAAGGGACGTGCCTGA) (SEQ ID NO: 88) |
| 154 | 2019 | −1982 | 37 | |
| 155 | 4840 | −4560 | 280 | |
| 156 | 8232 | −8074 | 158 | |
| 157 | 19980 | −19891 | 89 | |
| 158 | 15797 | −15612 | 185 | there are two deletions (middle piece is 907 nt), first from 185 tp −15612, the second from −16519 to −20333 |
| 159 | 11918 | −11705 | 213 | |
| 160 | 20152 | −20072 | 80 | |
| 161 | 6306 | −6178 | 128 | |
| 162 | 11081 | −10961 | 120 | |
| 163 | 5578 | −5294 | 284 | |

TABLE 2-continued

EGFP Guide 1 - modifications detected include seamless junctions,
deletions with an insertion or partial inversion, deletion with nearby point mutations, pairs of
deletions, and duplicated lesions All Sanger Sequencing results for Cascade-G1 +
Cas3 editing outcome, in hESCs

| Clone number | deletion size bp | 5' end (relative to ATG of GFP) | 3' end (relative to ATG of GFP) | features at the junction site, etc |
|---|---|---|---|---|
| 164 | 20382 | -20115 | 267 | 6 bp insertion (CAAGTC) |
| 165 | 12245 | -12080 | 165 | 2 bp insertion (AA) |
| 166 | 5384 | -5311 | 73 | There are two deletions, one from 73 to -5311 and one from -5491 to -11552 (with an insertion in the second deletion matches to -2831 to -3292) |
| 167 | 2219 | -2188 | 31 | |
| 168 | 20849 | -21315 | -466 | |
| 169 | 7836 | -7711 | 125 | 8 bp insertion (AGGGTGTG) |
| 170 | 619 | -498 | 121 | |
| 171 | 7957 | -7853 | 104 | |
| 172 | 4381 | -4166 | 215 | |
| 173 | 11548 | -11384 | 164 | |
| 174 | 1296 | -1266 | 30 | |
| 175 | 1707 | -1560 | 147 | |
| 176 | 3774 | -3534 | 240 | There is a complicated insertion of 193 bp. Part of it map to -4314 to -4398, upstream of the deleted region, the other part is not mappable (define as unclear) The 193 nt insertion is (TAAAACGACGGCCAGTGAATTGTAATAC GACTCACTATAGGGNGAATTGGGCCCTC TAGATGCATGCTCGAGCGGCCGCCAGTG TGATGGATATCTGCAGAATTCGCCCTTGA TGGGGTGGGGGTTAAAGGAGGTGGCAGA CAGNCTGGGTGCAGTGGCTCACGCCTGT AATCCCAGGCCAAGGCGAGTAGAT) (SEQ ID NO: 89) |
| 177 | 8519 | -8434 | 85 | 2 bp insertion (TC) |
| 178 | 5012 | -4927 | 85 | |
| 179 | 7999 | -7964 | 35 | |
| 180 | 18430 | -18799 | -369 | |
| | 20382 | -20115 | 267 | The same as clone 164 |
| | 12404 | -12269 | 135 | The same as clone 115 |
| | 12323 | -12168 | 155 | The same as clone 44 |
| | 12323 | -12168 | 155 | The same as clone 44 |
| | 12323 | -12168 | 155 | The same as clone 44 |
| | 12245 | -12080 | 165 | The same as clone 165 |
| | 12245 | -12080 | 165 | The same as clone 165 |
| | 11722 | -11705 | 17 | The same as clone 43 |
| | 11470 | -11350 | 120 | The same as clone 136 |
| | 10782 | -10647 | 135 | The same as clone 84 |
| | 8201 | -7989 | 212 | The same as Clone 48 |
| | 8201 | -7989 | 212 | The same as Clone 48 |
| | 7725 | -7721 | 4 | The same as clone 109 |
| | 5957 | -5911 | 46 | The same as clone 147 |
| | 5965 | -5840 | 125 | The same as clone 150 |
| | 5289 | -5275 | 14 | The same as clone 54 |
| | 4375 | -4294 | 81 | The same as clone 18 |
| | 4338 | -4266 | 72 | The same as clone 31 |
| | 4219 | -4174 | 45 | The same as clone 133 |
| | 4381 | -4166 | 215 | The same as clone 172 |
| | 4079 | -4156 | -77 | The same as clone 21 |

TABLE 2-continued

EGFP Guide 1 - modifications detected include seamless junctions,
deletions with an insertion or partial inversion, deletion with nearby point mutations, pairs of
deletions, and duplicated lesions All Sanger Sequencing results for Cascade-G1 +
Cas3 editing outcome, in hESCs

| Clone number | deletion size bp | 5' end (relative to ATG of GFP) | 3' end (relative to ATG of GFP) | features at the junction site, etc |
|---|---|---|---|---|
| | 4024 | -3908 | 116 | The same as clone 68 |
| | 4024 | -3908 | 116 | The same as clone 68 |
| | 3867 | -3867 | | The same as clone 17 |
| | 3867 | -3867 | | The same as clone 17 |
| | 3351 | -3350 | 1 | The same as clone 38 |
| | 3455 | -3255 | 200 | The same as clone 16 |
| | 2460 | -2433 | 27 | The same as cone 72 |
| | 2341 | -2350 | -9 | The same as clone 93 |
| | 2219 | -2188 | 31 | The same as clone 167 |
| | 1549 | -1426 | 123 | The same as clone 46 |
| | 1485 | -1407 | 78 | The same as clone 145 |
| | 1214 | -1199 | 15 | The same as clone 57 |
| | 859 | -723 | 136 | The same as clone 78 |
| | 767 | -621 | 146 | The same as clone 60 |

Blue: Group I  (a seamless junction)

Orange: Group II  (a deletion with an insertion or partial inversion)

Pink: Group III  (a deletion with nearby point mutation[s])

green: Group IV  (two deletions)

yellow: duplicated lesions

TABLE 2 continued - EGFP Guide 2

All Sanger Sequencing results for Cascade-G2 + Cas3
editing outcome, in hESCs

| Clone number | deletion size bp | 5' end (relative to ATG of GFP) | 3' end (relative to ATG of GFP) | |
|---|---|---|---|---|
| 1 | 580 | 738 | 1317 | |
| 2 | 604 | 466 | 1069 | |
| 3 | 2740 | 568 | 3307 | with additional 2bp deletion at 3461-3462 |
| 4 | 39 | 586 | 624 | |
| 5 | | 644 | N/A | Sequence not long enough to see downstream flanking sequence. Partial inverted insertion mapped to sequence 3812 to 4277 |
| 6 | 1814 | 446 | 2259 | |
| 7 | 4404 | 490 | 4893 | There are two deletions (middle piece is 217nt), one from 490 to 4040 and the ther from 4258 to 4893. |
| 8 | 840 | 554 | 1393 | |
| 9 | 1707 | 628 | 2334 | |
| 10 | 4680 | 801 | 5480 | |
| 11 | 3921 | 509 | 4429 | |
| 12 | 4113 | 635 | 4747 | |
| 13 | 4925 | 508 | 5432 | |
| 14 | 4613 | 802 | 5414 | |
| 15 | 2835 | 652 | 3486 | one mutation at 649 |
| 16 | 7991 | 588 | 8578 | two deletions (middle piece is 441nt), one from 588 to 2166 and the other from |

TABLE 2-continued continued - EGFP Guide 2

All Sanger Sequencing results for Cascade-G2 + Cas3 editing outcome, in hESCs

| Clone number | deletion size bp | 5' end (relative to ATG of GFP) | 3' end (relative to ATG of GFP) | |
|---|---|---|---|---|
| | | | | 2608 to 8580. |
| 17 | 8811 | 516 | 9326 | |
| 18 | 8717 | 724 | 9440 | 2bp insertion at junction (CA) |
| 19 | 8282 | 562 | 8843 | |
| 20 | 7770 | 835 | 8604 | |
| 21 | 7514 | 577 | 8090 | |
| 22 | 4034 | 445 | 4478 | |
| 23 | 4530 | 517 | 5046 | |
| | 3921 | 509 | 4429 | The same as clone 11 |
| | 580 | 738 | 1317 | The same as clone 1 |
| | 580 | 738 | 1317 | The same as clone 1 |
| | 39 | 586 | 624 | The same as clone 4 |
| | 4113 | 635 | 4747 | The same as clone 12 |
| | 1814 | 446 | 2259 | The same as clone 6 |
| | 8811 | 516 | 9326 | The same as clone 17 |
| | 1814 | 446 | 2259 | The same as clone 6 |
| | 8282 | 562 | 8843 | The same as clone 19 |
| | 4925 | 508 | 5432 | The same as clone 13 |
| | 4034 | 445 | 4478 | The same as clone 22 |
| | 4925 | 508 | 5432 | The same as clone 13 |
| | 840 | 554 | 1393 | The same as clone 8 |
| | 2740 | 568 | 3307 | The same as clone 3 |
| | 580 | 738 | 1317 | The same as clone 1 |
| | 4404 | 490 | 4893 | The same as clone 7 |
| | 8282 | 562 | 8843 | The same as clone 19 |
| | 3921 | 509 | 4429 | The same as clone 11 |
| | 8811 | 516 | 9326 | The same as clone 17 |
| | 8282 | 562 | 8843 | The same as clone 19 |
| | 4925 | 508 | 5432 | The same as clone 13 |
| | 3921 | 509 | 4429 | The same as clone 11 |
| | 3921 | 509 | 4429 | The same as clone 11 |
| | 4404 | 490 | 4893 | The same as clone 7 |

Blue: (a seamless junction)
Group I
Orange: (a deletion with an insertion or partial inversion)
Group II
Pink: (a deletion with nearby point mutation[s])
Group III
green: (two deletions)
Group IV
yellow: duplicated lesions

TABLE 2 continued - EGFP Guide 1 - Single Clone

Figure 2:
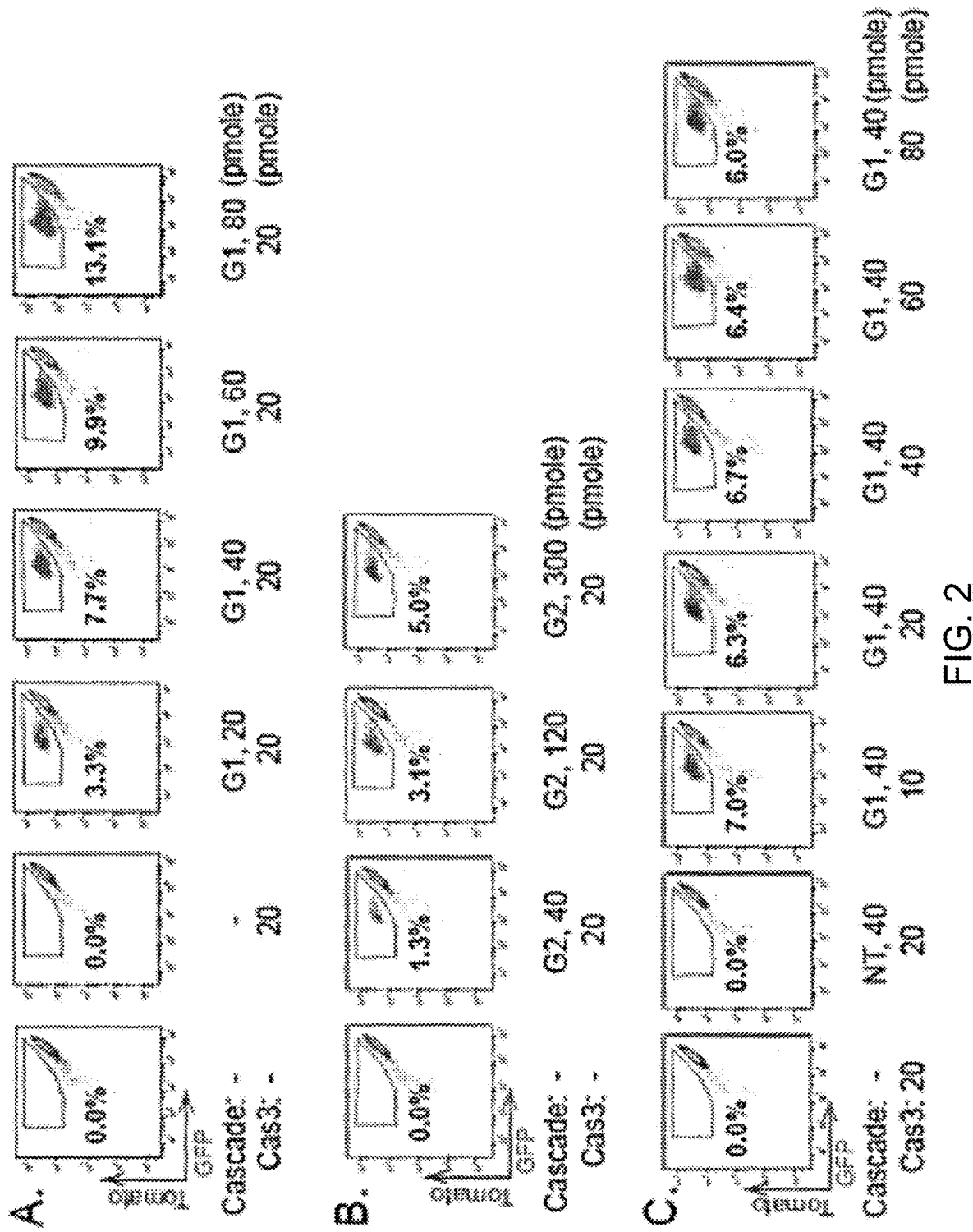
FIG. 2. Optimization of genome editing efficiency. (A-C) Flow cytometry analysis of dual-reporter hESC line 4 days after RNP delivery. Increasing amount of TfuCascade-G1 or TfuCascade-G2 was used in conjunction with constant Tfu-Cas3 in (A) and (B). Increasing amount of TfuCas3 was used in conjunction with constant amount of TfuCascade-G1 in (C). Percentages of EGFP-negative/tdTomato-positive cells (boxed) are indicated. Amounts of Cascade or Cas3 delivered via 10 µL electroporation reactions were indicated.

Sanger Sequencing results for hESC single Cell isolated from the Cascade-G1 + Cas3 editing experiment in FIG. 1

| Clone number | deletion size bp | 5' end (relative to ATG of GFP) | 3' end (relative to ATG of GFP) | note - features at the junction site, etc |
|---|---|---|---|---|
| 1 | 5425 | −5373 | 52 | |
| 2 | 10831 | −10755 | 76 | |
| 3 | 6020 | −5823 | 197 | |
| 4 | Lesion not identified using tiling PCR primers within 20 kb upstream of the target site | | | |
| 5 | Lesion not identified using tiling PCR primers within 20 kb upstream of the target site | | | |
| 6 | Lesion not identified using tiling PCR primers within 20 kb upstream of the target site | | | |

TABLE 2-continued continued - EGFP Guide 1 - Single Clone

Sanger Sequencing results for hESC single
Cell isolated from the Cascade-G1 + Cas3
editing experiment in FIG. 1

| Clone number | deletion size bp | 5' end (relative to ATG of GFP) | 3' end (relative to ATG of GFP) | note - features at the junction site, etc |
|---|---|---|---|---|
| 7 | Lesion not identified using tiling PCR primers within 20 kb upstream of the target site | | | |
| 8 | 15143 | −14936 | 207 | there are two deletions, one from −14936 to −10489 and then from −9835 to 207 |
| 9 | Lesion not identified using tiling PCR primers within 20 kb upstream of the target site | | | |
| 10 | 293 | −185 | 108 | |
| 11 | Lesion not identified using tiling PCR primers within 20 kb upstream of the target site | | | |
| 12 | 2059 | −2048 | 11 | |
| 13 | 4415 | −4317 | 98 | |
| 14 | 18599 | −18459 | 140 | |
| 15 | 5425 | −5373 | 52 | |

TABLE 3

Top off-target sites predicted in silico.

| Chr No. | Location (+1 position) | DNA sequence | Real mis-matches (nts) |
|---|---|---|---|

Prediction Rule: NAG PAM (enlarged) (−3, −2, −1), strict seed-proximal region (1-5, 7-11), allows kinked position (enlarged and bold) mismatches (allowed (italics)) changes from the intended target sequence). Real mismatches (lowercase) for off-target scoring.
HPRT-Guide 1
Positions in the target −3-2-1, 1, etc.

| Chr No. | Location (+1 position) | DNA sequence | Real mis-matches (nts) |
|---|---|---|---|
| | | AAGACCTTGCACTACCTGTGGCTTCCATTTTCCTG (SEQ ID NO: 90) | 0 |
| chr5 | −126070373 | CAGACCTTTCACTACtTtTtGCaTCaCTTTTtTTG (SEQ ID NO: 91) | 6 |
| chr13 | 35649591 | TAGACCTTTCACTAACTaTGTtaTtCCTTTTgTct (SEQ ID NO: 92) | 7 |
| chr1 | 168106111 | CAGACCTTTCACTAACTcaGCtTcCCTgcTTtGTa (SEQ ID NO: 93) | 8 |
| chr1 | 248282311 | GAGACCTTTCACTACCctgGTtagCtGTaTTCTTG (SEQ ID NO: 94) | 8 |
| chr10 | 16331362 | AAGACCTTCCACTATtataaTgcTaCTTTTTaGTG (SEQ ID NO: 95) | 9 |
| chr11 | 43569243 | GAGACCTTCCACTAGtTGCCCCTTCCCcTaaaAac (SEQ ID NO: 96) | 9 |
| chr1 | 171938222 | AAGACCTTTCACTATCaGaGGtTgaaATTcTaATa (SEQ ID NO: 97) | 9 |
| chr12 | −2124242 | AAGACCTTTCACTATtTGaaACaACtGTTTaCAgt (SEQ ID NO: 98) | 9 |
| chr14 | −89247537 | AAGACCTTGCACTAGacaTcCtTTCCTgTccCCTt (SEQ ID NO: 99) | 9 |

HPRT-Guide 2

| | | AAGAAGCCGAGGCTCCCCCAGCGAAGCCCCTTTCC (SEQ ID NO: 100) | 0 |

TABLE 3-continued

Top off-target sites predicted in silico.

| Chr No. | Location (+1 position) | DNA sequence | Real mis-matches (nts) |
|---|---|---|---|
| chrX | 119872140 | TAGAAGCCGAGGCTTgCgaAACGAAGCCCgaTAga (SEQ ID NO: 101) | 7 |
| chr11 | 115357182 | CAGAAGCCCAGGCTCCCCCAaGgcaTtCgcTCCt (SEQ ID NO: 102) | 8 |
| chr11 | -3834326 | GAGAAGCCAAGGCTTCagtACtGAAGGgCaTgTaC (SEQ ID NO: 103) | 8 |
| chr11 | 76216772 | CAGAAGCCCAGGCTGgggCAGaGAgaGgCCTTGCt (SEQ ID NO: 104) | 8 |
| chr1 | 20571497 | AAGAAGCCCAGGCTGgCCtgCtGgAGACaCgTGtC (SEQ ID NO: 105) | 8 |
| chr18 | -44950655 | CAGAAGCCAAGGCTTtCtCtGgcAtGAtCtTTTCC (SEQ ID NO: 106) | 8 |
| chr19 | 21706580 | GAGAAGCCCAGGCTTCCCagCCagccTCCCTcTgC (SEQ ID NO: 107) | 8 |
| chr19 | -21679212 | GAGAAGCCCAGGCTTCCCagCCagccTCCCTcTgC (SEQ ID NO: 108) | 8 |
| chr22 | 47623743 | GAGAAGCCCAGGCTCCCagAGgGAgtGagCTgCCC (SEQ ID NO: 109) | 8 |
| chr2 | 310871 | GAGAAGCCAAGGCTGCCaaACaGGAGTaaaTTCaC (SEQ ID NO: 110) | 8 |
| EGFP-Guide 1 | | | |
| | | AAGGCTACGTCCAGGAGCGCACCATCTTCTTCAAG (SEQ ID NO: 111) | 0 |
| chr18 | 72745808 | AAGGCTACCTCCAGAcaCtgCCCAgCATCgTCAtt (SEQ ID NO: 112) | 8 |
| chr3 | 3365960 | TAGGCTACTTCCAGTAaCtCCCCAaaGTCaTgGga (SEQ ID NO: 113) | 8 |
| chr10 | -15534764 | CAGGCTACGTCCAGGcaCaCACCAatTagaTtGAG (SEQ ID NO: 114) | 9 |
| chr11 | 34459775 | GAGGCTACATCCAGGAGCtgCCCATgGcaggaTtG (SEQ ID NO: 115) | 9 |
| chr14 | -25606088 | TAGGCTACATCCAGAcatGaAtaAgCATgTTCCtG (SEQ ID NO: 116) | 9 |
| chr14 | 94531563 | AAGGCTACTTCCAGAAGtGaTCacatCaCTTCTgc (SEQ ID NO: 117) | 9 |
| chr2 | 108277531 | AAGGCTACCTCCAGCccCaCACtAcCTTCTctGgc (SEQ ID NO: 118) | 9 |
| chr5 | 54116354 | CAGGCTACATCCAGAcaCtaTCCATaTgCTTgAga (SEQ ID NO: 119) | 9 |
| chr6 | 151151366 | CAGGCTACTTCCAGAtGtaCTgacTCAgtcTCTAG (SEQ ID NO: 120) | 9 |
| chrX | 132111946 | CAGGCTACATCCAGGAatctCagAaCTTCTTgAgG (SEQ ID NO: 121) | 9 |
| Tomato-Guide | | | |
| | | AAGCTGGACATCACCTCCCACAACGAGGACTACAC (SEQ ID NO: 122) | 0 |
| chr13 | 70297924 | GAGCTGGAGATCACCTgCtgGCAgagGGACTACcC (SEQ ID NO: 123) | 8 |

TABLE 3-continued

Top off-target sites predicted in silico.

| Chr No. | Location (+1 position) | DNA sequence | Real mis-matches (nts) |
|---|---|---|---|
| chr17 | -60057863 | CAGCTGGACATCACATgCaAAAAaaAAaAtgAGtC (SEQ ID NO: 124) | 8 |
| chr2 | 191730355 | AAGCTGGAAATCACATCCagGAgtGgAGAacAGAt (SEQ ID NO: 125) | 8 |
| chr9 | 3030572 | CAGCTGGATATCACCataCAGAttGtGcACTgTAC (SEQ ID NO: 126) | 8 |
| chr9 | 96177069 | AAGCTGGAAATCACAgCCCACggCcAAatCcAGcC (SEQ ID NO: 127) | 8 |
| chr15 | 99719558 | TAGCTGGAAATCACTcCatAGAgtGATtAgTtCAt (SEQ ID NO: 128) | 9 |
| chr2 | -231107949 | TAGCTGGATATCACAcaaaATAACaAGaACTtGga (SEQ ID NO: 129) | 9 |
| chr2 | 40686339 | TAGCTGGATATCACCTagagCAAtGAGaACcATtg (SEQ ID NO: 130) | 9 |
| chrX | -107542293 | GAGCTGGAGATCACTgCagAAAgtGATtACagTAt (SEQ ID NO: 131) | 9 |
| EGFP-Guide 2 | | | |
| | | AAGTCGATGCCCTTCAGCTCGATGCGGTTCACCAG (SEQ ID NO: 132) | 0 |
| chr1 | 150751811 | GAGTCGATGCCCTTGttaTCAATGatGTaCtgGAa (SEQ ID NO: 133) | 9 |
| chr3 | 124493138 | GAGTCGATTCCCTTAAGagCCATctaATagtCAtG (SEQ ID NO: 134) | 9 |
| chr9 | 126108685 | AAGTCGATCCCCTTTgcCcCAATtCcCTcaACAct (SEQ ID NO: 135) | 9 |
| chr11 | -81604887 | AAGTCGATACCCTTCAGgaaAgTGCtAagCAaGgG (SEQ ID NO: 136) | 9 |

Discussion

Figure 3:
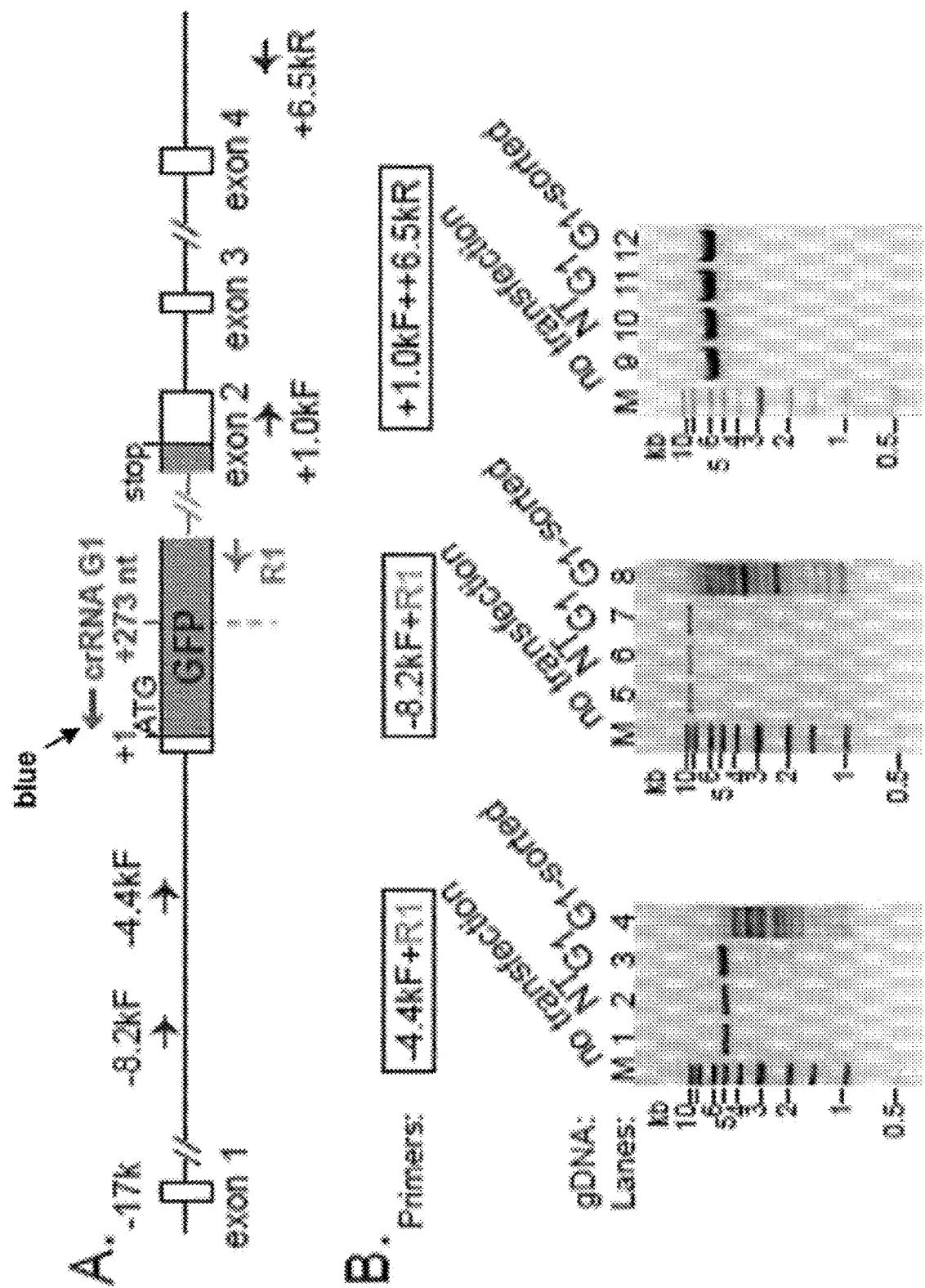
FIG. 3. Long-range PCR based characterization of genomic lesions induced by Type I CRISPR-Cas. (A) (C) Schematic of the DNMT3B-EGFP locus and annealing sites for five PCR primers used in (B) or ten PCR primers used in (D). Positions relative to the EGFP translation start site (+1) are indicated. Recognition sites ($2^{nd}$ nt of the PAM) for Cascade-G1 are marked by the dashed line. Blue arrowhead, direction of Cas3 translocation. (B) Characterization of genomic lesions by long-range PCRs. A collection of DNA lesions was introduced upstream of GFP by a GFP-targeting Cascade-G1 and Cas3, in the sorted EGFP-negative/tdTomato-positive population, as well as in unsorted total cells. NT, total cells treated with a non-targeting Cascade and Cas3. PCR primers used are indicated and their annealing sites depicted in (A). (D) Heterogeneous large genomic deletions were introduced by Cascade-G1/Cas3 in the ~20 kb region upstream of GFP, revealed by serial long-range PCRs with tiling forward primers. NT, non-targeting Cascade. PCR primers used are indicated and their annealing sites depicted in (C). M, DNA size markers.
Figure 3:
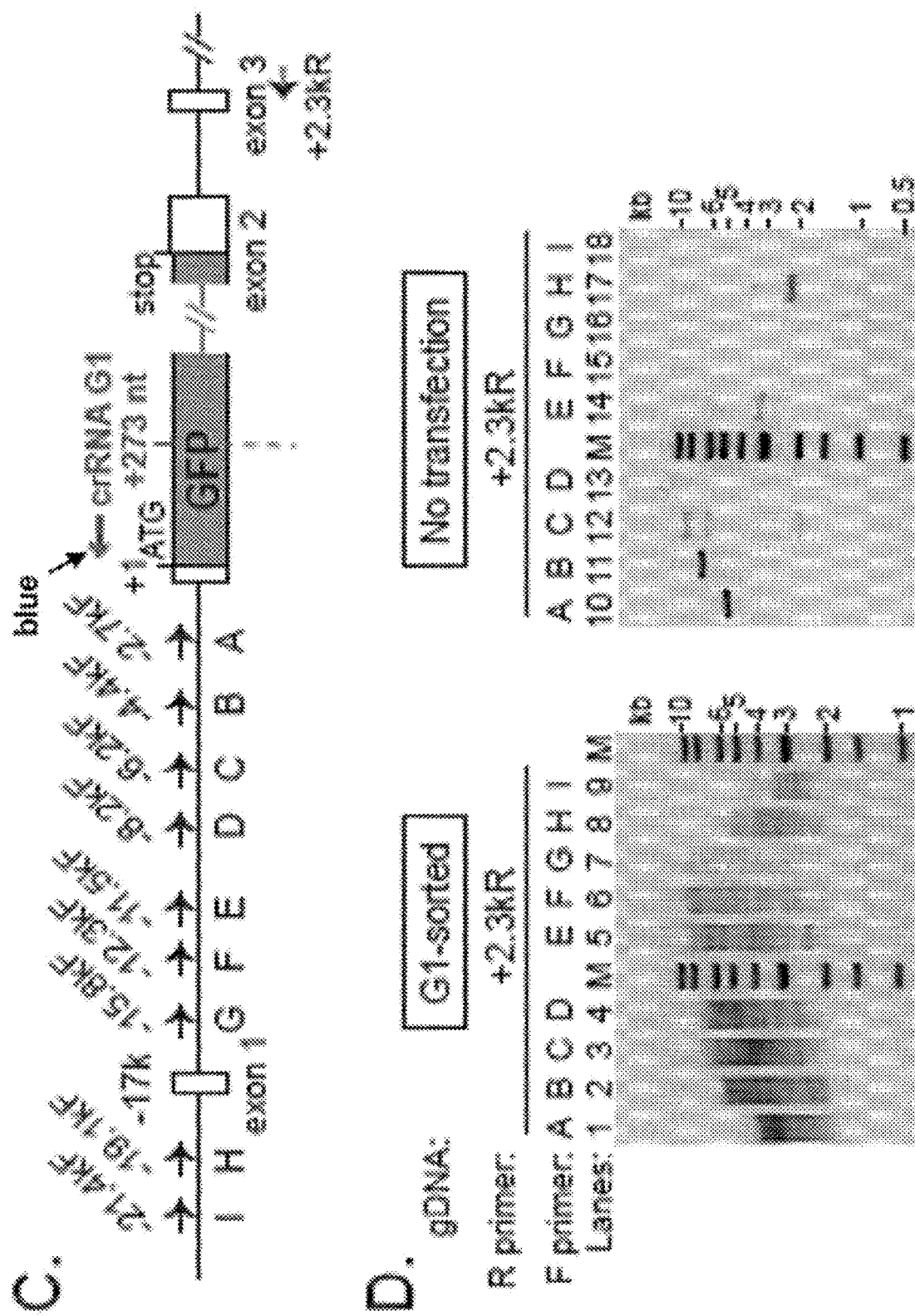

In its native environment, Type I CRISPR interference typically eradicates the targeted foreign DNA completely, and may cause cell death if accidentally programmed against the prokaryotic host genome. In this disclosure, the large chromosome size and strong intrinsic NHEJ activity of human cells allowed observation of the unique deletion/repair outcome for Type I CRISPR in a heterologous eukaryotic context. The phenomenon of Cas3-mediated human genome editing over a long distance is quite different from the localized editing by Cas9 and Cas12 at the CRISPR-targeted site. Unexpectedly, Cas3 and a single guide-programmed Cascade together lead to a spectrum of large chromosomal deletions in a hESC population. The heterogeneity manifests in the number of unique lesion junctions observed (180 out of 217 by Sanger sequencing), as well as the wide distribution of deletion sizes and distal endpoints (FIGS. 3-5, 11, and Table 2). The onsets of deletions were not uniform either, spreading out within a predictable ~400 bp region upstream of target site. Moreover, Cas3-induced lesions are predominantly large deletions, with very rare small indels (FIGS. 3-4, 11, and Table 2).

In comparison, current gene-editors Cas9 and Cas12 cause precise genomic breaks inside the CRISPR-complementary target site. NHEJ repair of these breaks will eventually lead to small indels that change the original target sequence and therefore may prevent any further targeting by the same guide. We found that the vast majority of the DNA deletions by Type I CRISPR do not affect the sequence integrity of the target site (FIGS. 4 and 11, Table 2). This implies that prolonged exposure to Type I CRISPR machinery will likely enable iterative rounds of DNA deletion and repair, which could create extremely large chromosomal deletions. This could allow tuning of the final deletion outcome, through the control of Type I CRISPR gene expression in cells, or through the choice of different delivery methods.

It was recently reported that in addition to small indels, CRISPR-Cas9 may also cause rare distal deletions and complex chromosomal rearrangements around the target site in mESCs (Kosicki et al., 2018). However, the large genomic deletions from the presently provided Type I CRISPR edited hESCs are clearly of a different nature. They are unidirectional, occur at high frequency, are not accompanied by small indel formation, and have a predictable range of onset points.

Because of its long-range impact, the final products of Type I CRISPR mediated DNA degradation were difficult to define in prokaryotes. Insights have been obtained from single molecule studies (Blosser et al., 2015; Dillard et al., 2018; Krivoy et al., 2018; Loeff et al., 2018; Redding et al., 2015; Rutkauskas et al., 2015; Szczelkun et al., 2014). A single molecule DNA curtain study of the *E. coli* Type I-E system revealed two modes of action after Cas3 has been recruited to the R-loop region by Cascade and nicked the non-target strand DNA (Redding et al., 2015). First, Cas3 reels DNA towards itself while bound to Cascade. It then dissociates from Cascade and translocates along dsDNA for kilobases (Loeff et al., 2018; Redding et al., 2015). ssDNA is exposed to various extents during these processes, however, DSB formation was not observed (Redding et al., 2015).

The present disclosure indicates that in human cells, Cas3 presumably generates multiple DSBs during DNA translocation, and the distal deletion boundary likely reflects the last DSB by Cas3. An unexpected finding from a mechanistic perspective, was that the onsets of the deletions were never exactly at the first Cas3 nicking site, which is on the non-target strand DNA inside the R-loop region (Mulepati and Bailey, 2013; Sinkunas et al., 2013; Xiao et al., 2017). Rather, they were distributed within a ~400 bp window in the PAM-proximal region, indicating that Cas3 may not elicit the first DSBs during the very initial phase of its translocation on human genome.

As discussed above, the disclosure includes ~13% genome editing efficiency ex vivo in hESCs and 30-60% efficiencies in HAP1 cells through transient Type I RNP delivery. Additional data demonstrate up to 96% efficiencies. The disclosure includes further improving TfuCascade's activity at 37° C. through structure-guided engineering or directed evolution, and by employing plasmid/mRNA-based delivery to increase effector concentration and persistence, as demonstrated herein.

Off-target effect is a concern for all genome editing applications. Previous work suggests that tolerance of mismatches by TfuCascade only gradually increases beyond the first 8-nt "seed" region (Jung et al., 2017). This behaviour is similar to that of Cas12 (Strohkendl et al., 2018), but stands in contrast from Cas9 (Boyle et al., 2017). Off-targeting for Type I CRISPR is further suppressed at the Cas3 recruitment step, by a large conformational change in Cascade upon full R-loop formation (Hochstrasser et al., 2014; Wiedenheft et al., 2011; Xiao et al., 2018). Data presented herein indicate that the Type I CRISPR-mediated genome editing is quite stringent. The robust HPRT targeting by Cascade/Cas3 in HAP1 cells is completely abrogated by a point mutation at the 5' end of the crRNA spacer (FIG. 6E). Furthermore, informatic prediction suggests that off-targeting in the human genome is unlikely.

More than 98% of the human genome is non-coding, containing cis-elements important for gene regulation and diseases. Yet, prior to the present disclosure, effective genetic tools to characterize these large regions are limited. Large genome deletion is typically achieved by programming CRISPR-Cas9 with a pair of sgRNA guides dictating the deletion boundaries (Canver et al., 2014; Chen et al., 2014; Cong et al., 2013). Cas9-based screening methods also allow high-throughput functional interrogation of the non-coding genome, which typically involves the laborious design of a tiling library of sgRNA or sgRNA pairs (Diao et al., 2017; Fulco et al., 2016; Komor et al., 2017). The ability of Type I CRISPR to generate such a diverse range of large deletions from a single CRISPR-targeted site could enable long-range CRISPR screens that are more simple and cost-effective to execute, because far fewer guides are needed and each guide leads to a library of deletion mutants. These approaches could be adapted to erase parasitic or diseased genetic elements, or to introduce long-range epigenetic modifications.

REFERENCES

This reference listing in not an indication that any particular reference is material to patentability.

Barrangou, R., Fremaux, C., Deveau, H., Richards, M., Boyaval, P., Moineau, S., Romero, D. A., and Horvath, P. (2007). CRISPR provides acquired resistance against viruses in prokaryotes. Science 315, 1709-1712.

Blosser, T. R., Loeff, L., Westra, E. R., Vlot, M., Kunne, T., Sobota, M., Dekker, C., Brouns, S. J. J., and Joo, C. (2015). Two distinct DNA binding modes guide dual roles of a CRISPR-Cas protein complex. Mol Cell 58, 60-70.

Bolger, A. M., Lohse, M., and Usadel, B. (2014). Trimmomatic: a flexible trimmer for Illumina sequence data. Bioinformatics 30, 2114-2120.

Bolotin, A., Quinquis, B., Sorokin, A., and Ehrlich, S. D. (2005). Clustered regularly interspaced short palindrome repeats (CRISPRs) have spacers of extrachromosomal origin. Microbiology 151, 2551-2561.

Boyle, E. A., Andreasson, J. O. L., Chircus, L. M., Sternberg, S. H., Wu, M. J., Guegler, C. K., Doudna, J. A., and Greenleaf, W. J. (2017). High-throughput biochemical profiling reveals sequence determinants of dCas9 off-target binding and unbinding. Proceedings of the National Academy of Sciences of the United States of America 114, 5461-5466.

Brinkman, E. K., Chen, T., Amendola, M., and van Steensel, B. (2014). Easy quantitative assessment of genome editing by sequence trace decomposition. Nucleic Acids Res 42, e168.

Brouns, S. J., Jore, M. M., Lundgren, M., Westra, E. R., Slijkhuis, R. J., Snijders, A. P., Dickman, M. J., Makarova, K. S., Koonin, E. V., and van der Oost, J. (2008). Small CRISPR RNAs guide antiviral defense in prokaryotes. Science 321, 960-964.

Caliando, B. J., and Voigt, C. A. (2015). Targeted DNA degradation using a CRISPR device stably carried in the host genome. Nature communications 6, 6989.

Canver, M. C., Bauer, D. E., Dass, A., Yien, Y. Y., Chung, J., Masuda, T., Maeda, T., Paw, B. H., and Orkin, S. H. (2014). Characterization of genomic deletion efficiency mediated by clustered regularly interspaced short palindromic repeats (CRISPR)/Cas9 nuclease system in mammalian cells. The Journal of biological chemistry 289, 21312-21324.

Chen, X., Xu, F., Zhu, C., Ji, J., Zhou, X., Feng, X., and Guang, S. (2014). Dual sgRNA-directed gene knockout using CRISPR/Cas9 technology in *Caenorhabditis elegans*. Sci Rep 4, 7581.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Diao, Y., Fang, R., Li, B., Meng, Z., Yu, J., Qiu, Y., Lin, K. C., Huang, H., Liu, T., Marina, R. J., et al. (2017). A tiling-deletion-based genetic screen for cis-regulatory element identification in mammalian cells. Nature methods 14, 629-635.

Dillard, K. E., Brown, M. W., Johnson, N. V., Xiao, Y., Dolan, A., Hernandez, E., Dahlhauser, S. D., Kim, Y., Myler, L. R., Anslyn, E. V., et al. (2018). Assembly and Translocation of a CRISPR-Cas Primed Acquisition Complex. Cell.

Fineran, P. C., Gerritzen, M. J., Suarez-Diez, M., Kunne, T., Boekhorst, J., van Hijum, S. A., Staals, R. H., and Brouns, S. J. (2014). Degenerate target sites mediate rapid primed CRISPR adaptation. Proceedings of the National Academy of Sciences of the United States of America 111, E1629-1638.

Fulco, C. P., Munschauer, M., Anyoha, R., Munson, G., Grossman, S. R., Perez, E. M., Kane, M., Cleary, B., Lander, E. S., and Engreitz, J. M. (2016). Systematic mapping of functional enhancer-promoter connections with CRISPR interference. Science 354, 769-773.

Geissmann, Q. (2013). OpenCFU, a new free and open-source software to count cell colonies and other circular objects. PLoS One 8, e54072.

Guschin, D. Y., Waite, A. J., Katibah, G. E., Miller, J. C., Holmes, M. C., and Rebar, E. J. (2010). A rapid and general assay for monitoring endogenous gene modification. Methods Mol Biol 649, 247-256.

Hayes, R. P., Xiao, Y., Ding, F., van Erp, P. B., Rajashankar, K., Bailey, S., Wiedenheft, B., and Ke, A. (2016). Structural basis for promiscuous PAM recognition in type I-E Cascade from *E. coli*. Nature 530, 499-503.

Hochstrasser, M. L., Taylor, D. W., Bhat, P., Guegler, C. K., Sternberg, S. H., Nogales, E., and Doudna, J. A. (2014). CasA mediates Cas3-catalyzed target degradation during CRISPR RNA-guided interference. Proceedings of the National Academy of Sciences of the United States of America 111, 6618-6623.

Huo, Y., Nam, K. H., Ding, F., Lee, H., Wu, L., Xiao, Y., Farchione, M. D., Jr., Zhou, S., Rajashankar, K., Kurinov, I., et al. (2014). Structures of CRISPR Cas3 offer mechanistic insights into Cascade-activated DNA unwinding and degradation. Nature structural & molecular biology 21, 771-777.

Jackson, R. N., Golden, S. M., van Erp, P. B., Carter, J., Westra, E. R., Brouns, S. J., van der Oost, J., Terwilliger, T. C., Read, R. J., and Wiedenheft, B. (2014). Crystal structure of the CRISPR RNA-guided surveillance complex from *Escherichia coli*. Science 345, 1473-1479.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Jung, C., Hawkins, J. A., Jones, S. K., Jr., Xiao, Y., Rybarski, J. R., Dillard, K. E., Hussmann, J., Saifuddin, F. A., Savran, C. A., Ellington, A. D., et al. (2017). Massively Parallel Biophysical Analysis of CRISPR-Cas Complexes on Next Generation Sequencing Chips. Cell 170, 35-47 e13.

Kim, S., Kim, D., Cho, S. W., Kim, J., and Kim, J. S. (2014). Highly efficient RNA-guided genome editing in human cells via delivery of purified Cas9 ribonucleoproteins. Genome Res 24, 1012-1019.

Knott, G. J., and Doudna, J. A. (2018). CRISPR-Cas guides the future of genetic engineering. Science 361, 866-869.

Komor, A. C., Badran, A. H., and Liu, D. R. (2017). CRISPR-Based Technologies for the Manipulation of Eukaryotic Genomes. Cell 169, 559.

Kosicki, M., Tomberg, K., and Bradley, A. (2018). Repair of double-strand breaks induced by CRISPR-Cas9 leads to large deletions and complex rearrangements. Nature biotechnology 36, 765-771.

Krivoy, A., Rutkauskas, M., Kuznedelov, K., Musharova, O., Rouillon, C., Severinov, K., and Seidel, R. (2018). Primed CRISPR adaptation in *Escherichia coli* cells does not depend on conformational changes in the Cascade effector complex detected in Vitro. Nucleic acids research 46, 4087-4098.

Kunne, T., Kieper, S. N., Bannenberg, J. W., Vogel, A. I., Miellet, W. R., Klein, M., Depken, M., Suarez-Diez, M., and Brouns, S. J. (2016). Cas3-Derived Target DNA Degradation Fragments Fuel Primed CRISPR Adaptation. Molecular cell 63, 852-864.

Kurtz, S., Phillippy, A., Delcher, A. L., Smoot, M., Shumway, M., Antonescu, C., and Salzberg, S. L. (2004). Versatile and open software for comparing large genomes. Genome biology 5, R12.

Li, Y., Pan, S., Zhang, Y., Ren, M., Feng, M., Peng, N., Chen, L., Liang, Y. X., and She, Q. (2016). Harnessing Type I and Type III CRISPR-Cas systems for genome editing. Nucleic acids research 44, e34.

Loeff, L., Brouns, S. J. J., and Joo, C. (2018). Repetitive DNA Reeling by the Cascade-Cas3 Complex in Nucleotide Unwinding Steps. Molecular cell 70, 385-394 e383.

Luo, M. L., Mullis, A. S., Leenay, R. T., and Beisel, C. L. (2015). Repurposing endogenous type I CRISPR-Cas systems for programmable gene repression. Nucleic acids research 43, 674-681.

Makarova, K. S., Grishin, N. V., Shabalina, S. A., Wolf, Y. I., and Koonin, E. V. (2006). A putative RNA-interference-based immune system in prokaryotes: computational analysis of the predicted enzymatic machinery, functional analogies with eukaryotic RNAi, and hypothetical mechanisms of action. Biol Direct 1, 7.

Makarova, K. S., and Koonin, E. V. (2015). Annotation and Classification of CRISPR-Cas Systems. Methods in molecular biology 1311, 47-75.

Makarova, K. S., Wolf, Y. I., Alkhnbashi, O. S., Costa, F., Shah, S. A., Saunders, S. J., Barrangou, R., Brouns, S. J., Charpentier, E., Haft, D. H., et al. (2015). An updated evolutionary classification of CRISPR-Cas systems. Nature reviews Microbiology 13, 722-736.

Mali, P., Yang, L., Esvelt, K. M., Aach, J., Guell, M., DiCarlo, J. E., Norville, J. E., and Church, G. M. (2013). RNA-guided human genome engineering via Cas9. Science 339, 823-826.

Marraffini, L. A., and Sontheimer, E. J. (2008). CRISPR interference limits horizontal gene transfer in staphylococci by targeting DNA. Science 322, 1843-1845.

Martin, M. (2011). Cutadapt removes adapter sequences from high-throughput sequencing reads. EMBnetjournal; Vol 17, No 1: Next Generation Sequencing Data Analysis.

Mojica, F. J., Garcia-Martinez, J., and Soria, E. (2005). Intervening sequences of regularly spaced prokaryotic repeats derive from foreign genetic elements. Journal of molecular evolution 60, 174-182.

Mulepati, S., and Bailey, S. (2013). In vitro reconstitution of an *Escherichia coli* RNA-guided immune system reveals unidirectional, ATP-dependent degradation of DNA target. The Journal of biological chemistry 288, 22184-22192.

Mulepati, S., Heroux, A., and Bailey, S. (2014). Crystal structure of a CRISPR RNA-guided surveillance complex bound to a ssDNA target. Science 345, 1479-1484.

Picelli, S., Bjorklund, A. K., Reinius, B., Sagasser, S., Winberg, G., and Sandberg, R. (2014). Tn5 transposase and tagmentation procedures for massively scaled sequencing projects. Genome Res 24, 2033-2040.

Pourcel, C., Salvignol, G., and Vergnaud, G. (2005). CRISPR elements in *Yersinia pestis* acquire new repeats by preferential uptake of bacteriophage DNA, and provide additional tools for evolutionary studies. Microbiology 151, 653-663.

Rath, D., Amlinger, L., Hoekzema, M., Devulapally, P. R., and Lundgren, M. (2015). Efficient programmable gene silencing by Cascade. Nucleic acids research 43, 237-246.

Redding, S., Sternberg, S. H., Marshall, M., Gibb, B., Bhat, P., Guegler, C. K., Wiedenheft, B., Doudna, J. A., and Greene, E. C. (2015). Surveillance and Processing of Foreign DNA by the *Escherichia coli* CRISPR-Cas System. Cell 163, 854-865.

Rutkauskas, M., Sinkunas, T., Songailiene, I., Tikhomirova, M. S., Siksnys, V., and Seidel, R. (2015). Directional R-Loop Formation by the CRISPR-Cas Surveillance Complex Cascade Provides Efficient Off-Target Site Rejection. Cell reports.

Sashital, D. G., Wiedenheft, B., and Doudna, J. A. (2012). Mechanism of foreign DNA selection in a bacterial adaptive immune system. Molecular cell 46, 606-615.

Semenova, E., Jore, M. M., Datsenko, K. A., Semenova, A., Westra, E. R., Wanner, B., van der Oost, J., Brouns, S. J., and Severinov, K. (2011). Interference by clustered regularly interspaced short palindromic repeat (CRISPR) RNA is governed by a seed sequence. Proceedings of the National Academy of Sciences of the United States of America 108, 10098-10103.

Shmakov, S., Abudayyeh, O. O., Makarova, K. S., Wolf, Y. I., Gootenberg, J. S., Semenova, E., Minakhin, L., Joung, J., Konermann, S., Severinov, K., et al. (2015). Discovery and Functional Characterization of Diverse Class 2 CRISPR-Cas Systems. Molecular cell 60, 385-397.

Sinkunas, T., Gasiunas, G., Waghmare, S. P., Dickman, M. J., Barrangou, R., Horvath, P., and Siksnys, V. (2013). In vitro reconstitution of Cascade-mediated CRISPR immunity in *Streptococcus thermophilus*. EMBO J 32, 385-394.

Sperger, J. M., Chen, X., Draper, J. S., Antosiewicz, J. E., Chon, C. H., Jones, S. B., Brooks, J. D., Andrews, P. W., Brown, P. O., and Thomson, J. A. (2003). Gene expression patterns in human embryonic stem cells and human pluripotent germ cell tumors. Proceedings of the National Academy of Sciences of the United States of America 100, 13350-13355.

Strohkendl, I., Saifuddin, F. A., Rybarski, J. R., Finkelstein, I. J., and Russell, R. (2018). Kinetic Basis for DNA Target Specificity of CRISPR-Cas12a. Mol Cell 71, 816-824 e813.

Szczelkun, M. D., Tikhomirova, M. S., Sinkunas, T., Gasiunas, G., Karvelis, T., Pschera, P., Siksnys, V., and Seidel, R. (2014). Direct observation of R-loop formation by single RNA-guided Cas9 and Cascade effector complexes. Proceedings of the National Academy of Sciences of the United States of America 111, 9798-9803.

Westra, E. R., van Erp, P. B., Kunne, T., Wong, S. P., Staals, R. H., Seegers, C. L., Bollen, S., Jore, M. M., Semenova, E., Severinov, K., et al. (2012). CRISPR immunity relies on the consecutive binding and degradation of negatively supercoiled invader DNA by Cascade and Cas3. Mol Cell 46, 595-605.

Wiedenheft, B., Lander, G. C., Zhou, K., Jore, M. M., Brouns, S. J., van der Oost, J., Doudna, J. A., and Nogales, E. (2011). Structures of the RNA-guided surveillance complex from a bacterial immune system. Nature 477, 486-489.

Xiao, Y., Luo, M., Dolan, A. E., Liao, M., and Ke, A. (2018). Structure basis for RNA-guided DNA degradation by Cascade and Cas3. Science 361.

Xiao, Y., Luo, M., Hayes, R. P., Kim, J., Ng, S., Ding, F., Liao, M., and Ke, A. (2017). Structure Basis for Directional R-loop Formation and Substrate Handover Mechanisms in Type I CRISPR-Cas System. Cell 170, 48-60 e11.

Zetsche, B., Gootenberg, J. S., Abudayyeh, O. O., Slaymaker, I. M., Makarova, K. S., Essletzbichler, P., Volz, S. E., Joung, J., van der Oost, J., Regev, A., et al. (2015). Cpf1 is a single RNA-guided endonuclease of a class 2 CRISPR-Cas system. Cell 163, 759-771.

Zhao, H., Sheng, G., Wang, J., Wang, M., Bunkoczi, G., Gong, W., Wei, Z., and Wang, Y. (2014). Crystal structure of the RNA-guided immune surveillance Cascade complex in *Escherichia coli*. Nature 515, 147-150.

Zuris, J. A., Thompson, D. B., Shu, Y., Guilinger, J. P., Bessen, J. L., Hu, J. H., Maeder, M. L., Joung, J. K., Chen, Z. Y., and Liu, D. R. (2015). Cationic lipid-mediated delivery of proteins enables efficient protein-based genome editing in vitro and in vivo. Nat Biotechnol 33, 73-80.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A method of modifying DNA in eukaryotic cells, the method comprising introducing into the eukaryotic cells:
   (i) a combination of proteins comprising Cas3, Cse1/CasA, Cse2/CasB, Cas7/CasC, Cas5e/CasD and Cas6e/CasE, each comprising an amino acid sequence that is at least 85% homologous across its entire length to a Thermobifida Fusca (T. fusca) protein, wherein the Cas3 protein comprises the sequence of SEQ ID NO: 1 or a sequence that is at least 85% homologous across its entire length to the sequence of SEQ ID NO: 1, wherein the sequence of the Cse2/CasB protein comprises or a sequence that is at least 85-99% homologous across the entire length sequence of SEQ ID NO: 2, wherein the sequence that is at least 85-99% homologous to the sequence of SEQ ID NO: 2 comprises an amino acid at position 23 of SEQ ID NO: 2 that is not an N, and wherein the modification of the DNA is performed at a temperature of about 37° C.;
   (ii) a guide RNA (a targeting RNA) comprising a sequence that is complementary to a targeted site in a segment of the DNA, the targeted site comprising a spacer sequence; and
   (iii) allowing the combination of the proteins and the guide RNA to modify the DNA by nicking, causing a double stranded break (DSB), and/or unidirectional deleting of a single strand of the DNA, wherein the targeted site is not modified, and wherein the DNA is comprised by a chromosome or an extrachromosomal element.

2. The method of claim 1, wherein the unidirectional deleting occurs.

3. The method claim 1, wherein the eukaryotic cells are in a population of eukaryotic cells in an in vitro cell culture.

4. The method of claim 3, wherein the segment of the DNA is modified in 10%-100% of the cells in the in vitro cell culture.

5. The method of claim 1, wherein the DNA is comprised by a chromosome.

6. The method of claim 1, wherein modifying the segment of the DNA comprises a deletion of from about 500 nucleotides to about 100,000 nucleotides.

7. The method of claim 1, wherein the DNA is comprised by a chromosome, the method further comprising introducing a DNA repair template into the eukaryotic cells such that the sequence of the DNA repair template is incorporated into the chromosome.

8. The method of claim 7, wherein incorporation of the sequence of the DNA repair template comprises introducing a mutation into the eukaryotic chromosomes.

9. The method of claim 8, wherein the mutation comprises an insertion or a deletion of one or more nucleotides relative to the sequence of the segment of the DNA prior to its modification.

10. The method of claim 1, wherein the guide RNA and at least one of the proteins are introduced into the eukaryotic cells as a ribonucleoprotein (RNP) complex.

11. The method of claim 1, wherein at least one of the proteins is introduced into the eukaryotic cells by expression from an expression vector, or by introducing into the eukaryotic cells mRNA encoding the at least one protein.

12. The method of claim 1, further comprising determining the sequence of the segment of the DNA to identify a modification.

13. The method of claim 1, further comprising repeating steps i), ii) and iii) in the same eukaryotic cells using the same or a distinct targeting RNA.

14. The method of claim 1, wherein the eukaryotic cells are human cells.

15. The method of claim 14, wherein the human cells comprise totipotent, pluripotent or multipotent stem cells.

16. A eukaryotic cell made by a method of claim 1.

17. A non-human animal comprising a eukaryotic cell of claim 16.

18. A kit comprising the combination of proteins of claim 1 (i) or one or more polynucleotides that can express the combination of proteins, the kit optionally further comprising the targeting RNA or the DNA polynucleotide that expresses the targeting RNA of claim 1 (ii).

19. The kit of claim 18, further comprising instructions for modifying DNA at a temperature of at least about 37° C.

* * * * *

SEQUENCE LISTING

```
<160> NUMBER OF SEQ ID NOS: 148

<210> SEQ ID NO 1
<211> LENGTH: 943
<212> TYPE: PRT
<213> ORGANISM: Thermobifida fusca

<400> SEQUENCE: 1

Pro Glu His Asp Ser Thr Asp Asp Lys His Gly Ile Pro Pro Leu Asp
1               5                   10                  15

Leu Arg Phe Trp Ala Lys Glu Arg Gly Leu Arg Gly Lys Thr Tyr Pro
            20                  25                  30

Leu Val Cys His Ser Leu Asp Ala Ala Ala Ala Leu Val Leu Trp
        35                  40                  45

Asn Glu Tyr Leu Ser Pro Gly Leu Arg Asp Thr Ile Ala Ser Ser Met
    50                  55                  60

Glu Thr Asp Glu Glu His Ala Gly His Cys Ile Ala Phe Trp Ala Gly
65                  70                  75                  80
```

```
Leu His Asp Ile Gly Lys Leu Thr Arg Glu Phe Gln Gln Gln Ile Ala
                85                  90                  95

Ile Asp Leu Ser Ala Tyr Pro Gly Glu Glu Leu Ser Gly Glu Gln Arg
            100                 105                 110

Ser His Ala Ala Ala Thr Gly Lys Trp Leu Pro Phe Ala Leu Pro Ser
        115                 120                 125

Leu Gly Tyr Pro Asn Gly Gly Leu Val Thr Gly Leu Val Ala Gln Met
    130                 135                 140

Leu Gly Gly His His Gly Thr Phe His Pro His Pro Ser Phe Gln Ser
145                 150                 155                 160

Arg Asn Pro Leu Ala Glu Phe Gly Phe Ser Ser Pro His Trp Glu Lys
                165                 170                 175

Gln Arg His Ala Leu Leu His Ala Val Phe Asp Ala Thr Gly Arg Pro
            180                 185                 190

Thr Pro Pro Asp Met Leu Asp Gly Pro Thr Ala Ser Val Val Cys Gly
        195                 200                 205

Leu Val Ile Leu Ala Asp Trp Leu Val Ser Gln Glu Asp Phe Leu Leu
    210                 215                 220

Glu Arg Leu Thr Ser Leu Pro Ala Asp Gly Ser Ala Ser Ala Leu Arg
225                 230                 235                 240

Ala His Phe Glu Thr Ser Leu Arg Arg Ile Pro Ser Leu Leu Asp Ala
                245                 250                 255

Ala Gly Leu Arg Pro Ile Thr Val Pro Pro Ala Thr Phe Thr Glu Ser
            260                 265                 270

Phe Pro His Leu Ser Lys Pro Asn Gly Leu Gln Ala Ser Leu Ala Lys
        275                 280                 285

His Leu Pro Cys Leu Cys Thr Gly Pro Gly Leu Val Leu Ile Thr Ala
    290                 295                 300

Pro Met Gly Glu Gly Lys Thr Glu Ala Ala Tyr His Val Ala Asp Leu
305                 310                 315                 320

Leu Gly Lys Ala Thr Gly Arg Pro Gly Arg Phe Leu Ala Leu Pro Thr
                325                 330                 335

Met Ala Thr Ala Asp Gln Met Thr His Arg Leu Lys Glu Tyr Ala Arg
            340                 345                 350

Tyr Arg Val Glu Asn Thr Asp Leu Pro Arg Ser Ser Thr Leu Ala Leu
        355                 360                 365

Leu His Ser Met Ala Trp Leu Asn Pro Asp Tyr Ala Pro Ala Asp Leu
    370                 375                 380

Pro Gly Val Ser Lys Val Leu Ser Asn Leu Gly His Arg Asp Pro Phe
385                 390                 395                 400

Ala Ala Thr Asp Trp Leu Met Gly Arg Lys Arg Gly Leu Leu Ala Pro
                405                 410                 415

Trp Ala Val Gly Thr Ile Asp Gln Ala Leu Met Ala Val Leu Arg Ala
            420                 425                 430

Lys His Asn Ala Leu Arg Leu Phe Gly Leu Ala Gly Lys Val Val Val
        435                 440                 445

Val Asp Glu Ala His Ala Val Asp Pro Tyr Met Gln Val Leu Leu Glu
    450                 455                 460

Gln Leu Leu Arg Trp Leu Gly Thr Leu Asp Val Pro Val Val Leu Leu
465                 470                 475                 480

Ser Ala Thr Leu His His Ser Ile Ala Asn Ser Leu Val Lys Ala Tyr
                485                 490                 495
```

Leu Glu Gly Ala Arg Gly Arg Trp Asn Arg Ser Glu Pro Gln Pro
            500                 505                 510

Val Ser Glu Val Ser Tyr Pro Gly Trp Leu His Val Asp Ala Arg Ile
            515                 520                 525

Gly Lys Val Thr Arg Ser Ser Asp Val Asp Pro Leu Pro Ile Ala Thr
            530                 535                 540

Thr Pro Arg Lys Pro Leu Glu Val Arg Leu Val Asp Val Pro Val Lys
545                 550                 555                 560

Glu Gly Ala Leu Asn Arg Ser Thr Val Leu Ala Lys Glu Leu Thr Pro
                565                 570                 575

Leu Val Lys Gln Gly Gly Cys Ala Ala Ile Ile Cys Thr Thr Val Ala
            580                 585                 590

Glu Ala Gln Gly Val Tyr Asp Leu Leu Ser Gln Trp Phe Ala Thr Leu
            595                 600                 605

Gly Glu Asp Ala Pro Asp Leu Tyr Leu Leu His Ser Arg Phe Pro Asn
            610                 615                 620

Arg Gln Arg Thr Glu Ile Thr Ala Thr Ile Val Asp Leu Phe Gly Lys
625                 630                 635                 640

Glu Gly Ala Gln Ser Gly Arg Arg Pro Thr Arg Gly Ala Val Leu Val
                645                 650                 655

Ala Thr Gln Val Val Glu Gln Ser Leu Asp Leu Asp Val Asp Leu Met
            660                 665                 670

Ile Ser Asp Leu Ala Pro Val Ser Leu Leu Gln Arg Ala Gly Arg
            675                 680                 685

Cys Trp Arg His Glu His Leu Gly Ile Ile Asn Arg Pro Gln Trp Ala
            690                 695                 700

Lys Gln Pro Glu Leu Val Val Leu Thr Pro Glu Gln Asn Gly Asp Ala
705                 710                 715                 720

Asp Arg Ala Pro Trp Phe Pro Arg Ser Trp Thr Ser Val Tyr Pro Leu
                725                 730                 735

Ala Leu Leu Gln Arg Thr Tyr Thr Leu Leu Arg Arg Arg Asn Gly Ala
            740                 745                 750

Pro Val Gln Ile Pro Glu Asp Val Gln Gln Leu Val Asp Asp Val Tyr
            755                 760                 765

Asp Asp Asp Ser Leu Ala Glu Asp Leu Glu Ala Asp Met Glu Arg Met
770                 775                 780

Gly Glu Glu Leu Ala Gln Arg Gly Leu Ala Arg Asn Ala Val Ile Pro
785                 790                 795                 800

Asp Pro Asp Asp Ala Glu Asp Asn Leu Asn Gly Leu Thr Glu Phe Ser
                805                 810                 815

Phe Asp Val Asp Glu His Val Leu Ala Thr Arg Phe Gly Ala Gly Ser
            820                 825                 830

Val Arg Val Leu Cys Tyr Tyr Val Asp Thr Ala Gly Asn Arg Trp Leu
            835                 840                 845

Asp Pro Glu Cys Thr Val Glu Phe Pro Glu Gln Gly Thr Gly Arg Glu
            850                 855                 860

Gly Arg Phe Thr Met Ala Asp Cys Arg Asp Leu Val Ala Arg Thr Ile
865                 870                 875                 880

Pro Val Arg Met Gly Pro Trp Ala Ser Gln Leu Thr Glu Asp Asn His
                885                 890                 895

Pro Pro Glu Ala Trp Arg Glu Ser Phe Tyr Leu Arg Asp Leu Val Leu
            900                 905                 910

```
Ile Pro Gln Arg Val Thr Asp Glu Gly Ala Val Leu Pro Thr Glu Thr
            915                 920                 925

Gly Gly Arg Glu Trp Leu Leu Asp Pro Cys Lys Gly Leu Ile Phe
930                 935                 940

<210> SEQ ID NO 2
<211> LENGTH: 244
<212> TYPE: PRT
<213> ORGANISM: Thermobifida fusca

<400> SEQUENCE: 2

Val Asn Ser Asp Tyr Ile Leu Gln His Ala Asp Ala Leu Val Lys Arg
1               5                   10                  15

Val Ser Lys Leu Ile Val Asn Glu Pro Ala Ala Arg Ala Ala Leu Arg
            20                  25                  30

Arg Gly Val Gly Leu Ala Pro Glu Asp Pro Arg Met Leu Ala Ala His
            35                  40                  45

Arg Val Val Ala Pro Tyr Val Pro Val Pro Thr Asp Tyr Asp Val Asp
        50                  55                  60

Arg Arg Arg Ala Ala Ser Leu Trp Asp Val His Ala Val Glu Arg Ala
65                  70                  75                  80

Phe Tyr Ala Val Ala Ala Ile Met Ala Ala Gln Pro Arg Ser Ala Arg
                85                  90                  95

Asp Gln Glu Ala Glu Ala Thr Glu Glu Gln Thr Gly Glu Pro Gln Asp
            100                 105                 110

Ser Glu Ala Leu Thr Glu Pro Thr Pro Ala Glu Glu Ser Ser Ala Thr
        115                 120                 125

Lys Asp Gly Lys Pro Asp Arg Arg Pro Asn Leu Gly Val Ser Leu Ala
    130                 135                 140

Gln Ala Val Phe Asp Lys Gly Leu Asn Ala Asp Ser Thr Glu Gln Arg
145                 150                 155                 160

Leu His Leu Ile Ala Arg Gln Asn Leu Asp Gly Val His Arg His Leu
                165                 170                 175

Pro Arg Leu Val Leu Tyr Leu Arg Ser Asp Gln Val His Ile Asp Trp
            180                 185                 190

Gly Ile Leu Ile Arg Asp Leu Ala Arg Trp Gly His Thr Pro Arg His
        195                 200                 205

Val Ala Arg Glu Trp Val Gln Asp Tyr His Arg Thr Leu Glu Thr Leu
    210                 215                 220

Thr Arg Gln Ala Glu Gln Lys Asn Lys Asn Asn Thr Thr Asp Glu Glu
225                 230                 235                 240

Ala Glu Ala Ala

<210> SEQ ID NO 3
<211> LENGTH: 2832
<212> TYPE: DNA
<213> ORGANISM: Thermobifida fusca

<400> SEQUENCE: 3
cccgaacacg attctacaga tgacaagcac ggtatcccac cgctcgactt gaggttctgg      60
gcgaaagaac gcggccttcg cggcaagacc taccccttgg tgtgccattc cctcgacgct     120
gctgccgcgg cattggtgtt gtggaacgaa tatctctctc ccgggctgcg agacacgatc     180
gcttcgtcta tggagactga cgaagagcac gcgggacact gcatcgcttt ctgggcgggg     240
ttgcatgaca tagggaaact aacccgagag ttcaacagc agatcgctat cgacctttcc     300
```

-continued

```
gcttatcccg gggaggagct cagtggggaa caaaggtccc atgctgccgc gaccggtaaa    360
tggctgccgt tcgcgcttcc ttcactcggc tatcccaacg gaggactagt caccggcctc    420
gttgcccaga tgcttggggg ccatcacggt acgttccacc cacacccctc ttttcaaagc    480
cgcaatccgc tagcggagtt cggcttttcc tcgccgcact gggagaagca gcgccacgcc    540
ctgctgcacg cagttttga tgcgacgggg cgtcccacac ctcctgacat gcttgacggg    600
cctacagcat cggtcgtgtg cggcctggtc atccttgctg actggctggt cagccaggag    660
gattttctcc tggaacgtct cacctccctg cccgcagacg gttccgcgtc tgcactgcgc    720
gcccactttg aaacgtcgct acggcgcatc ccctcacttc tcgacgccgc gggtctacgg    780
ccgatcacag ttcctccggc cacgttcact gagtcgtttc cgcacctgag caagcccaac    840
ggccttcaag catcgttggc gaaacacctt ccttgcctgt gcaccggtcc gggattagtg    900
ctgatcaccg cgcccatggg tgagggcaag accgaagccg cctaccatgt ggcggatctg    960
ctggggaagg caacggggcg ccctggacgt tttcttgcgc ttcccaccat ggccactgct   1020
gaccagatgc acacccggct caaggagtac gcacgctacc gggtggagaa cacagacctt   1080
ccgcgctcct ccacgctggc cctcctgcat tcaatggcgt ggctgaatcc cgactacgcc   1140
cccgccgacc tgccaggcgt gtcgaaagtg ctctctaatc tcgggcaccg cgatccgttt   1200
gccgcaactg actggctgat ggggcgtaaa cggggcctac tcgctccctg ggcagtcggc   1260
acaatcgacc aagcactcat ggcggtgctg cgtgcgaaac acaacgcgct gcgcctgttc   1320
gggcttgctg ggaaagtggt ggttgtcgac gaggcgcacg cggtcgaccc ttacatgcag   1380
gtcctcttgg aacagttgct gcgctggctg gcacgcttg atgtgccggt agtgctgctg   1440
tcggcgacct tgcatcacag catcgcgaac tcacttgtca aggcgtacct ggaaggtgcc   1500
cgaggcagaa ggtggaacag gtctgaaccg cagcctgttt cggaggtctc ctaccctggc   1560
tggctgcacg ttgacgctcg gatcggaaaa gtgactcgca gcagcgacgt cgaccccttg   1620
cctatcgcta cgactccccg caagcccttg gaggtgcggc ttgtggacgt gccggtcaag   1680
gagggagccc taaaccggtc cacggtgctc gctaaggagc tgactccact agtgaagcag   1740
ggaggatgcg cagcgatcat ctgcaccacg gttgctgaag cccagggagt ctacgatctg   1800 cttcccagt ggtttgcgac gctcggtgag gacgccccg accttacct gctgcattcg   1860 cggttcccta accggcagcg cacggagatc accgcgacca tcgttgacct gttcggtaaa   1920
gaaggtgcac agagcggacg gagacccact cgcggcgctg tcctggtagc cacccaagtg   1980
gtggagcagt ccctcgactt ggacgtggat ttgatgatca gcgacctcgc tccagtgtcg   2040
ctgttgctgc aacgggcggg acgctgctgg cggcacgaac acctgggcat catcaaccgt   2100
ccccaatggg ccaaacagcc cgagcttgtg gtactcaccc cggaacagaa cggcgacgct   2160
gatagggctc cgtggtttcc gcgttcctgg acatcggtgt acccgctggc attgctccag   2220
cgcacgtaca cactgctgcg ccgcaggaac ggggccccgg tgcagattcc tgaagacgtg   2280
cagcagcttg tggacgacgt gtatgacgac gactcgctcg ctgaagatct agaagcagac   2340
atggagcgca tgggggagga gctggcacaa cgcggcttgg cgcgcaacgc ggtcatcccc   2400
gacccagacg atgcggaaga caacctgaac gggctcaccg agttcagctt tgatgtggac   2460
gagcacgtgc tcgcgacccg gttcggtgcc ggttcagtcc gggtgttgtg ctactacgtg   2520
gacacgcgcg ggaaccgctg gcttgaccct gaatgcacgg tcgagtttcc tgaacagggc   2580
acggggcgag agggccggtt caccatgcga gactgccgcg acctggtggc ccgcacgatc   2640
ccggtgcgta tgggtccctg ggcgagtcaa ctcaccgagg acaaccatcc tcctgaggca   2700
```

-continued

```
tggcgggagt cgttctacct tcgcgacctg gttcttatac ctcaacgtgt gacagacgag    2760
ggcgcggtgc tccccactga aaccggtgga cgagagtggt tgcttgatcc ctgtaagggg    2820
ctgatctttt aa                                                        2832
```

<210> SEQ ID NO 4
<211> LENGTH: 42
<212> TYPE: PRT
<213> ORGANISM: Artificial Sequence
<220> FEATURE:
<223> OTHER INFORMATION: C terminal 2xHA-NLS Tag

<400> SEQUENCE: 4

```
Cys Lys Gly Leu Ile Phe Gly Ser Val Gly Tyr Pro Tyr Asp Val Pro
1               5                   10                  15

Asp Tyr Ala Gly Tyr Pro Tyr Asp Val Pro Asp Tyr Ala Gly Ser Tyr
            20                  25                  30

Pro Glu Phe Pro Lys Lys Lys Arg Lys Val
        35                  40
```

<210> SEQ ID NO 5
<211> LENGTH: 42
<212> TYPE: PRT
<213> ORGANISM: Artificial Sequence
<220> FEATURE:
<223> OTHER INFORMATION: N-terminal Twin-Strep-HRV

<400> SEQUENCE: 5

```
Met Trp Ser His Pro Gln Phe Glu Lys Gly Gly Gly Ser Gly Gly Gly
1               5                   10                  15

Ser Gly Gly Ser Ala Trp Ser His Pro Gln Phe Glu Lys Leu Glu Val
            20                  25                  30

Leu Phe Gln Gly Pro Val Pro Glu His Asp
        35                  40
```

<210> SEQ ID NO 6
<211> LENGTH: 1650
<212> TYPE: DNA
<213> ORGANISM: Thermobifida fusca

<400> SEQUENCE: 6

```
gtgctgtcgg ttgccctgtg ttttcttgtg ggaggagcca ttccttcacc gccgtcattt     60
gatgtgacca tcgctccttg gctgattgcg cgcagccgcg acgtcctggc cgcacccgaa    120
atgctgggac tgcgtgacgt tctcatccgc tcccacgaac tctccgacgt ggagattccg    180
cttccgcctg gcgcggcagt actgtggcgg atactcgcac tgatcaccgc ccgcatcacc    240
ggcctcgacc agccgccaaa caagaatccg aagcggaaat gcaggctcg ccgcagccag     300 atcctcagca aggacgact cgacccggaa gcggtcgacg cctacttcgc cgactactcg    360
gagcgcttcg acctgttcca ccctgagcgg ccctggttgc aagatcctcg cctgcgtgaa    420
gagtgtccga aaacctcggg tgtcaacaag ctggcatggg ggcgcaccgc gggagagaac    480
caggtgtggc tcggcggcca ccaccatgac ctcgacccgc accccctcga ctccgctgag    540
gctgtctgga cctgctggcc aactctcggc tacgggcctt cagggatgtg cacggctcgc    600
gttgtccggg gaagaagcga acgcaacgtc accgcgggc cgctgcgcgg caccgtctcc    660
taccacccgt tggccgcac cctgttcgaa agcctgatcc tcaacattcc taccccggc     720 actggtgcag ccgacctcgc cttctgggaa cagccagagc tcaacgaccc gctcggtctt    780
```

```
cccgaagaat ccgcgggact cgccgggatt ctgaggctcg accacttccg ccatgctgtc    840
ctgctgcacc cctcgccaga tggttcacac gtcgtggatg catgggtgac ctgggcgtgg    900
cgggaacgca acatttcgcc agaactcgac ccttacctca tctaccagac aagcaaggaa    960
ggccgtgtct atccgcggcc agccgaagcg gaacgggcca tatggcggga cctcgacgcc   1020
ttgctgcact acggcgaaga cggcaactac cggccgacaa ttttggacaa ctgcacgcct   1080
ttggcgcagg ttccccaaga agtcctggac tccctgcggc tgcgcgcctt cgggttcgac   1140
caggacggtc aggcccgtga caaacagtgg ttcaccgcca ccaccccggc cgtgctgcgc   1200
tggctagcag accgggaaac cgacgacaac gagaacgccc gaatcgtgcg tcgtatcacc   1260
ctggctcgca aagccgcgga agcactcggc cgccgcctag aaaaagcgtg caaagaagcg   1320
tggaaggaaa gcaacagccc tagctccact agctccggca ccaacgctaa gaccgagacc   1380
ggtgtcggac cctgggtgca gcacggcatg agccgctact gggcgaaagc cgagccggtc   1440
ttctggaaca tcgtctacga ccggcccgct caaggctaca cccccggcat ggcaggcccc   1500
ggaaacgcct tcaacctggt cgcgttagct gcctacgacg aggtgaccgg tcctactgt    1560 gaacggcccc gcgtggccaa agtcgtggag cggcaccgca gcaccctgtt cagcaactgg   1620
acaccgaaac aggacaagga agccgcgtga                                    1650
```

<210> SEQ ID NO 7
<211> LENGTH: 549
<212> TYPE: PRT
<213> ORGANISM: Thermobifida fusca

<400> SEQUENCE: 7

```
Val Leu Ser Val Ala Leu Cys Phe Leu Val Gly Gly Ala Ile Pro Ser
1               5                   10                  15

Pro Pro Ser Phe Asp Val Thr Ile Ala Pro Trp Leu Ile Ala Arg Ser
            20                  25                  30

Arg Asp Val Leu Ala Ala Pro Glu Met Leu Gly Leu Arg Asp Val Leu
        35                  40                  45

Ile Arg Ser His Glu Leu Ser Asp Val Glu Ile Pro Leu Pro Pro Gly
    50                  55                  60

Ala Ala Val Leu Trp Arg Ile Leu Ala Leu Ile Thr Ala Arg Ile Thr
65                  70                  75                  80

Gly Leu Asp Gln Pro Pro Asn Lys Asn Pro Lys Arg Lys Trp Gln Ala
                85                  90                  95

Arg Arg Ser Gln Ile Leu Ser Lys Gly Arg Leu Asp Pro Glu Ala Val
            100                 105                 110

Asp Ala Tyr Phe Ala Asp Tyr Ser Glu Arg Phe Asp Leu Phe His Pro
        115                 120                 125

Glu Arg Pro Trp Leu Gln Asp Pro Arg Leu Arg Glu Glu Cys Pro Lys
    130                 135                 140

Thr Ser Gly Val Asn Lys Leu Ala Trp Gly Arg Thr Ala Gly Glu Asn
145                 150                 155                 160

Gln Val Trp Leu Gly Gly His His Asp Leu Asp Pro His Pro Leu
                165                 170                 175

Asp Ser Ala Glu Ala Val Trp His Leu Leu Ala Thr Leu Gly Tyr Gly
            180                 185                 190

Pro Ser Gly Met Cys Thr Ala Arg Val Val Arg Gly Arg Ser Glu Arg
        195                 200                 205

Asn Val Thr Ala Gly Pro Leu Arg Gly Thr Val Ser Tyr His Pro Leu
    210                 215                 220
```

```
Gly Arg Thr Leu Phe Glu Ser Leu Ile Leu Asn Ile Pro Tyr Pro Gly
225                 230                 235                 240

Thr Gly Ala Ala Asp Leu Ala Phe Trp Glu Gln Pro Glu Leu Asn Asp
                245                 250                 255

Pro Leu Gly Leu Pro Glu Glu Ser Ala Gly Leu Ala Gly Ile Leu Arg
                260                 265                 270

Leu Asp His Phe Arg His Ala Val Leu Leu His Pro Ser Pro Asp Gly
            275                 280                 285

Ser His Val Val Asp Ala Trp Val Thr Trp Ala Trp Arg Glu Arg Asn
        290                 295                 300

Ile Ser Pro Glu Leu Asp Pro Tyr Leu Ile Tyr Gln Thr Ser Lys Glu
305                 310                 315                 320

Gly Arg Val Tyr Pro Arg Pro Ala Glu Ala Glu Arg Ala Ile Trp Arg
                325                 330                 335

Asp Leu Asp Ala Leu Leu His Tyr Gly Glu Asp Gly Asn Tyr Arg Pro
                340                 345                 350

Thr Ile Leu Asp Asn Cys Thr Pro Leu Ala Gln Val Pro Gln Glu Val
            355                 360                 365

Leu Asp Ser Leu Arg Leu Arg Ala Phe Gly Phe Asp Gln Asp Gly Gln
370                 375                 380

Ala Arg Asp Lys Gln Trp Phe Thr Ala Thr Thr Pro Ala Val Leu Arg
385                 390                 395                 400

Trp Leu Ala Asp Arg Glu Thr Asp Asp Asn Glu Asn Ala Arg Ile Val
                405                 410                 415

Arg Arg Ile Thr Leu Ala Arg Lys Ala Glu Ala Leu Gly Arg Arg
            420                 425                 430

Leu Glu Lys Ala Cys Lys Glu Ala Trp Lys Glu Ser Asn Ser Pro Ser
            435                 440                 445

Ser Thr Ser Ser Gly Thr Asn Ala Lys Thr Thr Gly Val Gly Pro
            450                 455                 460

Trp Val Gln His Gly Met Ser Arg Tyr Trp Ala Lys Ala Glu Pro Val
465                 470                 475                 480

Phe Trp Asn Ile Val Tyr Asp Arg Pro Ala Gln Gly Tyr Thr Pro Gly
                485                 490                 495

Met Ala Gly Pro Gly Asn Ala Phe Asn Leu Val Ala Leu Ala Ala Tyr
                500                 505                 510

Asp Glu Val Thr Gly Pro Tyr Cys Glu Arg Pro Arg Val Ala Lys Val
            515                 520                 525

Val Glu Arg His Arg Ser Thr Leu Phe Ser Asn Trp Thr Pro Lys Gln
        530                 535                 540

Asp Lys Glu Ala Ala
545

<210> SEQ ID NO 8
<211> LENGTH: 150
<212> TYPE: PRT
<213> ORGANISM: Artificial Sequence
<220> FEATURE:
<223> OTHER INFORMATION: N-terminal 6xHis-TwinStrep Sumo Tag

<400> SEQUENCE: 8

Met His His His His His Ser Ser Gly Leu Val Pro Arg Gly Ser
1               5                   10                  15

His Met Ala Ser Trp Ser His Pro Gln Phe Glu Lys Gly Gly Gly Ser
            20                  25                  30
```

Gly Gly Gly Ser Gly Gly Ser Ala Trp Ser His Pro Gln Phe Glu Lys
            35                  40                  45

Met Ser Asp Ser Glu Val Asn Gln Glu Ala Lys Pro Glu Val Lys Pro
 50                  55                  60

Glu Val Lys Pro Glu Thr His Ile Asn Leu Lys Val Ser Asp Gly Ser
 65                  70                  75                  80

Ser Glu Ile Phe Phe Lys Ile Lys Lys Thr Thr Pro Leu Arg Arg Leu
                85                  90                  95

Met Glu Ala Phe Ala Lys Arg Gln Gly Lys Glu Met Asp Ser Leu Arg
            100                 105                 110

Phe Leu Tyr Asp Gly Ile Arg Ile Gln Ala Asp Gln Thr Pro Glu Asp
            115                 120                 125

Leu Asp Met Glu Asp Asn Asp Ile Ile Glu Ala His Arg Glu Gln Ile
130                 135                 140

Gly Gly Ser Leu Ser Val
145                 150

<210> SEQ ID NO 9
<211> LENGTH: 735
<212> TYPE: DNA
<213> ORGANISM: Thermobifida fusca

<400> SEQUENCE: 9
gtgaacagcg actacatact ccagcacgct gatgccctcg tgaaacgggt gagcaagctc      60
attgtcaacg aaccagcggc acgggccgca ctgcggcgcg gtgtgggact ggcccccgag     120
gatccgcgca tgctggccgc tcaccgcgtg gtcgcccctt acgttccgt  ccccaccgac     180 tacgacgtcg accgtcgccg ggccgcgtcc ctatgggacg tccacgctgt ggagcgcgcc     240
ttctacgcag tcgcagcaat catggccgca cagcccagaa cgcccgcga  ccaggaagcg     300 gaagctaccg aagaacaaac cggagaacca caggacagca aggcactcac tgagccaacc     360
cctgccgaag aaagcagcgc caccaaggat ggaaagccgg accggcggcc aacctggga     420 gtatccctcg ctcaagccgt cttcgacaaa gggctcaacg ctgacagcac cgagcagcgc     480
ctgcacctga tcgccgcca  gaacctcgac ggcgtccacc gccacctgcc gcgcctggtc     540 ctataccctgc gcagcgacca agtccacatc gactgggga  tcctcatccg agacctggcc     600
cgctggggcc acacccccg  ccacgtcgcc cgcgaatggg tccaggacta ccaccgcacc     660
ctcgaaaccc tgacccgtca agcagagcag aaaaacaaga caacaccac  cgatgaggag     720 gccgaagcag catga                                                     735

<210> SEQ ID NO 10
<211> LENGTH: 190
<212> TYPE: PRT
<213> ORGANISM: Artificial Sequence
<220> FEATURE:
<223> OTHER INFORMATION: Sum Total of all Engineering

<400> SEQUENCE: 10

Met Val Asn Ser Asp Tyr Ile Leu Gln His Ala Asp Ala Leu Val Lys
 1               5                   10                  15

Arg Val Ser Lys Leu Ile Val Ala Glu Pro Ala Ala Arg Ala Ala Leu
                20                  25                  30

Arg Arg Gly Val Gly Leu Ala Pro Glu Asp Pro Arg Met Leu Ala Ala
            35                  40                  45

```
His Arg Val Ala Pro Tyr Val Pro Val Pro Thr Asp Tyr Asp Val
    50                  55                  60

Asp Arg Arg Arg Ala Ala Ser Leu Trp Asp Val His Ala Val Glu Arg
65                  70                  75                  80

Ala Phe Tyr Ala Val Ala Ile Met Ala Ala Gln Pro Arg Ser Ala
                85                  90                  95

Arg Asp Asp Arg Met His Gln Arg Pro Asn Leu Gly Val Ser Leu
            100                 105                 110

Ala Gln Ala Val Pro Asp Lys Gly Leu Asn Ala Asp Ser Thr Glu Gln
        115                 120                 125

Arg Leu His Leu Ile Ala Arg Gln Asn Leu Asp Gly Val His Arg His
    130                 135                 140

Leu Pro Arg Leu Val Leu Tyr Leu Arg Ser Asp Gln Val His Ile Asp
145                 150                 155                 160

Trp Gly Ile Leu Ile Arg Asp Leu Ala Arg Trp Gly His Thr Pro Arg
                165                 170                 175

His Val Ala Arg Glu Trp Val Gln Asp Tyr His Arg Thr Leu
            180                 185                 190
```

```
<210> SEQ ID NO 11
<211> LENGTH: 1122
<212> TYPE: DNA
<213> ORGANISM: Thermobifida fusca

<400> SEQUENCE: 11
atgactttcg ttgacattca cgccatccag accctgccct actccaacat caaccgcgac      60
gacttgggct cccccaagac ggtcgtctac ggcggcaagg aacgcactcg cgtgtccagc     120
cagagctgga agcgcgccgt ccgccacgaa gtggaagccc ggctcggcga caaggcggtc     180
cgcacccgcc gtatcatcag cgagatcgcc aagcggcttc gggaacgcgg ctgggacgct     240
gacctcgctg acgccggagc acgccaagtc gtgctgtctg tcggtaagaa gagcggcatc     300
aaactggaaa aggagaaaga cagcgaggcc cctgccactt ctgtcctgtt ctacctcccg     360
gtccccgcaa tcgacgaact cgccgccatc gccgatgagc accgggacgc cgtcgccaaa     420
gaagcagcca agaagacccc caagggaatc ctccccgctg accgcatcac cgaagtactg     480
aagagccgca acgtctcagt caacttgttc ggtcggatgc tcgctgaact gccctccacc     540
gaggtcgacg gcgcagtgca gttcgcgcac gcgttcaccg tgcacggcac caccgtagaa     600
gtcgacttct tcaccgctgt cgacgacatc cccaaagaaa acgaccacgg tagtggccac     660
atgaacgcgg gccagttcag tgccggaacg ttctaccgct acgccaacgt caacctcgac     720
cgactggtgg aaaacaccgg tgacgcccaa accgccgcca ccgccgtggc cgagttcctc     780
cgcgctttcc tgagcacggt ccctccggg aaacagaacg ctaccgctgc catgaccctg     840
cccgacctgg tacacatcgc ggtacgcttc gaccgaccca tctctttcgc tcccgcgttc     900
gaaaccgcgc tatacggcag cgacggctac accctccgcg cctgccagga actcaacaac     960
tacgccgaac ggctccgcga agtctggccc gacgacgcga tccgcggcta cgcgaccgtg    1020
gaaaacaaga ccgacctcgc cgcgttgggg gagcggtacg actcctaccc ggcgctcatc    1080
gacgccatgg tcgcggcagc cttcgagggg gagcgggagt ga                        1122
```

```
<210> SEQ ID NO 12
<211> LENGTH: 373
<212> TYPE: PRT
<213> ORGANISM: Thermobifida fusca
```

<400> SEQUENCE: 12

```
Met Thr Phe Val Asp Ile His Ala Ile Gln Thr Leu Pro Tyr Ser Asn
1               5                   10                  15

Ile Asn Arg Asp Asp Leu Gly Ser Pro Lys Thr Val Tyr Gly Gly
            20                  25                  30

Lys Glu Arg Thr Arg Val Ser Ser Gln Ser Trp Lys Arg Ala Val Arg
            35                  40                  45

His Glu Val Glu Ala Arg Leu Gly Asp Lys Ala Val Arg Thr Arg Arg
        50                  55                  60

Ile Ile Ser Glu Ile Ala Lys Arg Leu Arg Glu Arg Gly Trp Asp Ala
65                  70                  75                  80

Asp Leu Ala Asp Ala Gly Ala Arg Gln Val Val Leu Ser Val Gly Lys
                85                  90                  95

Lys Ser Gly Ile Lys Leu Glu Lys Glu Lys Asp Ser Glu Ala Pro Ala
            100                 105                 110

Thr Ser Val Leu Phe Tyr Leu Pro Val Pro Ala Ile Asp Glu Leu Ala
            115                 120                 125

Ala Ile Ala Asp Glu His Arg Asp Ala Val Ala Lys Glu Ala Ala Lys
130                 135                 140

Lys Thr Pro Lys Gly Ile Leu Pro Ala Asp Arg Ile Thr Glu Val Leu
145                 150                 155                 160

Lys Ser Arg Asn Val Ser Val Asn Leu Phe Gly Arg Met Leu Ala Glu
                165                 170                 175

Leu Pro Ser Thr Glu Val Asp Gly Ala Val Gln Phe Ala His Ala Phe
            180                 185                 190

Thr Val His Gly Thr Thr Val Glu Val Asp Phe Phe Thr Ala Val Asp
            195                 200                 205

Asp Ile Pro Lys Glu Asn Asp His Gly Ser Gly His Met Asn Ala Gly
210                 215                 220

Gln Phe Ser Ala Gly Thr Phe Tyr Arg Tyr Ala Asn Val Asn Leu Asp
225                 230                 235                 240

Arg Leu Val Glu Asn Thr Gly Asp Ala Gln Thr Ala Arg Thr Ala Val
                245                 250                 255

Ala Glu Phe Leu Arg Ala Phe Leu Ser Thr Val Pro Ser Gly Lys Gln
            260                 265                 270

Asn Ala Thr Ala Ala Met Thr Leu Pro Asp Leu Val His Ile Ala Val
            275                 280                 285

Arg Phe Asp Arg Pro Ile Ser Phe Ala Pro Ala Phe Glu Thr Ala Leu
290                 295                 300

Tyr Gly Ser Asp Gly Tyr Thr Leu Arg Ala Cys Gln Glu Leu Asn Asn
305                 310                 315                 320

Tyr Ala Glu Arg Leu Arg Glu Val Trp Pro Asp Asp Ala Ile Arg Gly
                325                 330                 335

Tyr Ala Thr Val Glu Asn Lys Thr Asp Leu Ala Ala Leu Gly Glu Arg
            340                 345                 350

Tyr Asp Ser Tyr Pro Ala Leu Ile Asp Ala Met Val Ala Ala Ala Phe
            355                 360                 365

Glu Gly Glu Arg Glu
        370
```

<210> SEQ ID NO 13
<211> LENGTH: 27
<212> TYPE: PRT

<213> ORGANISM: Artificial Sequence
<220> FEATURE:
<223> OTHER INFORMATION: C-terminal NLS Tag

<400> SEQUENCE: 13

Ala Met Val Ala Ala Phe Gly Ser Gly Ser Gly Gly Lys Leu Pro
1               5                   10                  15

Lys Lys Lys Arg Lys Val Glu Gly Glu Arg Glu
            20                  25

<210> SEQ ID NO 14
<211> LENGTH: 765
<212> TYPE: DNA
<213> ORGANISM: Thermobifida fusca

<400> SEQUENCE: 14
gtgagtggct tcctgctgcg gctagctggc cccatgcaaa gctggggcga acacagcatg    60
ttcggggaac gcgacaccct gccttacccg agccgctccg gtctgatcgg aatgttcgct   120
gccgcccagg gggtgcgccg cggcgaccct ctggaccgct acaaggaact gaagttcacc   180
gttcgcgtcg accggccagg ggtgcggctc gtcgacttcc acacgatcgg cggcggcctt   240
cccaaagagc gcaccgtgcc caccgctgca ggtgaacggc gcgaccctaa gaaagccacc   300
atcgtcacca gccgttccta cctggccgac gccgtgttca ccgtcgctgt caccggaccg   360
gaagcagaca ctatcgccga cgcgttagcc gccccctact ggcagcccta cctggggcgg   420
cgcgcgttcg ttcctgaccc gctactggtc ctgcgccgca gggtcgctga cccggtgcga   480
gaactagtgg aagcggtgcc gctcccccat cgcagggtgg aagaagacgc tgcaactgtg   540
cttgtggact tgatctatga agagggcgaa tacccagata cgcgcactct gacggtgctc   600
aacgacgttc cgctctcgtt cgacagcaag agccgccgct actccacccg acagatccga   660
gtagttccca ccgaggttcc cgcgacactc gtggccggtc ccggcaggga ctaccagaac   720
aagctttttca catacgtcaa gcagtgcgcc gaggaggcag catga                  765

<210> SEQ ID NO 15
<211> LENGTH: 254
<212> TYPE: PRT
<213> ORGANISM: Thermobifida fusca

<400> SEQUENCE: 15

Val Ser Gly Phe Leu Leu Arg Leu Ala Gly Pro Met Gln Ser Trp Gly
1               5                   10                  15

Glu His Ser Met Phe Gly Glu Arg Asp Thr Leu Pro Tyr Pro Ser Arg
            20                  25                  30

Ser Gly Leu Ile Gly Met Phe Ala Ala Ala Gln Gly Val Arg Arg Gly
        35                  40                  45

Asp Pro Leu Asp Arg Tyr Lys Glu Leu Lys Phe Thr Val Arg Val Asp
    50                  55                  60

Arg Pro Gly Val Arg Leu Val Asp Phe His Thr Ile Gly Gly Gly Leu
65                  70                  75                  80

Pro Lys Glu Arg Thr Val Pro Thr Ala Ala Gly Glu Arg Arg Asp Pro
                85                  90                  95

Lys Lys Ala Thr Ile Val Thr Ser Arg Ser Tyr Leu Ala Asp Ala Val
            100                 105                 110

Phe Thr Val Ala Val Thr Gly Pro Glu Ala Asp Thr Ile Ala Asp Ala
        115                 120                 125

Leu Ala Ala Pro Tyr Trp Gln Pro Tyr Leu Gly Arg Arg Ala Phe Val
            130                 135                 140

Pro Asp Pro Leu Leu Val Leu Arg Arg Arg Val Ala Asp Pro Val Arg
145                 150                 155                 160

Glu Leu Val Glu Ala Val Pro Leu Pro His Arg Arg Val Glu Glu Asp
                165                 170                 175

Ala Ala Thr Val Leu Val Asp Leu Ile Tyr Glu Glu Gly Glu Tyr Pro
            180                 185                 190

Asp Thr Arg Thr Leu Thr Val Leu Asn Asp Val Pro Leu Ser Phe Asp
                195                 200                 205

Ser Lys Ser Arg Arg Tyr Ser Thr Arg Gln Ile Arg Val Val Pro Thr
            210                 215                 220

Glu Val Pro Ala Thr Leu Val Ala Gly Pro Gly Arg Asp Tyr Gln Asn
225                 230                 235                 240

Lys Leu Phe Thr Tyr Val Lys Gln Cys Ala Glu Glu Ala Ala
                245                 250

<210> SEQ ID NO 16
<211> LENGTH: 699
<212> TYPE: DNA
<213> ORGANISM: Thermobifida fusca

<400> SEQUENCE: 16

```
atgacgtggc taaccaagat cgttcctgac ctgcgctacc gccagaccog agcagacttc    60
cgtaccgctg gaaatctaca tcgtaaactc atccggcttt cttctgacct cggtgaggag   120
cggatcgcta accccgtca gcaatccggc ttactgttcc gcatcgaaga aaccagaaac    180
gagctctacc tgctggtaca gagtcactcc cccctgcggg ttgacggct tggcccogga    240
taccacgggg tccagatgcg taacctcgac ccttcctgg ctcggctaga caaaggcagc    300
cgtgtccgct accggattgt ggccagtccc accaaacgac tcggccggtc cgagaacaac    360
acccaacgcc ttggcctgaa agagccgccg aaaaaaccaa gagagtacac ctgggctctg    420
cgcggggccg cagccgagga gtggtggcat tcccgtgcgg cagccaacgg actggaactc    480
ctcagcacct acgcgcagac actcgatgac gtccgcgacc tgggaccgc tgaccgtagc    540
cgcaaaatcc gccacccagc cgtgcgcttc gacggtgaag ccgtcatctc tgacgtcgac    600
gccgtgcgtc atgcggtact taacggcatc ggccgcggca aatcctacgg ctgcgggctg    660
ctcagcctcg ccctaatcga ggaaggagaa catggataa                           699
```

<210> SEQ ID NO 17
<211> LENGTH: 232
<212> TYPE: PRT
<213> ORGANISM: Thermobifida fusca

<400> SEQUENCE: 17

Met Thr Trp Leu Thr Lys Ile Val Pro Asp Leu Arg Tyr Arg Gln Thr
1                5                  10                  15

Arg Ala Asp Phe Arg Thr Ala Gly Asn Leu His Arg Lys Leu Ile Arg
            20                  25                  30

Leu Ser Asp Leu Gly Glu Glu Arg Ile Ala Asn Pro Arg Gln Gln
        35                  40                  45

Ser Gly Leu Leu Phe Arg Ile Glu Glu Thr Arg Asn Glu Leu Tyr Leu
    50                  55                  60

Leu Val Gln Ser His Ser Pro Leu Arg Val Asp Arg Leu Gly Pro Gly
65                  70                  75                  80

Tyr His Gly Val Gln Met Arg Asn Leu Asp Pro Phe Leu Ala Arg Leu
                85                  90                  95

Asp Lys Gly Ser Arg Val Arg Tyr Arg Ile Val Ala Ser Pro Thr Lys
            100                 105                 110

Arg Leu Gly Arg Ser Glu Asn Asn Thr Gln Arg Leu Gly Leu Lys Glu
        115                 120                 125

Pro Pro Lys Lys Pro Arg Glu Tyr Thr Trp Ala Leu Arg Gly Ala Ala
130                 135                 140

Ala Glu Glu Trp Trp His Ser Arg Ala Ala Asn Gly Leu Glu Leu
145                 150                 155                 160

Leu Ser Thr Tyr Ala Gln Thr Leu Asp Asp Val Arg Asp Pro Gly Thr
                165                 170                 175

Ala Asp Arg Ser Arg Lys Ile Arg His Pro Ala Val Arg Phe Asp Gly
            180                 185                 190

Glu Ala Val Ile Ser Asp Val Asp Ala Val Arg His Ala Val Leu Asn
        195                 200                 205

Gly Ile Gly Arg Gly Lys Ser Tyr Gly Cys Gly Leu Leu Ser Leu Ala
210                 215                 220

Leu Ile Glu Glu Gly Glu His Gly
225                 230

<210> SEQ ID NO 18
<211> LENGTH: 90
<212> TYPE: DNA
<213> ORGANISM: Artificial Sequence
<220> FEATURE:
<223> OTHER INFORMATION: crRNA Generic (single unit unprocessed - Repeat-Spacer-Repeat)
<220> FEATURE:
<221> NAME/KEY: misc_feature
<222> LOCATION: (30)..(61)
<223> OTHER INFORMATION: n is a, c, g, or t

<400> SEQUENCE: 18
gtgagcccca cgcacgtggg gatggaccgn nnnnnnnnn nnnnnnnnn nnnnnnnnn      60 ngtgagcccc acgcacgtgg ggatggaccg                                   90

<210> SEQ ID NO 19
<211> LENGTH: 60
<212> TYPE: DNA
<213> ORGANISM: Artificial Sequence
<220> FEATURE:
<223> OTHER INFORMATION: crRNA Generic (processed)
<220> FEATURE:
<221> NAME/KEY: misc_feature
<222> LOCATION: (9)..(40)
<223> OTHER INFORMATION: n is a, c, g, or t

<400> SEQUENCE: 19
atggaccgnn nnnnnnnn nnnnnnnnn nnnnnnnnn gtgagcccca cgcacgtggg      60

<210> SEQ ID NO 20
<211> LENGTH: 32
<212> TYPE: DNA
<213> ORGANISM: Artificial Sequence
<220> FEATURE:
<223> OTHER INFORMATION: Spacer: GFP crRNA-A

<400> SEQUENCE: 20
gtggcatcgc cctcgccctc gccggacacg ct                                32

```
<210> SEQ ID NO 21
<211> LENGTH: 161
<212> TYPE: DNA
<213> ORGANISM: Artificial Sequence
<220> FEATURE:
<223> OTHER INFORMATION: Expression Cassette

<400> SEQUENCE: 21
ggatccgagc cccacgcacg tggggatgga ccggtggcat cgccctcgcc ctcgccggac      60
acgctgtgag ccccacgcac gtggggatgg accggtggca tcgccctcgc cctcgccgga     120
cacgctgtga gccccacgca cgtggggatg gtgacgaatt c                         161

<210> SEQ ID NO 22
<211> LENGTH: 32
<212> TYPE: DNA
<213> ORGANISM: Artificial Sequence
<220> FEATURE:
<223> OTHER INFORMATION: GFP-crRNA-B

<400> SEQUENCE: 22
gctacgtcca ggagcgcacc atcttcttca ag                                    32

<210> SEQ ID NO 23
<211> LENGTH: 161
<212> TYPE: DNA
<213> ORGANISM: Artificial Sequence
<220> FEATURE:
<223> OTHER INFORMATION: Expression Cassette

<400> SEQUENCE: 23
gaattcgagc cccacgcacg tggggatgga ccggctacgt ccaggagcgc accatcttct      60
tcaaggtgag ccccacgcac gtggggatgg accggctacg tccaggagcg caccatcttc     120
ttcaaggtga gccccacgca cgtggggatg gtgacaagct t                         161

<210> SEQ ID NO 24
<211> LENGTH: 32
<212> TYPE: DNA
<213> ORGANISM: Artificial Sequence
<220> FEATURE:
<223> OTHER INFORMATION: GFP-crRNA-C

<400> SEQUENCE: 24
tcgatgccct tcagctcgat gcggttcacc ag                                    32

<210> SEQ ID NO 25
<211> LENGTH: 163
<212> TYPE: DNA
<213> ORGANISM: Artificial Sequence
<220> FEATURE:
<223> OTHER INFORMATION: Expression Cassette

<400> SEQUENCE: 25
aagcttgagc cccacgcacg tggggatgga ccgtcgatgc ccttcagctc gatgcggttc      60
accaggtgag ccccacgcac gtggggatgg accgtcgatg cccttcagct cgatgcggtt     120
caccaggtga gccccacgca cgtggggatg gtgacgcggc cgc                       163

<210> SEQ ID NO 26
<211> LENGTH: 32
<212> TYPE: DNA
<213> ORGANISM: Artificial Sequence
<220> FEATURE:
<223> OTHER INFORMATION: GFP crRNA-D
```

```
<400> SEQUENCE: 26
cgcgatcaca tggtcctgct ggagttcgtg ac                                  32

<210> SEQ ID NO 27
<211> LENGTH: 163
<212> TYPE: DNA
<213> ORGANISM: Artificial Sequence
<220> FEATURE:
<223> OTHER INFORMATION: Expression Cassette

<400> SEQUENCE: 27
gcggccgcga gccccacgca cgtggggatg gaccgcgcga tcacatggtc ctgctggagt    60
tcgtgacgtg agccccacgc acgtggggat ggaccgcgcg atcacatggt cctgctggag   120
ttcgtgacgt gagccccacg cacgtgggga tggtgacctc gag                    163

<210> SEQ ID NO 28
<211> LENGTH: 32
<212> TYPE: DNA
<213> ORGANISM: Artificial Sequence
<220> FEATURE:
<223> OTHER INFORMATION: tdTomato crRNA-A

<400> SEQUENCE: 28
ctggacatca cctcccacaa cgaggactac ac                                  32

<210> SEQ ID NO 29
<211> LENGTH: 104
<212> TYPE: DNA
<213> ORGANISM: Artificial Sequence
<220> FEATURE:
<223> OTHER INFORMATION: Expression Cassette

<400> SEQUENCE: 29
ggatccgagc cccacgcacg tgggatgga ccgctggaca tcacctccca caacgaggac     60
tacacgtgag ccccacgcac gtggggatgg accgttttga attc                   104

<210> SEQ ID NO 30
<211> LENGTH: 51
<212> TYPE: DNA
<213> ORGANISM: Artificial Sequence
<220> FEATURE:
<223> OTHER INFORMATION: Oligonucleotide

<400> SEQUENCE: 30
ggcaagcttc ccaagaagaa gaggaaggtg gaggggagc gggagtgagt g             51

<210> SEQ ID NO 31
<211> LENGTH: 35
<212> TYPE: DNA
<213> ORGANISM: Artificial Sequence
<220> FEATURE:
<223> OTHER INFORMATION: Oligonucleotides

<400> SEQUENCE: 31
acctgaaccg ctaccgaagg ctgccgcgac catgg                              35

<210> SEQ ID NO 32
<211> LENGTH: 44
<212> TYPE: DNA
<213> ORGANISM: Artificial Sequence
<220> FEATURE:
<223> OTHER INFORMATION: Oligonucleotide
```

<400> SEQUENCE: 32
tttaagaagg agatatacat atgagtggct tcctgctgcg gcta                44

<210> SEQ ID NO 33
<211> LENGTH: 39
<212> TYPE: DNA
<213> ORGANISM: Artificial Sequence
<220> FEATURE:
<223> OTHER INFORMATION: Oligonucleotide

<400> SEQUENCE: 33
attaaagtta aacaaaatta ttcccgctcc ccctccacc                      39

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide

<400> SEQUENCE: 34
tcatcgaatt tttgcagcag                                           20

<210> SEQ ID NO 35
<211> LENGTH: 38
<212> TYPE: DNA
<213> ORGANISM: Artificial Sequence
<220> FEATURE:
<223> OTHER INFORMATION: Oligonucleotide

<400> SEQUENCE: 35
accatggcct atagtgagtc gtattaattt cctaatgc                       38

<210> SEQ ID NO 36
<211> LENGTH: 86
<212> TYPE: DNA
<213> ORGANISM: Artificial Sequence
<220> FEATURE:
<223> OTHER INFORMATION: Oligonucleotide

<400> SEQUENCE: 36
aattcgagcc ccacgcacgt ggggatggac cgaccttgca ctacctgtgg cttccatttt    60
cctggtgagc cccacgcacg tgggga                                        86

<210> SEQ ID NO 37
<211> LENGTH: 86
<212> TYPE: DNA
<213> ORGANISM: Artificial Sequence
<220> FEATURE:
<223> OTHER INFORMATION: Oligonucleotide

<400> SEQUENCE: 37
agcttcccca cgtgcgtggg gctcaccagg aaaatggaag ccacaggtag tgcaaggtcg    60
gtccatcccc acgtgcgtgg ggctcg                                        86

<210> SEQ ID NO 38
<211> LENGTH: 86
<212> TYPE: DNA
<213> ORGANISM: Artificial Sequence
<220> FEATURE:
<223> OTHER INFORMATION: Oligonucleotide

<400> SEQUENCE: 38
aattcgagcc ccacgcacgt ggggatggac cgaagccgag gctcccccag cgaagcccct      60
ttccgtgagc cccacgcacg tgggga                                           86

<210> SEQ ID NO 39
<211> LENGTH: 86
<212> TYPE: DNA
<213> ORGANISM: Artificial Sequence
<220> FEATURE:
<223> OTHER INFORMATION: Oligonucleotide

<400> SEQUENCE: 39
agcttcccca cgtgcgtggg gctcacggaa aggggcttcg ctggggagc ctcggcttcg       60 gtccatcccc acgtgcgtgg ggctcg                                           86

<210> SEQ ID NO 40
<211> LENGTH: 86
<212> TYPE: DNA
<213> ORGANISM: Artificial Sequence
<220> FEATURE:
<223> OTHER INFORMATION: Oligonucleotide

<400> SEQUENCE: 40
aattcgagcc ccacgcacgt ggggatggac cgcagccgag gctcccccag cgaagcccct      60
ttccgtgagc cccacgcacg tgggga                                           86

<210> SEQ ID NO 41
<211> LENGTH: 86
<212> TYPE: DNA
<213> ORGANISM: Artificial Sequence
<220> FEATURE:
<223> OTHER INFORMATION: Oligonucleotide

<400> SEQUENCE: 41
agcttcccca cgtgcgtggg gctcacggaa aggggcttcg ctggggagc ctcggctgcg       60 gtccatcccc acgtgcgtgg ggctcg                                           86

<210> SEQ ID NO 42
<211> LENGTH: 483
<212> TYPE: DNA
<213> ORGANISM: Artificial Sequence
<220> FEATURE:
<223> OTHER INFORMATION: Oligonucleotide

<400> SEQUENCE: 42
cacgtgctcg cgacccggtt cggtgccggt tcagtccggg tgttgtgcta ctacgtggac      60
acggcgggga accgctggct tgaccctgaa tgcacggtcg agtttcctga acagggcacg     120
gggcgagagg gccggttcac catggcagac tgccgcgacc tggtggcccg cacgatcccg     180
gtgcgtatgg gtccctgggc gagtcaactc accgaggaca accatcctcc tgaggcatgg     240
cgggagtcgt tctaccttcg cgacctggtt cttatacctc aacgtgtgac agacgagggc     300
gcggtgctcc ccactgaaac cggtggacga gagtggttgc ttgatccctg taaggggctg     360
atctttggat ccgttggtta cccatacgat gttcctgact atgcgggcta tccctatgac     420
gtcccggact atgcaggatc ctatccagaa ttccccaaga agaagaggaa ggtgtaactc     480
gag                                                                   483

<210> SEQ ID NO 43

<211> LENGTH: 161
<212> TYPE: DNA
<213> ORGANISM: Artificial Sequence
<220> FEATURE:
<223> OTHER INFORMATION: Oligonucleotide

<400> SEQUENCE: 43
gaattcgagc cccacgcacg tggggatgga ccggctacgt ccaggagcgc accatcttct    60
tcaaggtgag ccccacgcac gtggggatgg accggctacg tccaggagcg caccatcttc   120
ttcaaggtga gccccacgca cgtggggatg gtgacaagct t                       161

<210> SEQ ID NO 44
<211> LENGTH: 163
<212> TYPE: DNA
<213> ORGANISM: Artificial Sequence
<220> FEATURE:
<223> OTHER INFORMATION: Oligonucleotide

<400> SEQUENCE: 44
aagcttgagc cccacgcacg tggggatgga ccgtcgatgc ccttcagctc gatgcggttc    60
accaggtgag ccccacgcac gtggggatgg accgtcgatg cccttcagct cgatgcggtt   120
caccaggtga gccccacgca cgtggggatg gtgacgcggc cgc                     163

<210> SEQ ID NO 45
<211> LENGTH: 410
<212> TYPE: DNA
<213> ORGANISM: Artificial Sequence
<220> FEATURE:
<223> OTHER INFORMATION: Oligonucleotide

<400> SEQUENCE: 45
gaattctaat acgactcact atagggagcc ccacgcacgt ggggatggac cgccagtgat    60
aagtggaatg ccatgtgggc tgtcgtgagc cccacgcacg tggggatgga ccgccagtga   120
taagtggaat gccatgtggg ctgtcgtgag ccccacgcac gtggggatgg accgccagtg   180
ataagtggaa tgccatgtgg gctgtcgtga gccccacgca cgtggggatg gaccgccagt   240
gataagtgga atgccatgtg gctgtcgtg agccccacgc acgtgggat ggaccgccag    300 tgataagtgg aatgccatgt gggctgtcgt gagccccacg cacgtgggga tggaccgcta   360 gcataaccccc ttggggcctc taaacgggtc ttgaggggtt ttttggatcc              410

<210> SEQ ID NO 46
<211> LENGTH: 144
<212> TYPE: DNA
<213> ORGANISM: Artificial Sequence
<220> FEATURE:
<223> OTHER INFORMATION: Oligonucleotide

<400> SEQUENCE: 46
atatcatagt acaataggat ccgagcccca cgcacgtggg gatggaccgc tggacatcac    60
ctcccacaac gaggactaca cgtgagcccc acgcacgtgg ggatggaccg gaattcagtc   120
gtagtttcgc gcatcatggc cata                                          144

<210> SEQ ID NO 47
<211> LENGTH: 20
<212> TYPE: DNA
<213> ORGANISM: Artificial Sequence
<220> FEATURE:
<223> OTHER INFORMATION: Oligonucleotide

```
<400> SEQUENCE: 47
gatggggtgg gggttaaagg                                              20

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide

<400> SEQUENCE: 48
agtactgcac tctttgcccc                                              20

<210> SEQ ID NO 49
<211> LENGTH: 19
<212> TYPE: DNA
<213> ORGANISM: Artificial Sequence
<220> FEATURE:
<223> OTHER INFORMATION: Oligonucleotide

<400> SEQUENCE: 49
aagggagaca ccaggcatc                                               19

<210> SEQ ID NO 50
<211> LENGTH: 20
<212> TYPE: DNA
<213> ORGANISM: Artificial Sequence
<220> FEATURE:
<223> OTHER INFORMATION: Oligonucleotide

<400> SEQUENCE: 50
ggccaattac tgggttcagg                                              20

<210> SEQ ID NO 51
<211> LENGTH: 18
<212> TYPE: DNA
<213> ORGANISM: Artificial Sequence
<220> FEATURE:
<223> OTHER INFORMATION: Oligonucleotide

<400> SEQUENCE: 51
acgaactcca gcaggacc                                                18

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide

<400> SEQUENCE: 52
tagctcggca accctccata                                              20

<210> SEQ ID NO 53
<211> LENGTH: 20
<212> TYPE: DNA
<213> ORGANISM: Artificial Sequence
<220> FEATURE:
<223> OTHER INFORMATION: Oligonucleotide

<400> SEQUENCE: 53
actctatgcc aggcccacta                                              20
```

```
<210> SEQ ID NO 54
<211> LENGTH: 20
<212> TYPE: DNA
<213> ORGANISM: Artificial Sequence
<220> FEATURE:
<223> OTHER INFORMATION: Oligonucleotide

<400> SEQUENCE: 54
tcctttggat gtgctgtccc                                               20

<210> SEQ ID NO 55
<211> LENGTH: 20
<212> TYPE: DNA
<213> ORGANISM: Artificial Sequence
<220> FEATURE:
<223> OTHER INFORMATION: Oligonucleotide

<400> SEQUENCE: 55
aatggcactg gaggaagagc                                               20

<210> SEQ ID NO 56
<211> LENGTH: 20
<212> TYPE: DNA
<213> ORGANISM: Artificial Sequence
<220> FEATURE:
<223> OTHER INFORMATION: Oligonucleotide

<400> SEQUENCE: 56
tgatgccttt gtagggcgtt                                               20

<210> SEQ ID NO 57
<211> LENGTH: 20
<212> TYPE: DNA
<213> ORGANISM: Artificial Sequence
<220> FEATURE:
<223> OTHER INFORMATION: Oligonucleotide

<400> SEQUENCE: 57
tccacgatta gggagttggc                                               20

<210> SEQ ID NO 58
<211> LENGTH: 20
<212> TYPE: DNA
<213> ORGANISM: Artificial Sequence
<220> FEATURE:
<223> OTHER INFORMATION: Oligonucleotide

<400> SEQUENCE: 58
ttgcaaggtg accacacagt                                               20

<210> SEQ ID NO 59
<211> LENGTH: 20
<212> TYPE: DNA
<213> ORGANISM: Artificial Sequence
<220> FEATURE:
<223> OTHER INFORMATION: Oligonucleotide

<400> SEQUENCE: 59
tcgcggtaag tgctaggaac                                               20

<210> SEQ ID NO 60
<211> LENGTH: 20
<212> TYPE: DNA
<213> ORGANISM: Artificial Sequence
<220> FEATURE:
```

<223> OTHER INFORMATION: Oligonucleotide

<400> SEQUENCE: 60
ggtcttgtag ttgccgtcgt                                                    20

<210> SEQ ID NO 61
<211> LENGTH: 19
<212> TYPE: DNA
<213> ORGANISM: Artificial Sequence
<220> FEATURE:
<223> OTHER INFORMATION: Oligonucleotide

<400> SEQUENCE: 61
gatctccggg gtgcggata                                                     19

<210> SEQ ID NO 62
<211> LENGTH: 21
<212> TYPE: DNA
<213> ORGANISM: Artificial Sequence
<220> FEATURE:
<223> OTHER INFORMATION: Oligonucleotide

<400> SEQUENCE: 62
tgtcttcctc ctttgcactt t                                                  21

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide

<400> SEQUENCE: 63
cttgtggccg tttacgtcgc                                                    20

<210> SEQ ID NO 64
<211> LENGTH: 18
<212> TYPE: DNA
<213> ORGANISM: Artificial Sequence
<220> FEATURE:
<223> OTHER INFORMATION: Oligonucleotide

<400> SEQUENCE: 64
gtgagcaagg gcgaggag                                                      18

<210> SEQ ID NO 65
<211> LENGTH: 20
<212> TYPE: DNA
<213> ORGANISM: Artificial Sequence
<220> FEATURE:
<223> OTHER INFORMATION: Oligonucleotide

<400> SEQUENCE: 65
cctaaaccca actccatgcc                                                    20

<210> SEQ ID NO 66
<211> LENGTH: 22
<212> TYPE: DNA
<213> ORGANISM: Artificial Sequence
<220> FEATURE:
<223> OTHER INFORMATION: Oligonucleotide

<400> SEQUENCE: 66
tgtcctctca gatgtgtacc ct                                                 22

-continued

```
<210> SEQ ID NO 67
<211> LENGTH: 20
<212> TYPE: DNA
<213> ORGANISM: Artificial Sequence
<220> FEATURE:
<223> OTHER INFORMATION: Oligonucleotide

<400> SEQUENCE: 67
acaccccaaa gctaaaagcg                                               20

<210> SEQ ID NO 68
<211> LENGTH: 20
<212> TYPE: DNA
<213> ORGANISM: Artificial Sequence
<220> FEATURE:
<223> OTHER INFORMATION: Oligonucleotide

<400> SEQUENCE: 68
ggaggggcct agaagtggta                                               20

<210> SEQ ID NO 69
<211> LENGTH: 21
<212> TYPE: DNA
<213> ORGANISM: Artificial Sequence
<220> FEATURE:
<223> OTHER INFORMATION: Oligonucleotide

<400> SEQUENCE: 69
tcgacaagcc cagaaacttg t                                             21

<210> SEQ ID NO 70
<211> LENGTH: 20
<212> TYPE: DNA
<213> ORGANISM: Artificial Sequence
<220> FEATURE:
<223> OTHER INFORMATION: Oligonucleotide

<400> SEQUENCE: 70
ccgctacccc aatcccaaat                                               20

<210> SEQ ID NO 71
<211> LENGTH: 20
<212> TYPE: DNA
<213> ORGANISM: Artificial Sequence
<220> FEATURE:
<223> OTHER INFORMATION: Oligonucleotide

<400> SEQUENCE: 71
ccccaggcaa tttcccatct                                               20

<210> SEQ ID NO 72
<211> LENGTH: 19
<212> TYPE: DNA
<213> ORGANISM: Artificial Sequence
<220> FEATURE:
<223> OTHER INFORMATION: Oligonucleotide

<400> SEQUENCE: 72
tcctcctcct gagcagtca                                                19

<210> SEQ ID NO 73
<211> LENGTH: 19
<212> TYPE: DNA
<213> ORGANISM: Artificial Sequence
<220> FEATURE:
<223> OTHER INFORMATION: Oligonucleotide
```

<400> SEQUENCE: 73
gtgacgtaaa gccgaaccc					19

<210> SEQ ID NO 74
<211> LENGTH: 37
<212> TYPE: DNA
<213> ORGANISM: Artificial Sequence
<220> FEATURE:
<223> OTHER INFORMATION: Oligonucleotide

<400> SEQUENCE: 74
taatacgact cactatagtt atggcgaccc gcagccc					37

<210> SEQ ID NO 75
<211> LENGTH: 35
<212> TYPE: DNA
<213> ORGANISM: Artificial Sequence
<220> FEATURE:
<223> OTHER INFORMATION: Oligonucleotide

<400> SEQUENCE: 75
ttctagctct aaaacgggct gcgggtcgcc ataac					35

<210> SEQ ID NO 76
<211> LENGTH: 19
<212> TYPE: DNA
<213> ORGANISM: Artificial Sequence
<220> FEATURE:
<223> OTHER INFORMATION: Oligonucleotide

<400> SEQUENCE: 76
ctgtctctta tacacatct					19

<210> SEQ ID NO 77
<211> LENGTH: 33
<212> TYPE: DNA
<213> ORGANISM: Artificial Sequence
<220> FEATURE:
<223> OTHER INFORMATION: Oligonucleotide

<400> SEQUENCE: 77
tcgtcggcag cgtcagatgt gtataagaga cag					33

<210> SEQ ID NO 78
<211> LENGTH: 43
<212> TYPE: DNA
<213> ORGANISM: Artificial Sequence
<220> FEATURE:
<223> OTHER INFORMATION: Oligonucleotide

<400> SEQUENCE: 78
aatgatacgg cgaccaccga gatctacact cgtcggcagc gtc					43

<210> SEQ ID NO 79
<211> LENGTH: 54
<212> TYPE: DNA
<213> ORGANISM: Artificial Sequence
<220> FEATURE:
<223> OTHER INFORMATION: Oligonucleotide

<400> SEQUENCE: 79
gtgactggag ttcagacgtg tgctcttccg atctggtctt gtagttgccg tcgt					54

<210> SEQ ID NO 80
<211> LENGTH: 56

```
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (25)..(32)
<223> OTHER INFORMATION: n is a, c, g, or t

<400> SEQUENCE: 80
caagcagaag acggcatacg agatnnnnnn nngtgactgg agttcagacg tgtgct        56

<210> SEQ ID NO 81
<211> LENGTH: 18
<212> TYPE: DNA
<213> ORGANISM: Artificial Sequence
<220> FEATURE:
<223> OTHER INFORMATION: Insertion

<400> SEQUENCE: 81
cagtgcttca gccgctac                                                   18

<210> SEQ ID NO 82
<211> LENGTH: 290
<212> TYPE: DNA
<213> ORGANISM: Artificial Sequence
<220> FEATURE:
<223> OTHER INFORMATION: Insertion

<400> SEQUENCE: 82
ggctccctgt aggcttcaac tcccagggct tcagtgatcc tccagctggg cccacaggtg     60
tgtgccacca ggtgtggcta attttttgta gaaacagagt ctggctatgt tgcccaggct    120
ggcctcaaac tcctggcctc aaggggatcc tcccaacctc agcatctcaa accagggtac    180
cttctagaag ccacaccttg tattgcgggc tccaagctgc actggcgcca ctggcatcgc    240
ccaccagggg gcaccgtgag ctcagtctga tgagcccagt ggcgccccca               290

<210> SEQ ID NO 83
<211> LENGTH: 161
<212> TYPE: DNA
<213> ORGANISM: Artificial Sequence
<220> FEATURE:
<223> OTHER INFORMATION: Insertion

<400> SEQUENCE: 83
ggcatgcgcc accacgccca gctgattttt gtattttag tagagacagg tttcaccatg      60
ttggccagga tggtctcgat gtcttgtcct cgtgatctgc ccacctcagc ctaccaaagt    120
gctgggatta caggcgtgag ccaccacacc cggctgacct a                        161

<210> SEQ ID NO 84
<211> LENGTH: 12
<212> TYPE: DNA
<213> ORGANISM: Artificial Sequence
<220> FEATURE:
<223> OTHER INFORMATION: Insertion

<400> SEQUENCE: 84
gttgaccacc tg                                                         12

<210> SEQ ID NO 85
<211> LENGTH: 418
<212> TYPE: DNA
<213> ORGANISM: Artificial Sequence
<220> FEATURE:
```

<223> OTHER INFORMATION: Insertion

<400> SEQUENCE: 85

| | | |
|---|---|---|
| tccccctagg gagactgggg agctcacctt ctagaaaaag aaaactgaca tccagactag | 60 |
| gttattctcc aaggtcatat agcccatcta agaggtaggg ccaggattag atagagaacg | 120 |
| agtaaaaaac ttcagggcat aaatccccgc tgaaaccgag ttttccaagt cacttgcctt | 180 |
| tgcttttgt tccacctttg gttggcaaaa atattataaa agcctaggca taatgagacc | 240 |
| tccaggcccc catccctgaa ccacaaacag ctccaggtca ctcacaccac acccttgtgt | 300 |
| cctggaaccg tgcctgggaa aagcttcccc aataagctgc tgccatatgc accgggcctc | 360 |
| cctgcctcgg gctccatcgt ggagacatac cagcccctgc agacaacccc gtgctagc | 418 |

<210> SEQ ID NO 86
<211> LENGTH: 281
<212> TYPE: DNA
<213> ORGANISM: Artificial Sequence
<220> FEATURE:
<223> OTHER INFORMATION: Insertion

<400> SEQUENCE: 86

| | | |
|---|---|---|
| atctatctta gagacagggt ctcacttggt cacccaggct ggagtgcagt ggcgtgatca | 60 |
| cggctccctg taggcttcaa ctcccagggc ttcagtgatc ctccagctgg gcccacaggt | 120 |
| gtgtgccacc aggtgtggct aattttttgt agaaacagag tctggctatg ttgcccaggc | 180 |
| tggcctcaaa ctcctggcct caagggatcc tcccacctca gcatctcaaa ccagggtacc | 240 |
| ttctagaagc cacaccttgt attgcgggct ccaagctgca c | 281 |

<210> SEQ ID NO 87
<211> LENGTH: 361
<212> TYPE: DNA
<213> ORGANISM: Artificial Sequence
<220> FEATURE:
<223> OTHER INFORMATION: Insertion

<400> SEQUENCE: 87

| | | |
|---|---|---|
| caggtgtggc taattttttg tagaaacaga gtctggctat gttgcccagg ctggcctcaa | 60 |
| actcctggcc tcaagggatc ctcccacctc agcatctcaa accagggtac cttctagaag | 120 |
| ccacaccttg tattgcgggc tccaagctgc actggcgcca ctggcatcgc ccaccagggg | 180 |
| gcaccgtgag ctcagtctga tgagcccagt ggcgccccca ggcagaggtg caatctgtgg | 240 |
| tgagagctcc caattccaga ccctgcacct gcccatggca tggggcaact ggacctctgc | 300 |
| tgctactccc tgtgtggccc aggagccacg caggctacag taccatgaac tgagagctgc | 360 |
| t | 361 |

<210> SEQ ID NO 88
<211> LENGTH: 289
<212> TYPE: DNA
<213> ORGANISM: Artificial Sequence
<220> FEATURE:
<223> OTHER INFORMATION: Insertion

<400> SEQUENCE: 88

| | | |
|---|---|---|
| ggatggtctc gatgtcttgt cctcgtgatc tgcccacctc agcctaccaa agtgctggga | 60 |
| ttacaggcgt gagccaccac acccggcctg aagcgggatt tcacaagac attttaacac | 120 |
| acacaagtca tgcctaggtg attaatatgc atgttaaagc agcattgttc agattataaa | 180 |

```
catgtgcgct gatacataac acataggctt tctgtgcttc acatgatcca gagtgtgtat    240
cagcacctgt taaggaattt cccctaccaa ggacaaggga cgtgcctga               289

<210> SEQ ID NO 89
<211> LENGTH: 193
<212> TYPE: DNA
<213> ORGANISM: Artificial Sequence
<220> FEATURE:
<223> OTHER INFORMATION: Insertion
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t

<400> SEQUENCE: 89
taaaacgacg gccagtgaat tgtaatacga ctcactatag ggngaattgg gccctctaga    60
tgcatgctcg agcggccgcc agtgtgatgg atatctgcag aattcgccct tgatggggtg   120
ggggttaaag gaggtggcag acagnctggg tgcagtggct cacgcctgta atcccaggcc   180
aaggcgagta gat                                                     193

<210> SEQ ID NO 90
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 90
aagaccttgc actacctgtg gcttccattt tcctg                              35

<210> SEQ ID NO 91
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 91
cagacctttc actactttt gcatcacttt ttttg                               35

<210> SEQ ID NO 92
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 92
tagacctttc actaactatg ttattccttt tgtct                              35

<210> SEQ ID NO 93
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 93
cagacctttc actaactcag cttccctgct ttgta                              35
```

<210> SEQ ID NO 94
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 94
gagacctttc actaccctgg ttagctgtat tcttg                      35

<210> SEQ ID NO 95
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 95
aagaccttcc actattataa tgctactttt tagtg                      35

<210> SEQ ID NO 96
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 96
gagaccttcc actagttgcc ccttcccta aaaac                       35

<210> SEQ ID NO 97
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 97
aagacctttc actatcagag gttgaaattc taata                      35

<210> SEQ ID NO 98
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 98
aagacctttc actatttgaa acaactgttt acagt                      35

<210> SEQ ID NO 99
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 99
aagaccttgc actagacatc ctttcctgtc ccctt                      35

<210> SEQ ID NO 100
<211> LENGTH: 35
<212> TYPE: DNA
<213> ORGANISM: Artificial Sequence
<220> FEATURE:
<223> OTHER INFORMATION: Predicted oligonucleotide

```
<400> SEQUENCE: 100
aagaagccga ggctccccca gcgaagcccc tttcc                              35

<210> SEQ ID NO 101
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 101
tagaagccga ggcttgcgaa acgaagcccg ataga                              35

<210> SEQ ID NO 102
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 102
cagaagccca ggctccccca aaggcattcg ctcct                              35

<210> SEQ ID NO 103
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 103
gagaagccaa ggcttcagta ctgaagggca tgtac                              35

<210> SEQ ID NO 104
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 104
cagaagccca ggctggggca gagagaggcc ttgct                              35

<210> SEQ ID NO 105
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 105
aagaagccca ggctggcctg ctggagacac gtgtc                              35

<210> SEQ ID NO 106
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 106
cagaagccaa ggctttctct ggcatgatct tttcc                              35

<210> SEQ ID NO 107
```

```
<210> SEQ ID NO 107
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 107
gagaagccca ggcttcccag ccagcctccc tctgc                                35

<210> SEQ ID NO 108
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 108
gagaagccca ggcttcccag ccagcctccc tctgc                                35

<210> SEQ ID NO 109
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 109
gagaagccca ggctcccaga gggagtgagc tgccc                                35

<210> SEQ ID NO 110
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 110
gagaagccaa ggctgccaaa caggagtaaa ttcac                                35

<210> SEQ ID NO 111
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 111
aaggctacgt ccaggagcgc accatcttct tcaag                                35

<210> SEQ ID NO 112
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 112
aaggctacct ccagacactg cccagcatcg tcatt                                35

<210> SEQ ID NO 113
<211> LENGTH: 35
<212> TYPE: DNA
<213> ORGANISM: Artificial Sequence
<220> FEATURE:
<223> OTHER INFORMATION: Predicted oligonucleotide
```

```
<400> SEQUENCE: 113
taggctactt ccagtaactc cccaaagtca tggga                                35

<210> SEQ ID NO 114
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 114
caggctacgt ccaggcacac accaattaga ttgag                                35

<210> SEQ ID NO 115
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 115
gaggctacat ccaggagctg cccatggcag gattg                                35

<210> SEQ ID NO 116
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 116
taggctacat ccagacatga ataagcatgt tcctg                                35

<210> SEQ ID NO 117
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 117
aaggctactt ccagaagtga tcacatcact tctgc                                35

<210> SEQ ID NO 118
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 118
aaggctacct ccagccccac actaccttct ctggc                                35

<210> SEQ ID NO 119
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 119
caggctacat ccagacacta tccatatgct tgaga                                35

<210> SEQ ID NO 120
```

```
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 120
caggctactt ccagatgtac tgactcagtc tctag                              35

<210> SEQ ID NO 121
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 121
caggctacat ccaggaatct cagaacttct tgagg                              35

<210> SEQ ID NO 122
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 122
aagctggaca tcacctccca caacgaggac tacac                              35

<210> SEQ ID NO 123
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 123
gagctggaga tcacctgctg gcagagggac taccc                              35

<210> SEQ ID NO 124
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 124
cagctggaca tcacatgcaa aaaaaaaat gagtc                               35

<210> SEQ ID NO 125
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 125
aagctggaaa tcacatccag gagtggagaa cagat                              35

<210> SEQ ID NO 126
<211> LENGTH: 35
<212> TYPE: DNA
<213> ORGANISM: Artificial Sequence
<220> FEATURE:
<223> OTHER INFORMATION: Predicted oligonucleotide
```

```
<400> SEQUENCE: 126
cagctggata tcaccataca gattgtgcac tgtac                              35

<210> SEQ ID NO 127
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 127
aagctggaaa tcacagccca cggccaaatc cagcc                              35

<210> SEQ ID NO 128
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 128
tagctggaaa tcactccata gagtgattag ttcat                              35

<210> SEQ ID NO 129
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 129
tagctggata tcacacaaaa taacaagaac ttgga                              35

<210> SEQ ID NO 130
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 130
tagctggata tcacctagag caatgagaac cattg                              35

<210> SEQ ID NO 131
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 131
gagctggaga tcactgcaga aagtgattac agtat                              35

<210> SEQ ID NO 132
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 132
aagtcgatgc ccttcagctc gatgcggttc accag                              35

<210> SEQ ID NO 133
```

```
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 133
gagtcgatgc ccttgttatc aatgatgtac tggaa                              35

<210> SEQ ID NO 134
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 134
gagtcgattc ccttaagagc catctaatag tcatg                              35

<210> SEQ ID NO 135
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 135
aagtcgatcc cctttgcccc aattccctca acact                              35

<210> SEQ ID NO 136
<211> LENGTH: 35
<212> TYPE: DNA
<213> ORGANISM: Artificial Sequence
<220> FEATURE:
<223> OTHER INFORMATION: Predicted oligonucleotide

<400> SEQUENCE: 136
aagtcgatac ccttcaggaa agtgctaagc aaggg                              35

<210> SEQ ID NO 137
<211> LENGTH: 43
<212> TYPE: DNA
<213> ORGANISM: artificial sequence
<220> FEATURE:
<223> OTHER INFORMATION: dTomato primer

<400> SEQUENCE: 137
caccaagctg gacatcacct cccacaacga ggactacacc atc                     43

<210> SEQ ID NO 138
<211> LENGTH: 43
<212> TYPE: DNA
<213> ORGANISM: artificial sequence
<220> FEATURE:
<223> OTHER INFORMATION: dTomato primer

<400> SEQUENCE: 138
gatggtgtag tcctcgttgt gggaggtgat gtccagcttg gtg                     43

<210> SEQ ID NO 139
<211> LENGTH: 43
<212> TYPE: DNA
<213> ORGANISM: artificial sequence
<220> FEATURE:
<223> OTHER INFORMATION: GFP
```

```
<400> SEQUENCE: 139
cccgaaggct acgtccagga gcgcaccatc ttcttcaagg acg                43

<210> SEQ ID NO 140
<211> LENGTH: 43
<212> TYPE: DNA
<213> ORGANISM: artificial sequence
<220> FEATURE:
<223> OTHER INFORMATION: GFP primer

<400> SEQUENCE: 140
cgtccttgaa gaagatggtg cgctcctgga cgtagccttc ggg                43

<210> SEQ ID NO 141
<211> LENGTH: 45
<212> TYPE: DNA
<213> ORGANISM: artificial sequence
<220> FEATURE:
<223> OTHER INFORMATION: GFP primer

<400> SEQUENCE: 141
acacacctgg tgaaccgcat cgagctgasa gggcatcgac ttcaa              45

<210> SEQ ID NO 142
<211> LENGTH: 43
<212> TYPE: DNA
<213> ORGANISM: artificial sequence
<220> FEATURE:
<223> OTHER INFORMATION: GFP primer

<400> SEQUENCE: 142
ttgaagtcga tgcccttcag ctcgatgcgg ttcaccaggg tgt                43

<210> SEQ ID NO 143
<211> LENGTH: 40
<212> TYPE: DNA
<213> ORGANISM: Homo sapiens

<400> SEQUENCE: 143
agtcaggaaa atggaagcca caggtagtgc aaggtcttgg                    40

<210> SEQ ID NO 144
<211> LENGTH: 40
<212> TYPE: DNA
<213> ORGANISM: Homo sapiens

<400> SEQUENCE: 144
ccaagacctt gcactacctg tggcttccat tttcctgact                    40

<210> SEQ ID NO 145
<211> LENGTH: 40
<212> TYPE: DNA
<213> ORGANISM: Homo sapiens

<400> SEQUENCE: 145
gagggaaagg ggcttcgctg ggggagcctc ggcttcttct                    40

<210> SEQ ID NO 146
<211> LENGTH: 40
<212> TYPE: DNA
<213> ORGANISM: Homo sapiens
```

-continued

```
<400> SEQUENCE: 146
agaagaagcc gaggctcccc cagcgaagcc cctttccctc                40

<210> SEQ ID NO 147
<211> LENGTH: 25
<212> TYPE: RNA
<213> ORGANISM: Artificial Sequence
<220> FEATURE:
<223> OTHER INFORMATION: crRNA

<400> SEQUENCE: 147
aagccgaggc uccccagcg aagcc                                 25

<210> SEQ ID NO 148
<211> LENGTH: 25
<212> TYPE: DNA
<213> ORGANISM: Artificial Sequence
<220> FEATURE:
<223> OTHER INFORMATION: crRNA

<400> SEQUENCE: 148
tagccgaggc uccccagcg aagcc                                 25
```